US010954436B2

(12) United States Patent
Suzenet et al.

(10) Patent No.: US 10,954,436 B2
(45) Date of Patent: Mar. 23, 2021

(54) POLYNITROGEN COMPOUNDS AND USES THEREOF AS FLUORESCENT CHROMOPHORES

(71) Applicants: UNIVERSITE D'ORLEANS, Orleans (FR); CENTRE NATIONAL DE LA RECHERCHE SCIENTIFIQUE, Paris (FR)

(72) Inventors: Franck Suzenet, La Chapelle Saint Mesmin (FR); Doina Sirbu, Olivet (FR); Gérald Guillaumet, Saint Jean le Blanc (FR); Pascal Bonnet, Olivet (FR)

(73) Assignees: UNIVERSITE D'ORLEANS, Orleans (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 274 days.

(21) Appl. No.: 15/746,386

(22) PCT Filed: Jul. 19, 2016

(86) PCT No.: PCT/EP2016/067215
§ 371 (c)(1),
(2) Date: Jan. 19, 2018

(87) PCT Pub. No.: WO2017/013135
PCT Pub. Date: Jan. 26, 2017

(65) Prior Publication Data
US 2018/0194997 A1 Jul. 12, 2018

(30) Foreign Application Priority Data
Jul. 20, 2015 (FR) .................................... 15 56868

(51) Int. Cl.
C09K 11/06 (2006.01)
C07D 487/14 (2006.01)
C07D 471/14 (2006.01)
C07D 487/04 (2006.01)
C07F 5/02 (2006.01)
C07F 7/08 (2006.01)
H01L 51/00 (2006.01)
G01N 33/58 (2006.01)
C07B 37/10 (2006.01)
C07B 43/04 (2006.01)

(52) U.S. Cl.
CPC ............ *C09K 11/06* (2013.01); *C07D 471/14* (2013.01); *C07D 487/04* (2013.01); *C07D 487/14* (2013.01); *C07F 5/025* (2013.01); *C07F 7/0812* (2013.01); *G01N 33/582* (2013.01); *H01L 51/0072* (2013.01); *C07B 37/10* (2013.01); *C07B 43/04* (2013.01)

(58) Field of Classification Search
CPC ... C09K 11/06; H01L 51/0072; C07F 7/0812; C07F 5/025; G01N 33/582; G01N 2021/6439; G01N 21/6428; C07D 487/04; C07D 471/14; C07D 487/14; C07B 43/04; C07B 37/10
See application file for complete search history.

(56) References Cited

U.S. PATENT DOCUMENTS

| 3,166,567 A | 1/1965 | Carboni |
| 3,262,942 A | 7/1966 | Carboni |
| 7,884,209 B2* | 2/2011 | Gruessing ............. C04B 24/006 548/110 |
| 8,273,877 B1 | 9/2012 | Stern et al. |
| 8,815,413 B2* | 8/2014 | Yersin .................. C07D 263/42 428/690 |
| 2014/0005410 A1* | 1/2014 | Namba ................ C07D 487/04 548/258 |

FOREIGN PATENT DOCUMENTS

| WO | WO 2005/121054 A2 | 12/2005 |
| WO | WO 2012/121356 A1 | 9/2012 |

OTHER PUBLICATIONS

Balachari, et al. 2000 "Synthesis, Thermal Stability and Impact Stability of Novel Tetranitro-Dipyridotetraazapentalene Derivatives" *Propellants, Explosives, Pyrotechnics* 25: 75-80.
Chemical Abstracts Database 1998 Accession No. 1998:574371 (XP-002751475) in 1 page.
Chemical Abstracts Database 1996 Accession No. 1996:17611 (XP-002751476) in 2 pages.
Galasso, et al. 2000 "A study of the molecular structure and spectroscopic properties of benzo- and pyrido-tetraazapentalenes" *Chemical Physics* 254: 375-384.
Lu and Boyer 1993 "Luminescent nitro derivatives of benzotriazolo [2,1a] benzotriazole" *Heteroatom Chemistry* 4(1): 91-96.
Maquestiau, et al. 1986 "Nitration de Pyridineobenzotetraazapentalenes" Bull. Soc. Chim. Belg. 95: 1119-1122.
Nyffenegger, et al. 2008 "An efficient route to polynitrogen-fused tricycles via a nitrene-mediated N-N bond formation under microwave irradiation" *Tetrahedron* 64: 9567-9573.

(Continued)

Primary Examiner — Lore R Jarrett
(74) Attorney, Agent, or Firm — Knobbe, Martens, Olson & Bear, LLP

(57) ABSTRACT

The present invention relates to the use, as a fluorescent chromophore, of a compound with formula (I) wherein: $A_1$ is —N— or —C($Y_1$)—; $A_2$ is —N— or —C($Y_2$)—; $A_3$ is —N— or —C($Y_3$)—; $A_4$ is —N— or —C($Y_4$)—; at least one of $A_1$, $A_2$, $A_3$ and $A_4$ representing —N—; $X_1$ is —N— or —C($Y_5$)—; $X_2$ is —N— or —C($Y_6$)—; $X_3$ is —N— or —C($Y_7$)—; and $Y_1$, $Y_2$, $Y_3$, $Y_4$, $Y_5$, $Y_6$ and $Y_7$ are in particular chosen independently of one another from the group made up of: H, electron-donor groups and electron-attracting groups.

18 Claims, No Drawings

(56) References Cited

OTHER PUBLICATIONS

International Search Report in PCT/EP2016/067215, dated Sep. 21, 2016.
Politzer et al. 1996 "Computational determination of heats of formation of energetic comppounds" Materials Research Society Symposium (in 14 pages).
Slepukhin, P.A., et al., Transformations of 8-substituted tetrazolo[1,5-a]pyrazines, Russian Chemical Bulletin, International Edition, vol. 56, No. 2, pp. 345-350, Feb. 2007.
Ramanaiah, K.C.V., et al., "Synthesis of 1-Substituted [1,2,3]Triazolo[4,5-d]pyridazines as Precursors for Novel Tetraazapentalene Derivatives." J. Heterocyclic Chem., 37, 1597 (2000).
Nyffenegger, Coralie, "Synthesis of Nitro-Functionalized Polynitrogen Tricycles Bearing a Central 1,2,3-Triazolium Ylide," Synlett 2009, No. 8, pp. 1318-1320.
Maquestiau. A., et al, "Synthese Et Reactions De Deplacement Nucleophile De Derives Nitres Et Halogenes Du [3, 2-b] Pyridino [4.5] Benzo-1,3a,6,61-Tetraazapentalene," Vull. Soc. Chim. Belg. vol. 93, No. 11, 1984 (in 11 pages).
Lu, Q., et al., Luminescent Nitro Derivatives of Benzotriazolo[2,1a]benzotriazole, Heteroatom Chemistry, vol. 4, No. 1, 1993. ET AL. (1992).

\* cited by examiner

POLYNITROGEN COMPOUNDS AND USES THEREOF AS FLUORESCENT CHROMOPHORES

FIELD OF THE INVENTION

The present invention relates to new poly nitrogen compounds, in particular compounds comprising a1,3a,6a-triazapentalene pattern, and uses thereof as fluorescent chromophores.

It also relates to the use of these compounds in particular in the field of biological imaging or fluorescence microscopy.

BACKGROUND

Over the last twenty years, the use of fluorescence in living chemistry has experienced considerable expansion. It is currently used in applications in biotechnology, flux cytometry, medical diagnostics, DNA sequencing, cellular imaging, etc. In many applications, the high sensitivity of this technique has in particular made it possible to replace certain markers based on radioactive elements, the application of which is highly delicate. The expansion of these techniques was enshrined in 2008, during the recognition of GFP (Green Fluorescence Protein) applications. The current technologies make fluorescence an important key field in living science.

Among the various classes of fluorescent markers, organic fluorophores stand out owing to their unique photophysical properties. The latter are primarily represented by Cyanines, Fluoresceins, Rhodamines, Alea fluors and BODIPYs. Their uses within different fields are diverse and varied. Although widely used, these compounds still suffer from flaws that decrease the scope of their action in the biology field. In particular, these compounds have the drawback of having a low Stokes displacement due to the energy proximity of the emitting and absorption waves (about 20 nm for Cyanines, 10-20 nm for BODIPYs, 30 nm for Fluoresceins and 20 nm for Rhodamines). These are also compounds with complex chemical structures, obtained through tedious synthetic avenues. Some of these compounds also have a low solubility in aqueous mediums.

At this time, there is therefore a need to provide fluorescent compounds obtained through simpler synthetic avenues, preferably soluble in an aqueous medium, and having a high Stokes displacement.

SUMMARY OF THE INVENTION

One aim of the present invention consists of providing new fluorescent compounds, in particular soluble in water.

The invention also aims to provide new fluorescent polycyclic compounds with a low molecular weight relative to the compounds known at this time.

The invention also aims to provide new fluorescent compounds having significant Stokes displacements and high quantum yields, in particular greater than 10%, in particular up to 55% in dichloromethane, and high absorption coefficients, preferably up to 18,000.

The invention also aims to provide new fluorescent compounds that are stable in an aqueous medium with an acid, neutral and basic pH.

One aim of the present invention consists of providing new fluorescent compounds intended to prepare bio-conjugates for detecting biological molecules.

Thus, the present invention relates to the use, as a fluorescent chromophore, of a compound with formula (I):

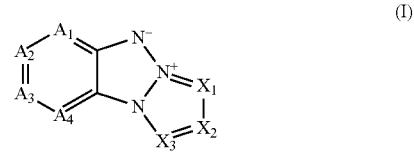

(I)

wherein:
$A_1$ is —N— or —C($Y_1$)—;
$A_2$ is —N— or —C($Y_2$)—;
$A_3$ is —N— or —C($Y_3$)—;
$A_4$ is —N— or —C($Y_4$)—;
at least one of $A_1$, $A_2$, $A_3$ and $A_4$ representing —N—;
$Y_1$, $Y_2$, $Y_3$ and $Y_4$ are chosen independently of one another in the group made up of: H, electron-donor groups and electron-attracting groups,
where $Y_1$ and $Y_2$ together form, with the carbon atoms that carry them, a (hetero)cycloalkyl group or a (hetero)aryl group comprising from 5 to 30 atoms,
and/or $Y_2$ and $Y_3$ together form, with the carbon atoms that carry them, a (hetero)cycloalkyl group or a (hetero)aryl group comprising from 5 to 30 atoms,
and/or $Y_3$ and $Y_4$ together form, with the carbon atoms that carry them, a (hetero)cycloalkyl group or a (hetero)aryl group comprising from 5 to 30 atoms,
$X_1$ is —N— or —C($Y_5$)—;
$X_2$ is —N— or —C($Y_6$)—;
$X_3$ is —N— or —C($Y_7$)—;
$Y_5$, $Y_6$ and $Y_7$ are chosen independently of one another in the group made up of H, electron-donor groups and electron-attracting groups,
where $Y_5$ and $Y_6$ together form, with the carbon atoms that carry them, a (hetero)cycloalkyl group or a (hetero)aryl group comprising from 5 to 10 atoms,
and/or $Y_6$ and $Y_7$ together form, with the carbon atoms that carry them, a (hetero)cycloalkyl group or a (hetero)aryl group comprising from 5 to 10 atoms,
said compound with formula (I) being able to be in salt or pure stereoisomer form or in the form of a mixture of enantiomers and/or diastereoisomers, including racemic mixtures, or in the form of tautomers,
with the exception of the compound with formula:

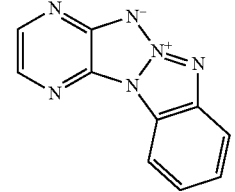 [SMILES: c1ccc2c(c1)n[n+]1[n-]c3nccnc3n21]

The present invention also relates to compounds with the following formula (I) as such:

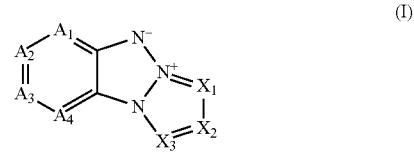

(I)

wherein:
A$_1$ is —N— or —C(Y$_1$)—;
A$_2$ is —N— or —C(Y$_2$)—;
A$_3$ is —N— or —C(Y$_3$)—;
A$_4$ is —N— or —C(Y$_4$)—;
at least one of A$_1$, A$_2$, A$_3$ and A$_4$ representing —N—;
Y$_1$, Y$_2$, Y$_3$ and Y$_4$ are chosen independently of one another in the group made up of: H, electron-donor groups and electron-attracting groups,
where Y$_1$ and Y$_2$ together form, with the carbon atoms that carry them, a (hetero)cycloalkyl group or a (hetero)aryl group comprising from 5 to 30 atoms,
and/or Y$_2$ and Y$_3$ together form, with the carbon atoms that carry them, a (hetero)cycloalkyl group or a (hetero)aryl group comprising from 5 to 30 atoms,
and/or Y$_3$ and Y$_4$ together form, with the carbon atoms that carry them, a (hetero)cycloalkyl group or a (hetero)aryl group comprising from 5 to 30 atoms,
X$_1$ is —N— or —C(Y$_5$)—;
X$_2$ is —N— or —C(Y$_6$)—;
X$_3$ is —N— or —C(Y$_7$)—;
Y$_5$, Y$_6$ and Y$_7$ are chosen independently of one another in the group made up of H, electron-donor groups and electron-attracting groups,
where Y$_5$ and Y$_6$ together form, with the carbon atoms that carry them, a (hetero)cycloalkyl group or a (hetero)aryl group comprising from 5 to 10 atoms,
and/or Y$_6$ and Y$_7$ together form, with the carbon atoms that carry them, a (hetero)cycloalkyl group or a (hetero)aryl group comprising from 5 to 10 atoms,
said compound with formula (I) being able to be in salt or pure stereoisomer form or in the form of a mixture of enantiomers and/or diastereoisomers, including racemic mixtures, or in the form of tautomers,
with the exception of the following compounds:

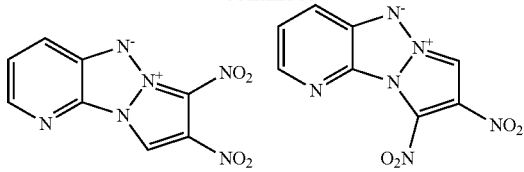
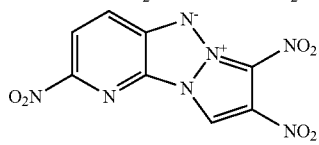
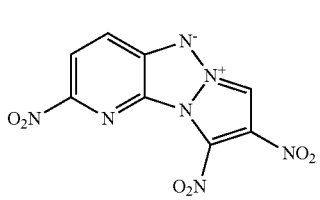
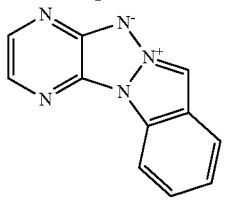
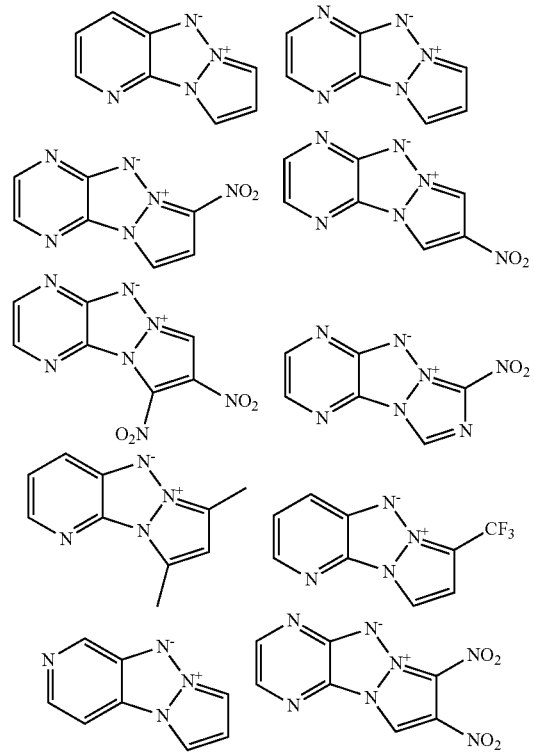
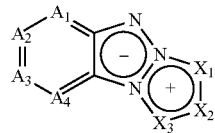

According to the invention, the compound with formula (I) may exist in different tautomer forms. Consequently, the present invention also relates to the tautomer forms of compounds with formula (I).

In particular, the compounds with formula (I) can also be represented by the following formula:

DETAILED DESCRIPTION

According to the invention, the term "fluorescent chromophore" designates a molecule able to re-emit light after excitation with a quantum efficiency greater than 0.001 (0.1%).

According to the invention, the term "(hetero)cycloalkyl" encompasses both the terms "cycloalkyl" and "heterocycloalkyl," these terms being as defined below.

According to the invention, the term "(hetero)aryl" encompasses both the terms "aryl" and "heteroaryl," these terms being as defined below.

According to the invention, when the Y$_i$ et Y$_{i+1}$ groups (i being an integer from 1 to 6) together form, with the carbon atoms that carry them, a (hetero)cycloalkyl group, optionally substituted, or a (hetero)aryl group, optionally substituted, comprising from 5 to 10 atoms, these ring groups can either be a mono-cycle or bi-cycles, or even (poly)cycles. They can therefore also form fused cycles themselves.

According to the invention, the term "electron-donor group" designates an atom or atom group that shares part of its electron density with an adjacent conjugated system (here, the pattern with formula (I)) by resonance (mesomere effect) or inductive effect.

Among the preferred electron-donor groups, examples include hydroxy, alkoxy, thiol, alkylthio, alkyl, alkene, alkyne, amino, alkylamino and aryl groups, in turn carrying one or several electron-donor groups.

According to the invention, the term "electron-attracting group" designates an atom or atom group that attracts, generally by resonance or inductive effect, part of the electron density of a neighbor (here, the pattern with formula (I)) on which it is fixed.

Among the preferred electron-attracting groups, examples include halogenoalkyl, nitro, acyl, carboxyl, ester, formyl, sulfonyl, trifluoromethyl, cyano, halogen and aryl groups, in turn carrying one or several electron-attracting groups.

According to one embodiment, in formula (I) according to the invention, $Y_1$, $Y_2$, $Y_3$ and $Y_4$ are chosen independently of one another in the group made up of: H, halogen, $(C_1-C_6)$ alkyl, $(C_6-C_{10})$aryl, heteroaryl comprising from 5 to 10 atoms, $(C_2-C_6)$alkenyl, $(C_2-C_6)$alkynyl, CN, hydroxy, $(C_1-C_6)$alcoxy, thiol, $(C_1-C_6)$alkylthio, $(CH_2)_nSO_2$—$OR_a$ where n=1-6, $CH_2SO_2$—$NR_aR_b$, $NO_2$, $SO_3R_a$, $NR_aR_b$, $C(O)OR_a$, $C(O)R_a$, and $C(O)NR_aR_b$, $R_a$ and $R_b$ representing H or a $(C_1-C_6)$alkyl group. According to one embodiment, in formula (I) according to the invention, $Y_1$, $Y_2$, $Y_3$ and $Y_4$ can represent an ethynyl group, substituted by a phenyl group, optionally substituted by one or several substituents. The potential substituents in this phenyl group include the following groups: amino, hydroxy, thiol, oxo, halogen, alkyl, alkoxy, alkylthio, alkylamino, aryloxy, arylalcoxy, cyano, nitro, trifluoromethyl, sulfonate, carboxy or carboxyalkyl.

When $Y_2$, $Y_3$ and $Y_4$ are chosen from among the $(C_1-C_6)$ alkyl, $(C_6-C_{10})$aryl, heteroaryl, $(C_2-C_6)$alkenyl or $(C_2-C_6)$ alkynyl groups, the latter may further comprise at least one substituent. These substituents include the following groups: amino, hydroxy, thiol, oxo, halogen, alkyl, alkoxy, alkylthio, alkylamino, aryloxy, arylalcoxy, cyano, nitro, trifluoromethyl, sulfonate, carboxy or carboxyalkyl.

According to one embodiment, in formula (I) according to the invention, $Y_5$, $Y_6$, and $Y_7$ represent, independently of one another, a hydrogen atom or a halogen atom, or are chosen from the group made up of:

a $(C_1-C_6)$alkyl, $(C_3-C_6)$cycloalkyl or $(C_6-C_{10})$aryl group, said $(C_6-C_{10})$aryl group optionally being substituted by at least one substituent chosen from among: halogen, CN, $(C_1-C_6)$alkyl, OH, $(C_1-C_6)$alkoxy, $C(O)OR_a$ and $NR_aR_b$, $R_a$ and $R_b$ representing H or a $(C_1-C_6)$alkyl group, a heteroaryl group comprising from 5 to 10 chain links and containing from 1 to 4 heteroatoms chosen from among O, S or N, said heteroaryl group optionally being substituted by at least one substituent chosen from among: halogen, CN, $(C_1-C_6)$alkyl, OH, $(C_1-C_6)$ alkoxy, $C(O)OR_a$ and $NR_aR_b$, $R_a$ and $R_b$ representing H or a $(C_1-C_6)$alkyl group, a heterocycloalkyl group comprising from 4 to 10 chain links and containing from one to three heteroatoms chosen from among O, S or N, $NO_2$,

CHO, a $C(O)OR_a$ group, $R_a$ being as defined above, a —HC=CH—Ar group, Ar representing a $(C_6-C_{10})$aryl group, $SO_3H$ (or its salt), a $NR_cR_d$ group, $R_c$ and $R_d$ representing H or a $(C_1-C_6)$ alkyl group, or being able to form a hetero$(C_2-C_5)$ cycloalkyl group with the nitrogen atom that carries them;

an $OR_e$ group, $R_e$ representing H, a $(C_1-C_6)$alkyl group or a $(C_6-C_{10})$aryl group; and a group with the following formula (A):

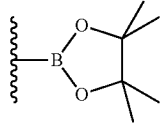

(A)

According to one embodiment, in formula (I) according to the invention, $Y_5$, $Y_6$ and $Y_7$ can represent an ethynyl group, substituted by a phenyl group, optionally substituted. The potential substituents in this phenyl group include the following groups: amino, hydroxy, thiol, oxo, halogen, alkyl, alkoxy, alkylthio, alkylamino, aryloxy, arylalcoxy, cyano, nitro, trifluoromethyl, sulfonate, carboxy or carboxyalkyl.

In the context of the present invention, $(C_t-C_z)$ group refers to a group comprising a carbon chain that may have from t to z carbon atoms, for example $C_1-C_6$, a carbon chain that may have from 1 to 6 carbon atoms.

In the context of the present invention, the term "halogen atom" refers to the fluorine, chlorine, bromine or iodine atoms.

According to the invention, the term "alkyl" designates hydrocarbon, saturated, linear or branched aliphatic groups comprising, unless otherwise stated, from 1 to 6 carbon atoms. Examples include methyl, ethyl, n-propyl, isopropyl, butyl, isobutyl, tertbutyl or pentyl groups.

According to the invention, the term "alkyl" designates hydrocarbon, saturated, linear or branched aliphatic groups comprising, unless otherwise stated, from 3 to 6 carbon atoms. Examples include cyclopropyl, cyclobutyl, cyclopentyl or cyclohexyl groups.

According to the invention, the term "halogenoalkyl" refers to an alkyl group as defined above, in which one or several hydrogen atoms is (are) replaced by a halogen atom. Examples include fluoroalkyls, in particular $CF_3$ or $CHF_2$.

According to the invention, the term "alkoxy" designates an —O-alkyl radical where the alkyl group is as previously defined. Examples include the —O—$(C_1-C_4)$alkyl group, and in particular the —O-methyl group, the —O-ethyl group, such as the —O—$C_3$alkyl group, the —O-propyl group, —O-isopropyl, and such as the —O—$C_4$alkyl group, the —O-butyl group, —O-isobutyl, —O-tertbutyl.

According to the invention, the arrow groups are aromatic ring groups comprising between 6 and 10 carbon atoms. Examples of aryl groups include phenyl or naphthyl groups.

According to the invention, the term "heteroaryl" designates a monocyclic or bicyclic aromatic group with 5 to 10 chain links containing from 1 to 4 heteroatoms chosen from among O, S or N. According to the invention, the term "bicyclic heteroaryl" includes fused aromatic bicycles.

Examples include the imidazolyl, thiazolyl, oxazolyl, furanyl, thiophenyl, pyrazolyl, oxadiazolyl, tetrazolyl, pyridinyl, pyrazinyl, pyrimidinyl, pyridazinyl, indolyl, benzofuranyl, benzothiophenyl, benzoxazolyl, benzimidazolyl, indazolyl, benzothiazolyl, isobenzothiazolyl, benzotriazolyl, quinoleinyl, isoquinoleinyl groups.

Heteroaryls comprising 5 to 6 atoms, including 1 to 4 nitrogen atoms, in particular include the following representative groups: pyrrolyl, pyrazolyl, 1,2,3-triazolyl, 1,2,4-triazolyl, tetrazolyl and 1,2,3-triazinyl.

Heteroaryl examples also include thiophenyl, oxazolyl, furazanyl, 1,2,4-thiadiazolyl, naphthyridinyl, quinoxalinyl, phtalazinyl, imidazo[1,2-a]pyridine, imidazo[2,1-b]thiazolyl, cinnolinyl, benzofurazanyl, azaindolyl, benzimidazolyl, benzothiophenyl, thienopyridyl, thienopyrimidinyl, pyrrolopyridyl, imidazopyridyl, benzoazaindol, 1,2,4-triazinyl, indolizinyl, isoxazolyl, isoquinolinyl, isothiazolyl, purinyl, quinazolinyl, quinolinyl, isoquinolyl, 1,3,4-thiadiazolyl, thiazolyl, isothiazolyl, carbazolyl, as well as the corresponding groups resulting from their fusion or the fusion with the phenyl core.

According to the invention, the term "heterocycloalkyl" refers to a monocyclic or bicyclic saturated or partially unsaturated group with 4 to 10 chain links, comprising from one to three heteroatoms chosen from among O, S or N, the heterocycloalkyl group being able to be attached to the rest of the molecule by a carbon atom or by a heteroatom. According to the invention, the term "bicyclic heterocycloalkyl" includes fused bicycles.

Saturated heterocycloalkyls comprising from 5 to 6 atoms include oxetanyl, tetrahydrofuranyl, dioxolanyl, pyrrolidinyl, azepinyl, oxazepinyl, pyrazolidinyl, imidazolidinyl, tetrahydrothiophenyl, dithiolanyl, thiazolidinyl, tetrahydropyranyl, tetrahydropyridinyl, dioxanyl, morpholinyl, piperidinyl, piperazinyl, tetrahydrothiopyranyl, dithianyl, thiomorpholinyl, or isoxazolidinyl.

According to the invention, the term "alkylthio" refers to a —S-alkyl group, the alkyl group being as defined above.

According to the invention, the term "alkylamino" refers to a —NH-alkyl or N(alkyl)$_2$ group, the alkyl group being as defined above.

According to the invention, the term "aryloxy" refers to an —O-aryl group, the aryl group being as defined above.

According to the invention, the term "arylalkoxy" refers to an -aryl-alkoxy-group, the aryl and alkoxy groups being as defined above.

According to the invention, the term "carboxyalkyl" refers to a HOOC-alkyl-group, the alkyl group being as defined above. Examples of carboxyalkyl groups in particular include carboxymethyl or carboxyethyl.

According to the invention, the term "carboxyl" designates a COOH group, and the term "oxo" designates a C(O) group.

The "alkyl," "cycloalkyl," "aryl," "heteroaryl" and "heterocycloalkyl" radicals mentioned above can be substituted by one or several substituents. These substituents include the following groups: amino, hydroxy, thiol, oxo, halogen, alkyl, alkoxy, alkylthio, alkylamino, aryloxy, arylalcoxy, cyano, trifluoromethyl, carboxy or carboxyalkyl.

When an alkyl radical is substituted by an aryl group, reference is made to an "arylalkyl" or "aralkyl" radical. The "arylalkyl" or "aralkyl" radicals are aryl-alkyl-radicals, the aryl and alkyl groups being as defined above. Arylalkyl radicals in particular include the benzyl or phenethyl radical.

One particular family of compounds according to the invention, and used as fluorescent chromophores, is made up of compounds with formula (I) in which $A_1$ is —N—.

Such a family of compounds satisfies the following formula (II):

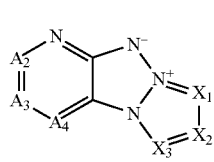

(II)

$A_2$, $A_3$, $A_4$, $X_1$, $X_2$ and $X_3$ being as defined above in formula (I).

One particular family of compounds according to the invention, and used as fluorescent chromophores, is made up of compounds with formula (I) in which A and $A_4$ are —N—, $A_2$ is —C($Y_2$)— and $A_3$ is —C($Y_3$)—.

This family of compounds, derived from pyrazine, satisfies the following formula (III):

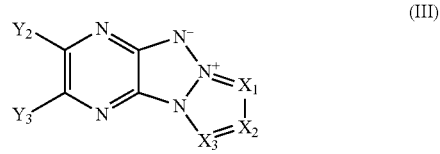

(III)

$Y_2$, $Y_3$, $X_1$, $X_2$, $X_2$ and $X_3$ being as defined above in formula (I).

Preferably, in formula (III), $Y_2$ and $Y_3$ are H or an electro-attracting group. Preferably, in formula (III), $Y_2$ and $Y_3$ are H.

Another particular family of compounds according to the invention, and used as fluorescent chromophores, is made up of compounds with formula (I) in which $A_1$ and $A_4$ are —N—, $A_2$ is —CH— and $A_3$ is —C($Y_3$)—.

This family of compounds satisfies the following formula (III-1):

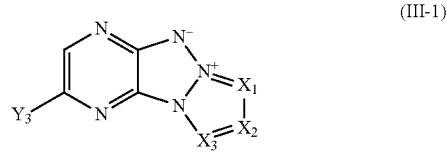

(III-1)

$Y_3$, $X_1$, $X_2$ and $X_3$ being as defined above in formula (I).

Preferably, in formula (III-1), $Y_3$ is an electro-attracting group. Preferably, $Y_3$ is a (hetero)aryl group, optionally substituted, as defined above.

Another particular family of compounds according to the invention, and used as fluorescent chromophores, is made up of compounds with formula (I) in which $Y_2$ and $Y_3$ together form, with the carbon atoms that carry them, a phenyl group, optionally substituted, or a heterocycloalkyl group, optionally substituted.

The potential substituents of the phenyl group for example include the following groups: amino, hydroxy, thiol, oxo, halogen, alkyl, alkoxy, alkylthio, alkylamino, aryloxy, arylalcoxy, cyano, trifluoromethyl, carboxy or carboxyalkyl.

Compounds satisfying the following formula (IV) may for example be cited:

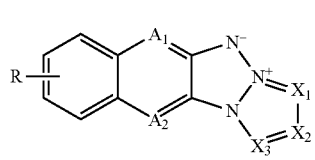

(IV)

$A_1$, $A_2$, $X_1$, $X_2$ and $X_3$ being as defined above in formula (I), R representing H or at least one substituent chosen from among the substituents mentioned above.

Preferably, in formula (IV), $A_1$ and $A_2$ are —N—.

Preferably, in formula (IV), R is H.

Another particular family of compounds according to the invention, and used as fluorescent chromophores, is made up of compounds with formula (I) in which $X_1$ is —C($Y_5$)—, $X_2$ is —C($Y_6$)— and $X_3$ is —C($Y_7$)—.

Such a family of compounds satisfies the following formula (V):

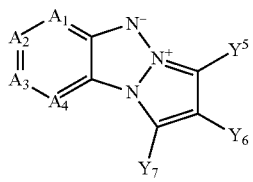

(V)

$A_1$, $A_2$, $A_3$, $A_4$, $Y_5$, $Y_6$ and $Y_7$ being as defined above in formula (I).

According to one embodiment, in formula (V) $A_1$ and $A_4$ are —N— and $A_2$ and $A_3$ are —CH—. Such a sub-family of compounds satisfies the following formula (V-1):

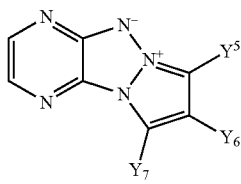

(V-1)

$Y_5$, $Y_6$ and $Y_7$ being as defined above in formula (I).

Preferably, in formula (V) or (V-1), only one of $Y_5$, $Y_6$ and $Y_7$ is different from H.

A sub-family of compounds with formula (V) is made up of compounds with formula (V-2) below:

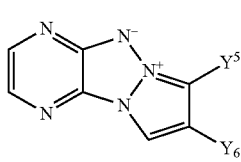

(V-2)

$Y_5$ and $Y_6$ being as defined above in formula (I).

A sub-family of compounds with formula (V) is made up of compounds with formula (V-3) below:

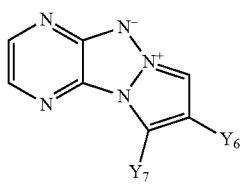

(V-3)

$Y_6$ and $Y_7$ being as defined above in formula (I).

Another particular family of compounds according to the invention, and used as fluorescent chromophores, is made up of compounds with formula (I) in which $X_1$ is —CH—, $X_2$ is —C($Y_6$)— and $X_3$ is —CH—, $Y_6$ being different from H.

Such a family of compounds satisfies the following formula (VI):

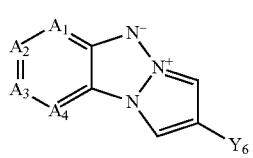

(VI)

$A_1$, $A_2$, $A_3$, $A_4$ and $Y_6$ being as defined above in formula (I).

The compounds with formula (VI) correspond to the compounds with formula (V), in which $Y_5$=$Y_7$=H.

According to one embodiment, in formula (VI) mentioned above, $A_1$ and $A_4$ are —N— and $A_2$ and $A_3$ are —CH—. This family of compounds satisfies the following formula (VI-1):

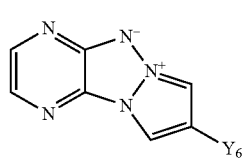

(VI-1)

$Y_6$ being as defined above in formula (I).

Preferably, in formulas (VI) or (VI-1), $Y_6$ represents a hydrogen atom or a halogen atom, in particular Br or I, or is chosen from the group made up of:

- a ($C_6$-$C_{10}$)aryl group, preferably phenyl, optionally substituted by at least one substituent, preferably in para, chosen from among: ($C_1$-$C_6$)alkoxy, C(O)O$R_a$ and N$R_aR_b$, $R_a$ and $R_b$ representing H or a ($C_1$-$C_6$)alkyl group,
- a heteroaryl group comprising from 5 to 10 chain links and containing from 1 to 4 heteroatoms chosen from among O, S or N, preferably thiophenyl, optionally substituted by C(O)O$R_a$, $R_a$ being as defined above, or pyrimidinyl,
- COOH,
- CH═CH-phenyl,
- $NO_2$, and
- a group with formula (A) as defined above.

Another particular family of compounds according to the invention, and used as fluorescent chromophores, is made up of compounds with formula (I) in which $X_1$ is —C($Y_5$)—, $X_2$ is —CH— and $X_3$ is —CH—, $Y_5$ being different from H.

Such a family of compounds satisfies the following formula (VII):

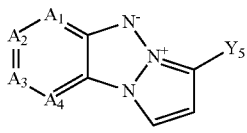

(VII)

$A_1$, $A_2$, $A_3$, $A_4$ and $Y_5$ being as defined above in formula (I).

The compounds with formula (VII) correspond to the compounds with formula (V), in which $Y_6=Y_7=H$.

According to one embodiment, in formula (VII) mentioned above, $A_1$ and $A_4$ are —N— and $A_2$ and $A_3$ are —CH—. This family of compounds satisfies the following formula (VII-1):

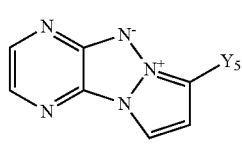

$Y_5$ being as defined above in formula (I).

Preferably, in formulas (VII) or (VII-1), $Y_5$ represents $NO_2$, a halogen, in particular I, an aryl group, in particular phenyl, or an $OR_e$ group, $R_e$ representing H or a ($C_1$-$C_6$) alkyl group.

Another particular family of compounds according to the invention, and used as fluorescent chromophores, is made up of compounds with formula (I) in which at least one of $X_1$ and $X_2$ is —N— and $X_3$ is —C($Y_7$)—.

In this family of compounds, the following sub-families can be mentioned:

compounds with the following formula (VIII):

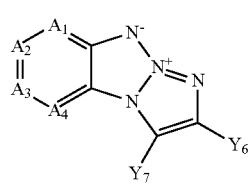

$A_1$, $A_2$, $A_3$, $A_4$, $Y_6$ and $Y_7$ being as defined above in formula (I); and compounds with the following formula (IX):

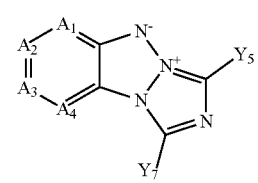

$A_1$, $A_2$, $A_3$, $A_4$, $Y_5$ and $Y_7$ being as defined above in formula (I).

According to one embodiment, in formula (VII), $Y_6$ and $Y_7$ are H.

According to one embodiment, in formula (IX), $Y_5$ and $Y_7$ are H.

According to one embodiment, in formula (IX), $Y_5$ is $NO_2$ and $Y_7$ is H.

According to one embodiment, in formula (IX), $Y_5$ is an alkyl group, in particular methyl, and $Y_7$ is a heterocycloalkyl, in particular morpholine.

According to one embodiment, in formulas (VIII) and (IX), $A_1$ and $A_4$ are —N— and $A_2$ and $A_3$ are —CH—.

Another particular family of compounds according to the invention, and used as fluorescent chromophores, is made up of compounds with formula (I) in which $Y_6$ and $Y_7$ together form, with the carbon atoms that carry them, a (hetero)aryl group, optionally substituted, preferably a phenyl group or a pyrazine group.

Preferably, for this family of compounds, $X_1$ is —CH—.

The potential substituents of the aforementioned phenyl group for example include the amino, hydroxy, thiol, oxo, halogen, heteroaryl, alkyl, alkoxy, alkylthio, alkylamino, aryloxy, arylalcoxy, cyano, trifluoromethyl, nitro, carboxy or carboxyalkyl groups, or a —C(O)—NH—CH$_2$—C≡C, group or a $SO_3H$ or $SO_3Na$ group.

Another particular family of compounds according to the invention, and used as fluorescent chromophores, is made up of compounds with formula (VIII) in which $Y_6$ and $Y_7$ together form, with the carbon atoms that carry them, an aryl group, optionally substituted, preferably a phenyl group.

The potential substituents of the aforementioned phenyl group for example include the amino, hydroxy, thiol, oxo, halogen, heteroaryl, alkyl, alkoxy, alkylthio, alkylamino, aryloxy, arylalcoxy, cyano, trifluoromethyl, nitro, carboxy or carboxyalkyl groups, or a —C(O)—NH—CH$_2$—C≡, group or a $SO_3H$ or $SO_3Na$ group.

Another particular family of compounds according to the invention, and used as fluorescent chromophores, is made up of compounds with formula (V-2) in which $Y_5$ and $Y_6$ together form, with the carbon atoms that carry them, a (hetero)aryl group, optionally substituted, preferably a phenyl or pyrazine group.

The potential substituents of the aforementioned phenyl group for example include the amino, hydroxy, thiol, oxo, halogen, heteroaryl, alkyl, alkoxy, alkylthio, alkylamino, aryloxy, arylalcoxy, cyano, trifluoromethyl, nitro, carboxy or carboxyalkyl groups, or a —C(O)—NH—CH$_2$—C≡C, group or a $SO_3H$ or $SO_3Na$ group.

Another particular family of compounds according to the invention, and used as fluorescent chromophores, is made up of compounds with formula (V-3) in which $Y_6$ and $Y_7$ together form, with the carbon atoms that carry them, a (hetero)aryl group, optionally substituted, preferably a phenyl or pyrazine group.

The potential substituents of the aforementioned phenyl group for example include the amino, hydroxy, thiol, oxo, halogen, heteroaryl, alkyl, alkoxy, alkylthio, alkylamino, aryloxy, arylalcoxy, cyano, trifluoromethyl, nitro, carboxy or carboxyalkyl groups, or a —C(O)—NH—CH$_2$—C≡C, group or a $SO_3H$ or $SO_3Na$ group.

The present invention also relates as such to the compounds with formula (II), (III), (III-1), (IV), (V), (V-1), (V-2), (V-3), (VI), (VI-1), (VII), (VII-1), (VIII) and (IX) as defined above.

The present invention also relates to an aqueous composition comprising at least one compound with formula (I) as defined above.

The present invention also relates to a compound with the following formula (I'):

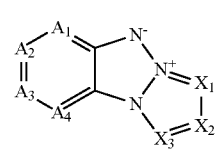

wherein:
$A_1$ is —N— or —C($Y_1$)—;
$A_2$ is —N— or —C($Y_2$)—;
$A_3$ is —N— or —C($Y_3$)—;
$A_4$ is —N— or —C($Y_4$)—;
at least one of $A_1$, $A_2$, $A_3$ and $A_4$ representing —N—;
$Y_1$, $Y_2$, $Y_3$ and $Y_4$ are chosen independently of one another in the group made up of: H, electro-donor groups and electro-attracting groups, or can represent a group with formula -L-Z, L representing a spacer arm comprising from 1 to 10 carbon atoms and Z representing a reactive group able to bond to a biological molecule,
where $Y_1$ and $Y_2$ together form, with the carbon atoms that carry them, a (hetero)cycloalkyl group or a (hetero)aryl group comprising from 5 to 30 atoms,
and/or $Y_2$ and $Y_3$ together form, with the carbon atoms that carry them, a (hetero)cycloalkyl group or a (hetero)aryl group comprising from 5 to 30 atoms,
and/or $Y_3$ and $Y_4$ together form, with the carbon atoms that carry them, a (hetero)cycloalkyl group or a (hetero)aryl group comprising from 5 to 30 atoms,
$X_1$ is —N— or —C($Y_5$)—;
$X_2$ is —N— or —C($Y_6$)—;
$X_3$ is —N— or —C($Y_7$)—;
$Y_5$, $Y_6$ and $Y_7$ are chosen independently of one another in the group made up of H, electron-donor groups and electron-attracting groups, or represent a group with formula -L-Z, L and Z being as defined above,
where $Y_5$ and $Y_6$ together form, with the carbon atoms that carry them, a (hetero)cycloalkyl group or a (hetero)aryl group comprising from 5 to 10 atoms,
and/or $Y_6$ and $Y_7$ together form, with the carbon atoms that carry them, a (hetero)cycloalkyl group or a (hetero)aryl group comprising from 5 to 10 atoms,
said compound with formula (I') being able to be in salt or pure stereoisomer form or in the form of a mixture of enantiomers and/or diastereoisomers, including racemic mixtures, or in the form of tautomers,
wherein at least one of $Y_1$, $Y_2$, $Y_3$, $Y_4$, $Y_5$, $Y_6$ and $Y_7$ is a group with formula -L-Z.

The compounds with formula (I') are compounds derived from compounds with formula (I). These compounds comprise at least one -L-Z group as defined above and are used to prepare conjugates as described later. They are therefore intended for subsequent coupling with biological molecules as defined below.

Preferably, in formula (I'), L is a $(C_1-C_{10})$alkylene radical, a $(C_6-C_{10})$arylene radial, a $—(C_2-C_6)$alkynylene radical or a $—(C_2-C_6)$alkynyl-$(C_1-C_6)$alkylene- radical, or a $—(C_2-C_6)$ alkynyl-$(C_6-C_{10})$arylene radical.

According to one particular embodiment, in formula (I'), the -L-Z group is chosen from among the following groups:
a group with the following formula (B):

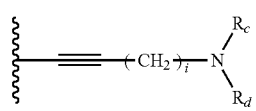

wherein:
i is an integer from 1 to 10,
$R_c$ represents H or a $(C_1-C_6)$alkyl group, and
$R_d$ represents H, a $(C_1-C_6)$alkyl group or a —COOAlk, Alk representing a $(C_1-C_6)$alkyl group; or a group with the following formula (C):

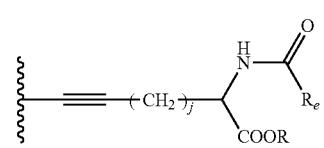

j is an integer from 1 to 10,
$R_d$ represents H, a $(C_1-C_6)$alkyl group, and
$R_e$ represents a $(C_6-C_{10})$aryl group or a $(C_1-C_6)$alkoxy group; or
a group with the following formula (D):

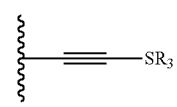

$R_d$ representing a $(C_1-C_6)$alkyl group.

Among the preferred families of compounds with formula (I'), the families made up of the following compounds can be cited:
those with the following formula (I'-1):

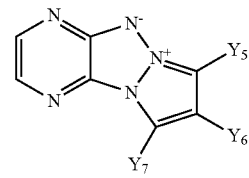

$Y_5$, $Y_6$ and $Y_7$ being as defined above in formula (I'), one of $Y_5$, $Y_6$ and $Y_7$ representing a group with formula -L-Z as defined above; or
those with the following formula (I'-2):

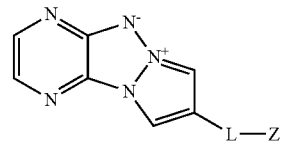

L and Z being as defined above; or
those with the following formula (I'-3):

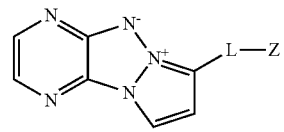

L and Z being as defined above.
According to one embodiment, in formulas (I'), (I'-1), (I'-2) and (I'-3) mentioned above, Z is chosen from the group made up of halogens, carboxylic acids, succinimide esters, tetrafluorophenyl esters, acyl azides, anhydrides, acid halogenides, acrylamides, alcohols, amines, alkynes, aminooxyacetamides, azides, imidoesters, sulfonate esters, halogenoacetamides, alkyl halogenides, sulfonyl halogenides, hydrazines, hydrazides, isocyanates, isothiocyanates, tetrazines and maleimides.

The present invention also relates to a conjugate comprising a biological molecule and a compound with formula (I) as defined above, in which said compound with formula (I) is linked to the biological molecule via a linker, said biological molecule being chosen from the group made up of antibodies, proteins, peptides, carbohydrates, lipids, polysaccharides, fatty acids, amino acids, deoxyribonucleic acids, ribonucleic acids, oligonucleotides, medicinal drugs and ligands (molecules having an affinity for a biological target).

According to the invention, the linker used for the preparation of the conjugates is derived from the -L-Z group defined above for formula (I').

According to one embodiment, the conjugates according to the invention satisfy the following formula (I"):

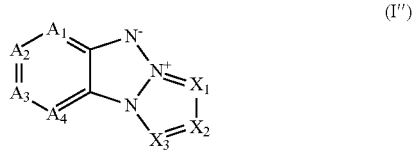

wherein:
A$_1$ is —N— or —C(Y$_1$)—;
A$_2$ is —N— or —C(Y$_2$)—;
A$_3$ is —N— or —C(Y$_3$)—;
A$_4$ is —N— or —C(Y$_4$)—;
at least one of A$_1$, A$_2$, A$_3$ and A$_4$ representing —N—;
Y$_1$, Y$_2$, Y$_3$ and Y$_4$ are chosen independently of one another in the group made up of: H, electro-donor groups and electro-attracting groups, or can represent a group with formula -L'-Z', L' representing a linker and Z' representing a biological molecule chosen from the group made up of antibodies, proteins, peptides, carbohydrates, lipids, polysaccharides, fatty acids, amino acids, deoxyribonucleic acids, ribonucleic acids, oligonucleotides, medicinal drugs and ligands,
where Y$_1$ and Y$_2$ together form, with the carbon atoms that carry them, a (hetero)cycloalkyl group or a (hetero)aryl group comprising from 5 to 30 atoms,
and/or Y$_2$ and Y$_3$ together form, with the carbon atoms that carry them, a (hetero)cycloalkyl group or a (hetero)aryl group comprising from 5 to 30 atoms,
and/or Y$_3$ and Y$_4$ together form, with the carbon atoms that carry them, a (hetero)cycloalkyl group or a (hetero)aryl group comprising from 5 to 30 atoms,
X$_1$ is —N— or —C(Y$_5$)—;
X$_2$ is —N— or —C(Y$_6$)—;
X$_3$ is —N— or —C(Y$_7$)—;
Y$_5$, Y$_6$ and Y$_7$ are chosen independently of one another in the group made up of H, electron-donor groups and electron-attracting groups, or represent a group with formula -L'-Z', L' and Z' being as defined above,
where Y$_5$ and Y$_6$ together form, with the carbon atoms that carry them, a (hetero)cycloalkyl group or a (hetero)aryl group comprising from 5 to 10 atoms,
and/or Y$_6$ and Y$_7$ together form, with the carbon atoms that carry them, a (hetero)cycloalkyl group or a (hetero)aryl group comprising from 5 to 10 atoms, said compound with formula (I") being able to be in salt or pure stereoisomer form or in the form of a mixture of enantiomers and/or diastereoisomers, including racemic mixtures, or in the form of tautomers,
wherein at least one of Y$_1$, Y$_2$, Y$_3$, Y$_4$, Y$_5$, Y$_6$ and Y$_7$ is a group with formula -L'-Z'.

According to the invention, the linker L' is derived from the -L-Z group defined above for formula (I'). Indeed, the compounds with formula (I") are obtained by conjugation between the compounds with formula (I') and a biological molecule, the biological molecule bonding via the reactive Z group defined above.

The conjugates according to the invention are therefore compounds comprising a fluorescent marker, said fluorescent marker being derived from a compound with formula (I) as defined above.

The present invention also relates to the use of the aforementioned conjugates for detecting a biological molecule by fluorescence.

The present invention also relates to the use of the aforementioned fluorescent chromophores in various fields of application, and in particular in the field of biological imaging, fluorescence microscopy, biomolecule marking, fluorescence spectroscopy screening. These compounds can also be used as fluorescent probes.

The present invention also relates to a method for detecting at least one biological molecule in a biological medium, comprising:
  a step for introducing a conjugate according to the invention into said biological medium, said conjugate comprising a fluorescent marker and a biological molecule,
  a step for exciting said medium, and
  a step for detecting at least one fluorescence signal of said fluorescent marker.

In the entire application, the expressions "comprising a" and "including a" mean "comprising at least one" or "including at least one," respectively, unless otherwise specified.

In the entire description above, unless otherwise stated, the term "comprised between x and y" corresponds to an inclusive range, i.e., the values x and y are included in the range.

EXAMPLES

The reactions having to be conducted under anhydrous conditions are done in glassware dried in the oven (T>100° C.), then cooled under an inert argon atmosphere, with solvents that are also anhydrous: acetonitrile, toluene and tetrahydrofuran are dried by passing over a column of a station, dichloromethane is distilled on calcium hydride, triethylamine and 1,4-dioxane are distilled on potassium hydroxide, and the anhydrous DMF kept under sieve is available at ALFA Aesar.

The 1H-pyrazole, 2-iodo-1-nitrobenzene, 4-(3H)-pyrimidinone, (1H)-1,2,3-triazole, 4-nitro-1H-pyrazole, n-BuLi, hydrazine monohydrate, 4-pyrazoleboronic pinacol ester, tert-butyl prop-2-ynylcarbamate, Pd(Ph$_3$)$_2$Cl$_2$, P(PPh$_3$)$_4$, and cesium carbonate are available from ALDRICH.

The 1,2,4(1H)-triazole, D,L-propargylglycine, 3-iodo-1H-pyrazole, phenylacetylene and 1-ethynyl-4-methoxybenzene are available from ACROS.

The 2,3-dichloropyrazine, 2,6-dichloropyrazine, 4-iodo-1H-pyrazole, 4-bromo-1H-pyrazole and N-iodosuccinimide are available from APOLLO Scientific UK.

The 1,2-dichlorobenzene, 3-nitro-1,2,4-(1H)-triazole, 1,3-dithiane, 4-(N,N-dimethylamino)phenylboronic, and potassium carbonate are available from ALFA Aesar.

The various starting indazoles used are available from APOLLO Scientific UK.

I—Reaction Diagrams

Synthesis of the [benzo]-1,3a,6a-triazapentalene Core

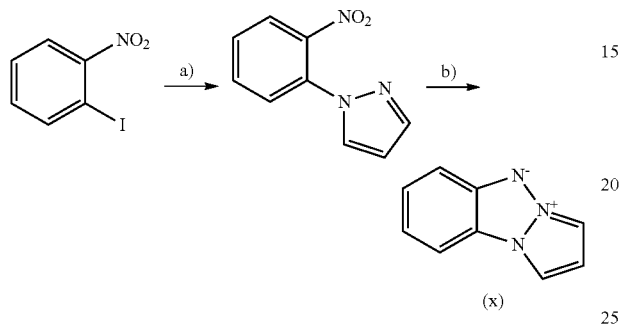

a) pyrazole (1 eq), Cu₂O (0.1 eq), Cs₂CO₃ (2 eq), DMF, 100° C.; b) P(OEt)₃ (22 eq), 176° C., MW.

Synthesis of the [pyrimidino]-1,3a,6a-triazapentalene Core

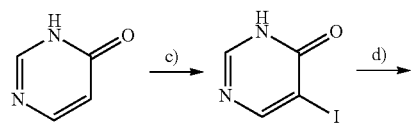

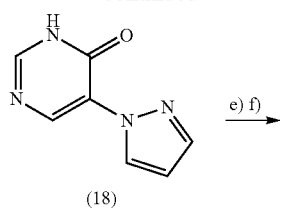

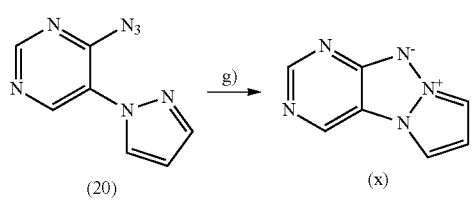

c) NIS (1.1 eq), AcOH, 50° C. d) pyrazole (1.5 eq), Cu₂O (0.05 eq), K₂CO₃ (2 eq), salicylaldoxime (0.2 eq), DMF, 170° C., MW; e) POCl₃ (20 eq), 110° C.; f) NaN₃ (2 eq), DMF; g) 1,2-dichlorobenzene, 165° C.

Synthesis of the [pyrazino]-1,3a,6a-triazapentalene-Type Structures

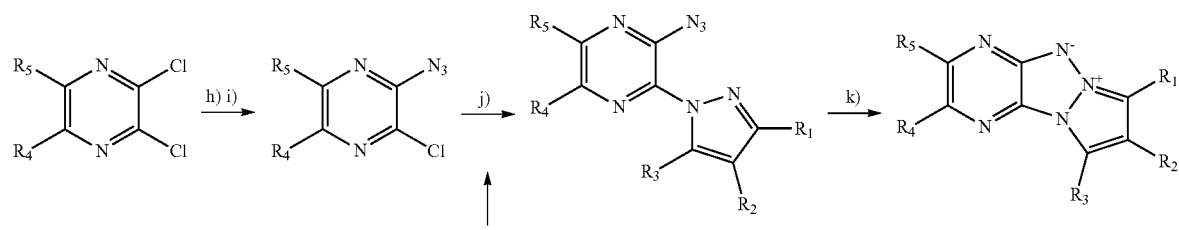

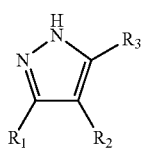

h) N$_2$H$_4$.H$_2$O (2.1 eq); i) NaNO$_2$ (1.1 eq), AcOH/H$_2$O; j) K$_2$CO$_3$ (2 eq), ACN, 82° C.; k) 1,2-dichlorobenzene, 165° C.

Synthesis of the 4-amino-[pyrazino]-1,3a,6a-triaza-pentalene-Type Structures l) 4-DMAP (0.1 eq), toluene; m) Lawesson reagent (0.5 eq), toluene, MW, 140° C.; n) Pyridine (4.5 eq), toluene, MW, 140° C.; o) NaN$_3$ (2.5 eq), DMF, 60° C.; p) 1,2-dichlorobenzene, 165° C.

Synthesis of the 4-amino-[pyrazino]-1,3a,6a-triaza-pentalene-type Structures

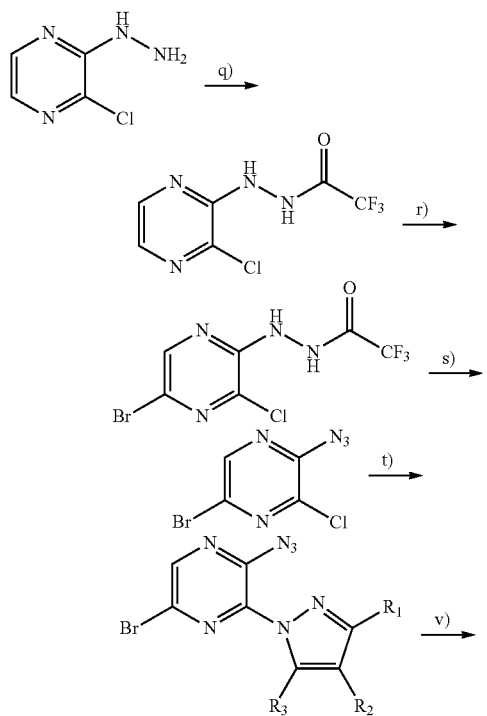

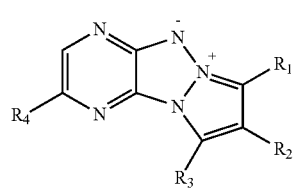

q) TFAA, THF. r) NBS, dichloromethane; s) HCl/EtOH then NaNO$_2$/H$_2$O; f) K$_2$CO$_3$, ACN, reflux; v) 1,2-dichlorobenzene, 165° C.

II—Synthesis of the Intermediaries 1-(2-nitrophenyl)-1H-pyrazole (1)

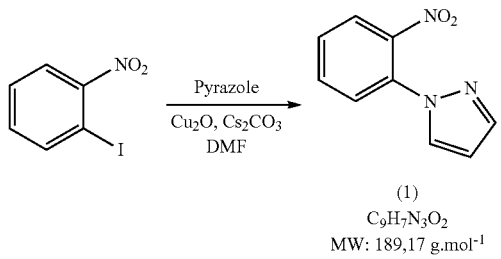 [SMILES: O=[N+]([O-])c1ccccc1I ; O=[N+]([O-])c1ccccc1-n1cccn1]

(1)
C$_9$H$_7$N$_3$O$_2$
MW: 189,17 g.mol$^{-1}$

In a flask placed under argon, the pyrazole (3 g, 0.012 mol, 1 eq.), the 2-iodo-1-nitrobenzene (1.2 g, 0.018 mol, 1.5 eq), the copper oxide (I) (0.17 g, 0.001 mol, 0.1 eq), the Cs$_2$CO$_3$ (7.9 g, 0.024 mol, 2 eq) and the anhydrous DMF (25 mL) are introduced. The obtained suspension is left under agitation at 100° C. for 20 h. After returning to ambient temperature, the reaction medium is concentrated dry. The recovered residue is recovered with ethyl acetate and is washed several times with a saturated sodium chloride solution. The organic phase is dried on MgSO$_4$, filtered and concentrated dry. The raw mixture is purified by silica gel column chromatography (petroleum ether/ethyl acetate: 7/3). A product (1) is obtained with a yield of 75% (1.7 g) in the form of a yellow powder. NMR($^1$H, 250 MHz, chloroform-d) δ 7.88 (dd, J=8.0, 1.5 Hz, 1H), 7.75 (d, J=1.9 Hz, 1H), 7.72 (d, J=2.5 Hz, 1H), 7.67 (dd, J=7.4, 1.4 Hz, 1H), 7.62-7.57 (m, 1H), 7.56-7.47 (m, 1H). NMR($^{13}$C, 400 MHz, chloroform-d) δ 142.74, 133.43, 130.19, 128.80, 126.73, 125.48, 108.63. SM (IC+) m/z 190 (M+H$^+$), 212 (M+Na$^+$).

1-Nitropyrazole (2)

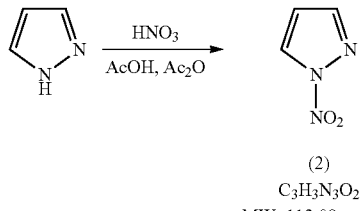

(2)
C$_3$H$_3$N$_3$O$_2$
MW: 113,08 g.mol$^{-1}$

Fuming nitric acid (1.5 mL, 0.036 mol, 1.2 eq) is added dropwise to a suspension of pyrazole (2 g, 0.03 mol, 1 eq) in acetic acid (6 mL) at 0° C. The acetic anhydride (4 mL, 0.041 mol, 1.4 eq) is added last. The reaction mixture is left under agitation for 30 min. is at 0° C., then for 17 h at ambient temperature. The follow-up is done by CCM in petroleum ether/ethyl acetate (7:3). In the medium, 35 m L of cold water is added, the formed precipitate is recovered by filtration and is washed with ice water. The expected product (2) is obtained in the form of a white powder with a yield of 86% (2.9 g). NMR ($^1$H, 250 MHz, DMSO-d6) δ 7.97 (dd, J=3.0, 0.8 Hz, 1H), 7.06 (dd, J=1.7, 0.9 Hz, 1H), 5.88 (dd, J=3.0, 1.7 Hz, 1H).

3-Nitropyrazole (3)

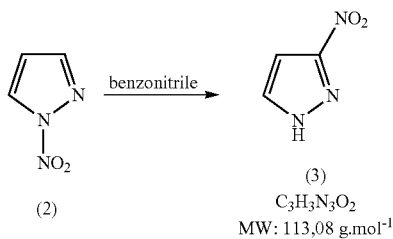

A solution of 1-nitropyrazole (2) (2.9 g, 0.026 mol, 1 eq) in 36 mL of benzonitrile is heated at 180° C. for five hours. After returning to ambient temperature, the heptane (100 mL) is added. The formed white precipitate is recovered by filtration and is rinsed with heptane to yield the product (3) in the form of a white powder with a yield of 58% (1.7 g). NMR ($^1$H, DMSO-d6, 250 MHz): δ 13.14 (1H, s, H), 8.03 (1H, d, $J_1$=2.5 Hz, $H_5$), 7.03 (1H, d, $J_1$=2.5 Hz, $H_4$).

4-(1H)-Nitropyrazole

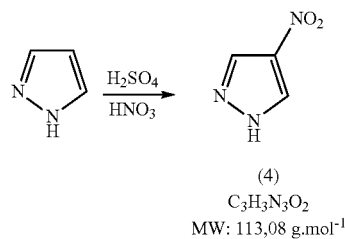

In a flask containing 95% sulfuric acid (22 mL) cooled to 0° C., the pyrazole (3 g, 43.9 mmol, 1 eq) is introduced in small portions. After 5 min. of agitation cold, the temperature of the reaction medium is increased to 55° C. The nitric acid (3.2 mL, 48.3 mmol, 1.1 eq) is next added dropwise while keeping the constant temperature of 55° C. The reaction medium is left under agitation at this temperature for 3 h. After returning to ambient temperature, the reaction medium is basified with solid sodium carbonate and is extracted 3 times with ethyl acetate. The organic phases are gathered, washed with a saturated sodium chloride solution, dried on MgSO$_4$, filtered and concentrated dry. The 4-nitro-(1H)-pyrazole (4) is obtained in the form of a yellow powder with a yield of 89% (4.4 g). NMR ($^1$H, DMSO-d6, 250 MHz): δ 13.91 (se, 1H), 8.54 (se, 2H).

1H-Pyrazol-3(2H)-one (5)

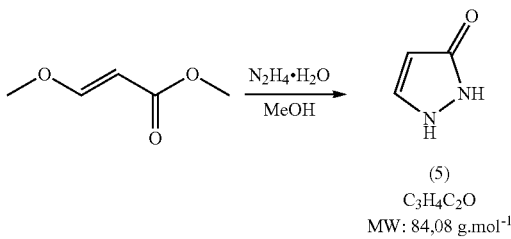

The hydrazine monohydrate (2.7 mL, 55 mmol, 1.1 eq) is added dropwise to a solution of (E)-methoxyacrylate (5.5 mL, 51 mmol, 1 eq) in methanol (5 mL). The obtained mixture is left under reflux agitation of the solvent for 1 h30. The follow-up is done by CCM in dichloromethane/methanol (95:5). After returning to ambient temperature, the reaction medium is concentrated dry to yield the desired product (5) in the form of a yellow powder with a quantitative yield (4.68 g). The product is engaged in the following reaction without purification. NMR ($^1$H, DMSO-d6, 250 MHz) δ 10.30 (s, 1H), 7.34 (d, J=2.2 Hz, 1H), 5.43 (d, J=2.3 Hz, 1H).

1-Acetyl-3-hydroxy-1H-pyrazole (6)

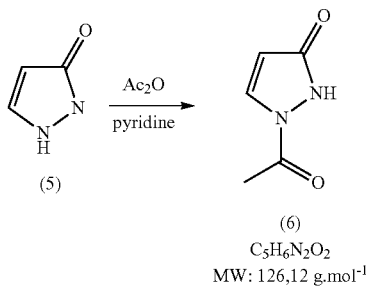

In a solution of 1H-pyrazol-3(2H)-one (5) (4.5 g, 0.05 mol, 1 eq) in the pyridine (22 m L), preheated to 95° C., a mixture of acetic anhydride (5.3 mL, 0.06 mol, 1.1 eq) in the pyridine (11 mL) is added dropwise for 15 min. The obtained solution is left under agitation at 95° C. for 1 h (light yellow to brown coloring of the medium). The follow-up is done by CCM in dichloromethane/methanol (95:5). After returning to ambient temperature, the reaction medium is concentrated dry and is co-evaporated with toluene in order to eliminate the residual pyridine. The obtained precipitate is recovered with ether and left under agitation at ambient temperature for 1 h. After returning to ambient temperature, the reaction medium is concentrated dry to yield the desired product (6) in the form of a yellow powder with a quantitative yield (4.68 g). The product is engaged in the following step without purification on silica column. NMR ($^1$H, DMSO-d6, 250 MHz) δ 10.94 (s, 1H), 8.12 (d, J=3.0 Hz, 1H), 6.00 (d, J=3.0 Hz, 1H), 2.48 (s, 3H).

1-(3-methoxypyrazol-1-yl)ethanone (7)

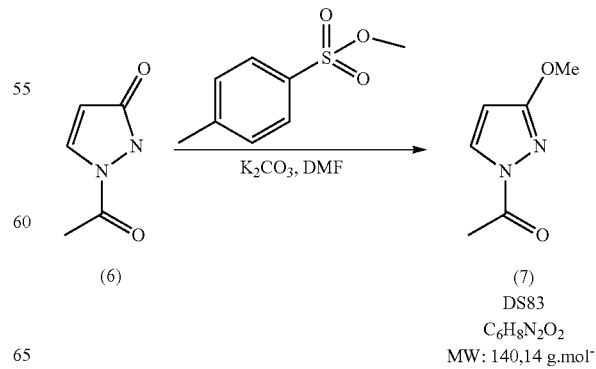

In a flask placed under argon atmosphere, the 1-acetyl-3-hydroxy-1H-pyrazole (6) (300 mg, 2.24 mmol, 1 eq), the potassium carbonate (658 mg, 4.8 mmol, 2 eq) and the anhydrous N,N-dimethylformamide (6 mL) are introduced. The methyl p-toluenesulfonate (444 mg, 2.4 mmol, 1 eq) is added to the mixture last. The reaction medium is left under agitation at ambient temperature and under argon atmosphere for 15 h. The follow-up is done by CCM in ethyl acetate/petroleum ether (7:3). The reaction medium is recovered with ethyl acetate and is washed with water, then with a saturated sodium chloride solution. The organic phase is dried on MgSO$_4$, filtered and concentrated dry to yield the desired product in the form of a yellow oil. The raw compound is next purified on silica column (ethyl acetate/petroleum ether: 1/9; liquid deposition) to yield compound (7) in the form of a colorless oil with a yield of 42% (140 mg). NMR ($^1$H, 250 MHz, Chloroform-d) δ 8.05 (d, J=2.7 Hz, 1H), 5.95 (d, J=2.8 Hz, 1H), 3.95 (s, 3H), 2.59 (s, 3H). NMR ($^{13}$C, 400 MHz, Chloroform-d) δ 169.15, 166.29, 130.42, 99.67, 56.77, 21.90.

3-Methoxy-1H-pyrazole (8)

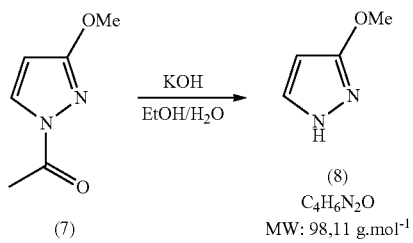

The solid potassium hydroxide (120 mg, 2.14 mmol, 3 eq) is added to a solution of 1-(3-methoxypyrazol-1-yl) ethanone (7) (100 mg, 0.71 mmol, 1 eq) in an ethanol/water mixture (1 mL/0.5 mL). The solution is left under agitation at ambient temperature for 2 h. The follow-up is done by CCM in petroleum ether/ethyl acetate (95:5). The reaction medium is recovered with water and is extracted with ethyl acetate. The aqueous phase is extracted 3 times with the DCM/iPrOH mixture (95/5). The organic phases are gathered, dried on MgSO$_4$, filtered and concentrated dry to yield the product (8) with a yield of 61% (43 mg). NMR ($^1$H, 250 MHz, chloroform-d) δ 9.8 (se, 1H), 7.36 (d, J=1.8 Hz, 1H), 5.73 (d, J=1.8 Hz, 1H), 3.91 (s, 3H). NMR ($^{13}$C, 101 MHz, chloroform-d) δ 164.10, 129.84, 89.63, 55.88.

2-Chloro-3-[1,3]dithian-2-yl-pyrazine (9)

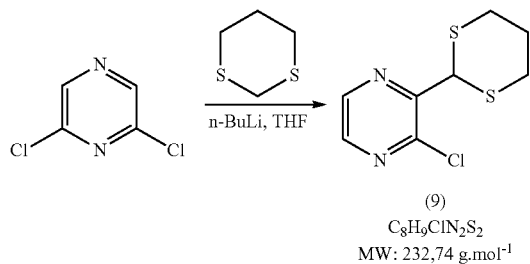

In a dry flask placed under argon atmosphere, the 1,3-diathiane (2.66 g, 22.0 mmol, 1 eq) is solubilized in the anhydrous THF (18 mL). The solution is cooled to −70° C. and a solution of n-BuLi (9.6 mL, 24.0 mmol, 1.2 eq) in hexane at 2.5 M is added slowly. After 30 min. of agitation at −70°, a solution of 2,6-dichloropyrazine (3.0 g, 20.1 mmol, 1.1 eq) in the anhydrous THF (12 mL) is added dropwise. The reaction medium is left under agitation at −78° C. for 1 h. The reaction is stopped while adding water, followed by an extraction with ethyl acetate (3 times). The organic phases are gathered, washed with a solution of saturated sodium chloride, dried on MgSO$_4$ and concentrated dry. The raw residue is purified by silica gel column chromatography (petroleum ether/ethyl acetate: 10/0 and 9/1; solid deposition). The 2-chloro-3-[1,3]dithian-2-yl-pyrazine (9) is obtained with a yield of 82% (3.84 g) and forms a light-yellow powder. NMR ($^1$H, 400 MHz, chloroform-d) δ 8.52 (d, J=2.2 Hz, 1H), 8.32 (d, J=2.1 Hz, 1H), 5.55 (s, 1H), 3.18 (ddd, J=14.0, 6.6, 2.9 Hz, 2H), 3.00 (ddd, J=13.3, 10.0, 2.5 Hz, 2H), 2.30-1.98 (m, 2H). NMR ($^{13}$C, 101 MHz, chloroform-d) δ 153.20 (Cq), 147.15 (Cq), 143.05 (C$_{Ar}$), 142.37 (C$_{Ar}$), 46.81, 30.07, 25.41.

3-Chloro-pyrazine-2-carbaldehyde (10)

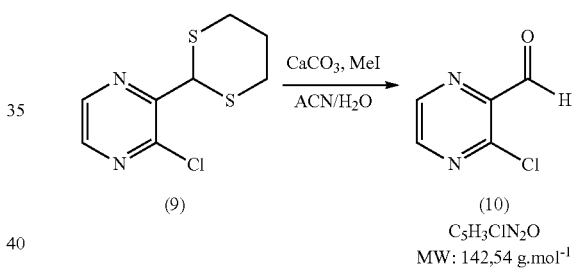

In a flask containing the 2-chloro-3-[1,3]dithian-2-yl-pyrazine (9) (2.1 g, 9.05 mmol, 1 eq) in a mixture of ACN/H$_2$O (135 mL/35 mL), the calcium carbonate (2.72 g, 27.18 mmol, 3 eq) and the methyl iodide (5.6 mL, 27.18 mmol, 10 eq) are introduced. The obtained suspension is left under agitation at 60° C. for 24 h. After returning to ambient temperature, the reaction medium is filtered on Milli-Pore; the filtrate is concentrated dry, recovered with water and extracted with ethyl acetate. The organic phases are gathered, washed with a saturated sodium chloride solution, dried on MgSO$_4$, filtered and concentrated dry. The 3-chloro-pyrazine-2-carbaldehyde (10) is obtained with a quantitative yield (1.5 g) in the form of a red oil. This product is immediately engaged in the following reaction (degradation or polymerization during its conservation and during the purification on silica). NMR ($^1$H, 400 MHz, acetonitrile-d3) δ 10.21 (s, 1H), 8.78 (d, J=2.3 Hz, 1H), 8.61 (d, J=2.3 Hz, 1H). NMR ($^{13}$C, 101 MHz, acetonitrile-d3) δ 190.53, 149.49, 148.38, 145.08, 144.64.

1H-Pyrazolo[3,4-b]pyrazine (11)

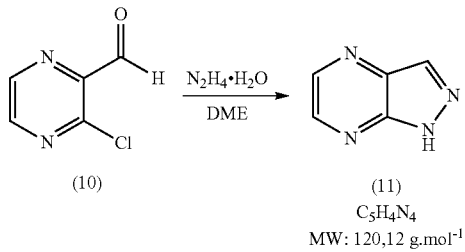

(10)

(11)
C₅H₄N₄
MW: 120,12 g.mol⁻¹

Under argon atmosphere, the hydrazine monohydrate (0.55 mL, 11.2 mmol, 10 eq) is added to a solution of 3-chloro-tyrosine-2-carbaldehyde (10) (155 mg, 1.12 mmol, 1 eq) in the dimethoxyethane (5 mL). The reaction medium is left under reflux agitation of the solvent for 14 h. After returning to ambient temperature, the solvent is evaporated under reduced pressure and the raw residue is re-crystallized in the cyclohexane. The product (11) is obtained with a yield of 97% (1.7 g) in the form of a brown solid. NMR ($^1$H, 400 MHz, Acetone-d6) δ 13.11 (se, 1H), 8.61 (d, J=2.1 Hz, 1H), 8.54 (d, J=2.1 Hz, 1H), 8.34 (s, 1H). NMR ($^{13}$C, 101 MHz, Acetone-d6) δ 143.85, 141.97, 134.86, 134.55. SM (IC+) m/z 121 (M+H⁺), 149 (M+Na⁺).

(3-chloropyrazin-2-yl)hydrazine (12)

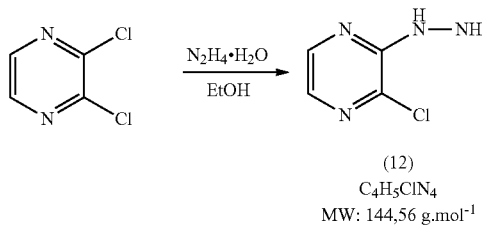

(12)
C₄H₅ClN₄
MW: 144,56 g.mol⁻¹

In a flask containing a solution of 2,3-dichloropyrazine (10.0 g, 65.8 mmol, 1 eq) and ethanol (400 mL), hydrazine monohydrate (6.84 mL, 138.2 mmol, 2.1 eq) is introduced dropwise. The reaction medium is left under reflux agitation of the solvent for 6 h. In order to consume the remaining quantity of 2,3-dichloropyrazine, an additional quantity of hydrazine (1.71 mL, 34.6 mmol, 0.25 eq) is added. After 1× with reflux and return to ambient temperature, the reaction medium is concentrated under reduced pressure. The obtained crystalline solid is recovered with diethylene ether and is filtered on Milli-Pore to yield the desired product (12) in the form of a pale-yellow solid with a quantitative yield (14.9 g). NMR ($^1$H, 250 MHz, chloroform-d) δ 8.03 (dd, J=2.8, 0.4 Hz, 1H), 7.69 (dd, J=2.8, 0.4 Hz, 1H), 6.45 (s, 1H), 3.97 (s, 2H). NMR ($^1$H, 400 MHz, Methanol-d3) δ 8.04 (d, J=2.8 Hz, 1H), 7.58 (dd, J=2.8 Hz, 1H). NMR ($^{13}$C, 400 MHz, Methanol-d3) δ 154.3, 141.9, 134.8, 131.9. SM (IC⁺) m/z 145 (MH⁺).

2-azido-3-chloro-pyrazine (13)

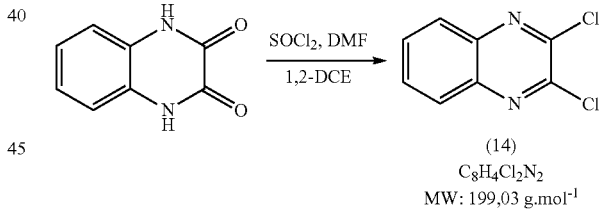

(12)

(13)
C₄H₂ClN₅
MW: 122,55 g.mol⁻¹

The (3-chloropyrazin-2-yl)hydrazine (12) (5 g, 27.6 mmol, 1 eq) is solubilized in an aqueous solution of acetic acid at 10% (100 mL). The reaction medium is cooled to 0° C., then a solution of sodium nitrite (2.1 g, 30 mmol, 1.1 eq) in distilled water (7 mL) is added dropwise. After 30 min. of agitation at 0° C., the reaction medium is extracted with ethyl acetate (×2). The organic phases are gathered and neutralized with a solution of K₂CO₃ at 5%, then washed with a solution saturated with NaCl, dried on MgSO₄ and concentrated dry. The raw residue is next purified by silica gel column chromatography (dichloromethane: 100%, solid deposition) to obtain compound (13) in the form of a pale-yellow powder with a yield of 73% (3.12 g). NMR ($^1$H, 250 MHz, chloroform-d) δ 8.75 (d, J=4.6 Hz, 1H, H₅), 8.13 (d, J=4.6 Hz, 1H, H₆). NMR ($^{13}$C, 400 MHz, chloroform-d) δ144, 13.4, 118.3. SM (IC⁺) m/z 156 (MH⁺), 128 (MH⁺—N₂).

2,3-dichloroquinoxaline (14)

(14)
C₈H₄Cl₂N₂
MW: 199,03 g.mol⁻¹

The N,N-dimethylformamide (50 μL, 0.62 mmol, 0.05 eq) is added to a suspension of quinoxaline-2,3(1H,4H)-dione (2 g, 12.3 mmol, 1 eq) and thionyl chloride (2.25 mL, 31 mmol, 2.5 eq) in 1,2-dichloroethane (20 mL). The reaction medium is left under reflux agitation of the solvent for 2 h. The follow-up is done by CCM in ethyl acetate/petroleum ether (8/2). After returning to ambient temperature, the reaction medium is concentrated dry. The obtained raw residue is recrystallized in an acetonitrile/water mixture (9/1). After returning to ambient temperature, the mixture is cooled to 0° C. and is left at this temperature for 30 min. The formed crystals are recovered by filtration and are washed with cold water. The expected product (14) is obtained in the form of a pale yellow crystalline solid with a yield of 87% (2.1 g). NMR ($^1$H, 250 MHz, 250 MHz, DMSO-d6) δ 8.15-8.02 (m, 2H), 8.00-7.89 (m, 2H).

2-chloro-3-hydrazinylquinoxaline (15)

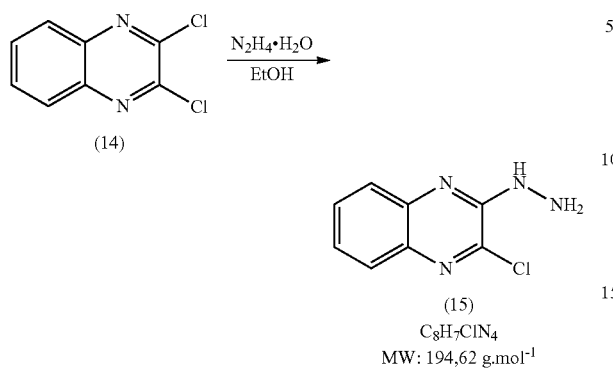

(15)
C$_8$H$_7$ClN$_4$
MW: 194,62 g.mol$^{-1}$

In a flask containing a solution of 2,3-dichloroquinoxaline (14) (500 mg, 2.5 mmol, 1 eq) in ethanol (15 mL), the hydrazine monohydrate (0.25 mL, 5.3 mmol, 2.1 eq) is introduced dropwise. The reaction medium is left under reflux agitation of the solvent for 4 h. After returning to ambient temperature, the formed precipitate is recovered by filtration, washed with cold ethanol and dried under reduced pressure. The raw compound is next purified on silica gel column chromatography (solid deposition, AcOEt/Petroleum Ether: 5/5). The expected product (15) is obtained in the form of an orange powder with a yield of 38% (186 mg). NMR ($^1$H, 250 MHz, Methanol-d4) δ 7.77-7.67 (m, 1H), 7.58 (ddd, J=8.2, 7.0, 1.5 Hz, 1H), 7.39 (ddd, J=8.4, 7.0, 1.4 Hz, 1H). SM (IC+) m/z 165 (MH$^+$—N$_2$H$_3$).

2-azido-3-chloroquinoxaline (16)

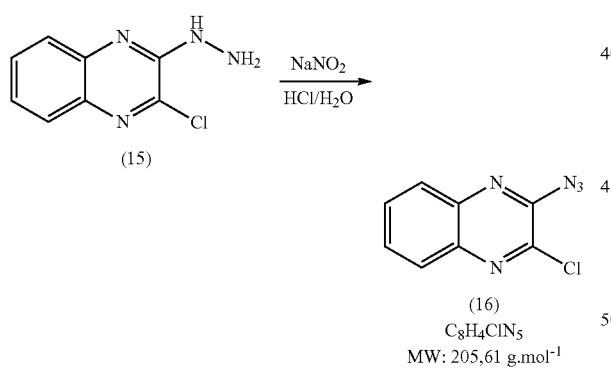

(16)
C$_8$H$_4$ClN$_5$
MW: 205,61 g.mol$^{-1}$

The hydrochloric acid concentrated at 37% (0.26 mL) is added slowly to a suspension of 2-chloro-3-hydrazinylquinoxaline (15) (139 mg, 0.72 mmol, 1 eq) in distilled water (0.6 mL). The obtained solution is cooled to 0° C., then a solution of sodium nitrite (730 mg, 10.6 mmol, 2.6 eq) in distilled water (0.6 mL) is introduced dropwise. After 35 min. of agitation at 0° C. and returning to ambient temperature, the reaction medium is recovered with water and extracted with ethyl acetate (×3). The organic phases are gathered, washed with a solution of sodium bicarbonate and a solution saturated with NaCl, dried on MgSO$_4$, filtered and concentrated dry. The raw compound is purified by silica gel column chromatography (solid deposition, AcOEt/Petroleum Ether: 2/8). The product (16) is obtained in the form of a yellow powder with a yield of 77%. NMR ($^1$H, 400 MHz, chloroform-d) δ 8.63 (dd, J=8.1, 1.2 Hz, 1H), 8.24 (dd, J=8.1, 1.1 Hz, 1H), 7.95 (td, J=7.8, 1.5 Hz, 1H), 7.89 (td, J=7.8, 1.5 Hz, 1H). NMR ($^{13}$C, 101 MHz, chloroform-d) δ 142.28, 140.46, 136.16, 131.84, 130.63, 130.02, 124.79, 116.71.

5-Iodo-3H-pyrimidin-4-one (17)

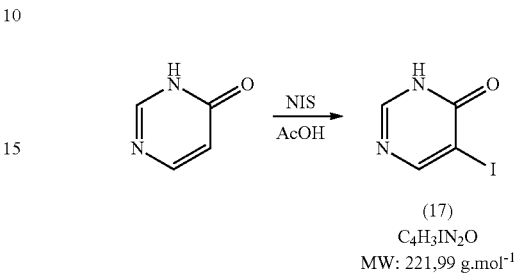

(17)
C$_4$H$_3$IN$_2$O
MW: 221,99 g.mol$^{-1}$

In a dry flask placed under argon atmosphere, containing a solution of 4(3H)-pyrimidinone (750 mg, 7.81 mmol, 1 eq) in glacial acetic acid (27 mL), the N-iodosuccinimide (2.04 g, 8.61 mmol, 1.1 eq) is introduced in small portions. The reaction medium is left under agitation at 50° C. for 4 h. After returning to ambient temperature, the solution is cooled to 0° C. using an ice bath. The formed precipitate is filtered, washed with cold water and rinsed with ethanol. The desired product (17) is obtained in the form of a yellow powder with a yield of 89% (1.74 g). NMR ($^1$H, 400 MHz, DMSO-d6) δ 12.94 (se, 1H), 8.44 (s, 1H), 8.18 (s, 1H). NMR ($^{13}$C, 101 MHz, DMSO-d6) δ 206.76, 160.00, 159.02, 150.23, 90.99. SM (IC+) m/z 223 (M+H$^+$).

5-Pyrazol-1-yl-3H-pyrimidin-4-one (18)

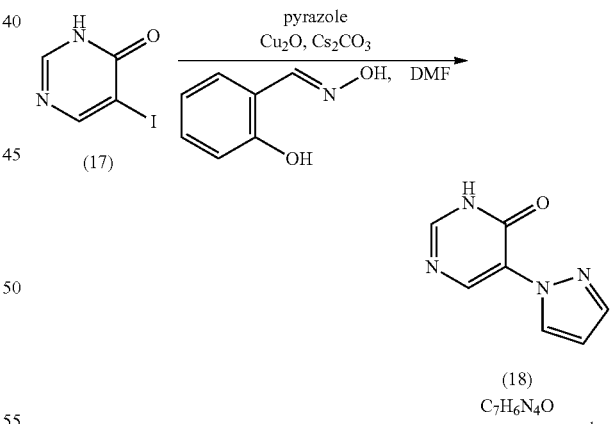

(18)
C$_7$H$_6$N$_4$O
MW: 162,15 g.mol$^{-1}$

In a dry sealed tube placed under argon, the Cu$_2$O (11.2 mg, 0.078 mmol, 0.05 eq), the 2-hydroxybenzaldehyde oxime (42.8 mg, 0.312 mmol, 0.2 eq), the pyrazole (163.5 mg, 2.35 mmol, 1.5 eq), the Cs$_2$CO$_3$ (1.02 g, 3.12 mmol, 2 eq), the 5-Iodopyrimidin-4-ol (17) (350 mg, 1.56 mmol, 1 eq) and the anhydrous N,N-dimethylformamide (1.75 mL) are introduced. The obtained suspension is heated by microwaves at 170° C. for 1 h10. After returning to ambient temperature, the reaction medium is concentrated dry and is purified by silica gel column chromatography (dichloromethane/methanol: 10/0, 97/3, 95/5 and 9/1; solid deposition). The expected product (18) is obtained with a yield of 95% (239 mg) in the form of a pale-yellow powder. NMR ($^1$H, 250 MHz, DMSO-d6) δ 8.59 (d, J=2.4 Hz, 1H), 8.48 (s, 1H), 8.22 (s, 1H), 7.74 (d, J=1.2 Hz, 1H), 6.61-6.38 (m, 1H). NMR ($^{13}$C, 101 MHz, DMSO) δ 147.53, 140.65, 131.16, 106.89. SM (IC+) m/z 163 (M+H$^+$), 185 (M+Na$^+$).

4-Chloro-5-pyrazol-1-yl-pyrimidine (19)

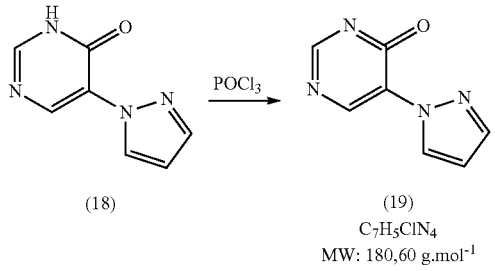

(18) → (19)
C$_7$H$_5$ClN$_4$
MW: 180,60 g.mol$^{-1}$

A solution of 5-yrazol-1-yl-3H-pyrimidin-4-one (18) (53 mg, 0.33 mmol, 1 eq) in phosphoryl trichloride (0.61 mL, 6.54 mmol, 20 eq) is heated at 110° C. for 1 h. After returning to ambient temperature, the reaction mixture is recovered with water and is extracted with ethyl acetate (×2). The organic phases are gathered, washed with a solution de K$_2$CO$_3$ at 5% and with a saturated sodium chloride solution, dried on MgSO$_4$, filtered and concentrated dry. The desired product (19) is obtained with a yield of 93% (55 mg) in the form of a brown solid. This product is engaged directly in the following step (product not very stable). R$_f$ (petroleum ether/ethyl acetate: 7/3): 0.53. NMR ($^1$H, 250 MHz, chloroform-d) δ 9.05 (s, 1H), 8.98 (s, 1H), 8.08 (d, J=2.6 Hz, 1H), 7.84 (d, J=1.7 Hz, 1H), 6.59 (dd, J=2.5, 1.9 Hz, 1H). NMR ($^{13}$C, 63 MHz, chloroform-d) δ 156.31, 154.42, 142.69, 131.13, 108.52. SM (IC+) m/z 181 (MH$^+$).

4-azido-5-(1H-pyrazol-1-yl)pyrimidine (20)

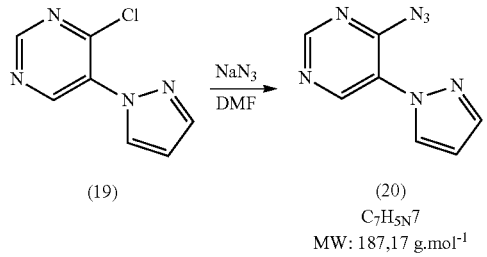

(19) → (20)
C$_7$H$_5$N$_7$
MW: 187,17 g.mol$^{-1}$

In a dry sealed tube under argon atmosphere, containing a solution of 4-chloro-5-pyrazol-1-yl-pyrimidine (19) (100 mg, 0.55 mmol, 1 eq) in anhydrous N,N-dimethylformamide (1.7 mL), the sodium azide (72 mg, 1.11 mmol, 2 eq) is added. The reaction mixture is agitated for 15 h at 50° C. and 2 h at 70° C. After returning to ambient temperature, the raw mixture is recovered with water and is extracted with ethyl acetate (×3). The organic phases are gathered, washed with a solution saturated with sodium chloride, dried on MgSO$_4$ and concentrated dry. The raw residue is purified by silica gel column chromatography (cyclohexane/ethyl acetate: 8/2; solid deposition). The product (20) is obtained with a yield of 22% (23 mg) in the form of a white powder. R$_f$ (petroleum ether/ethyl acetate: 7/3): 0.70. NMR ($^1$H, 250 MHz, chloroform-d) δ 9.58 (s, 1H), 9.21 (d, J=2.7 Hz, 1H), 9.08 (s, 1H), 7.90 (d, J=1.7 Hz, 1H), 6.66 (dd, J=2.7, 1.8 Hz, 1H). SM (IC+) m/z 160 (MH$^+$—N$_2$), 188 (MH$^+$).

N'-(3-chloropyrazin-2-yl)-2,2,2-trifluoroacetohydrazide (75)

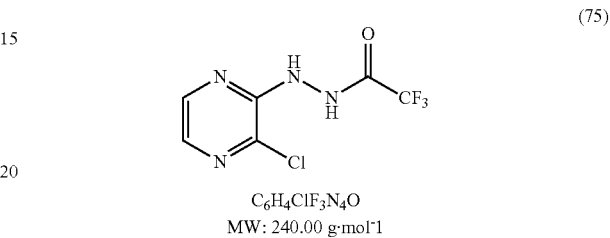

(75)
C$_6$H$_4$ClF$_3$N$_4$O
MW: 240.00 g·mol$^{-1}$

A solution of trifluoroacetic anhydride (4 mL, 29 mmol, 1.3 eq) in 58 mL of anhydrous THF is added to a suspension of (3-chloropyrazin-2-yl)hydrazine (12) (4.8 g, 22 mmol, 1 eq) in 58 mL of anhydrous THF, placed under argon atmosphere and cooled to 0° C. After 2 h of agitation at 0° C., the reaction medium is concentrated. The raw reaction is recovered with water and is extracted with DCM (×3). The organic phases are gathered, dried on MgSO$_4$, and concentrated under reduced pressure. The raw residue is purified on silica gel column by chromatography (Cyclohexane/AcOEt: 8/2; solid deposition). The desired product (75) is obtained with a yield of 86% in the form of a white powder. NMR ($^1$H, 400 MHz, chloroform-d) δ 8.79 (se, 1H), 8.10 (d, J=2.7 Hz, 1H), 7.96 (d, J=2.7 Hz, 1H), 7.37 (se, 1H). NMR ($^{13}$C, 101 MHz, chloroform-d) δ 148.47, 140.18, 135.88, 134.45, 117.27, 114.06. SM (IC$^+$) m/z 241 (MH$^+$).

N'-(5-bromo-3-chloropyrazin-2-yl)-2,2,2-trifluoroacetohydrazide (76)

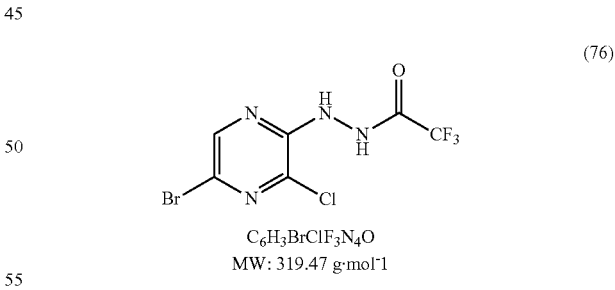

(76)
C$_6$H$_3$BrClF$_3$N$_4$O
MW: 319.47 g·mol$^{-1}$

The N-bromosuccinimide (3.2 g, 17.9 mmol, 1.5 eq) is added in small portions to a suspension of N'-(3-chloropyrazin-2-yl)-2,2,2-trifluoroacetohydrazide (2.9 g, 11.9 mmol, 1 eq) in 100 mL of chloroform, at 0° C. and under argon atmosphere. The obtained suspension is left under agitation at ambient temperature for 24 h. The solvent is next evaporated and the raw residue is purified by silica gel column chromatography (Cyclohexane/AcOEt: 94/6; solid deposition). The product (76) is obtained with a yield of 50% in the form of a yellow powder. NMR ($^1$H, 400 MHz, chloroform-d) δ 8.74 (se, 1H), 8.17 (s, 1H), 7.31 (se, 1H). NMR ($^{13}$C, 101 MHz, chloroform-d) δ 156.07 (q, J=38.4 Hz), 147.84, 142.55, 132.71, 127.55, 115.54 (q, J=250 Hz). SM (IC⁺) m/z 320 (MH⁺).

2-azido-5-bromo-3-chloropyrazine (77)

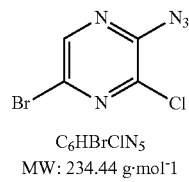

C₆HBrClN₅
MW: 234.44 g·mol⁻¹

The concentrated hydrochloric acid is added dropwise to a suspension of (76) (1 g, 3.1 mmol, 1 eq) in the EtOH (18 mL) The reaction medium is left under reflux agitation overnight (about 18 h). The follow-up is done by CCM in ethyl acetate/petroleum ether (5:5). Once the starting product is consumed, the reaction medium is left to return to ambient temperature and is next cooled to 0° C. Under strong agitation, a solution of NaNO₂ (280 mg, 4.1 mmol, 1.3 eq) in water (1.8 mL) is added dropwise. After 30 min. of agitation at 0° C., the volatile solvents are eliminated by evaporation. The raw reaction is recovered with water and is extracted with AcOEt. The organic phase is washed with a saturated NaCl solution, dried on MgSO₄, then concentrated under reduced pressure. The raw residue is purified on silica gel column by chromatography (Cyclohexane/AcOEt: 80/20; solid deposition). The product (77) is obtained with a yield of 76% in the form of an orange crystalline solid. NMR (¹H, 400 MHz, chloroform-d) δ 8.32 (s, 1H). NMR (¹³C, 101 MHz, chloroform-d) δ 148.50, 143.51, 131.85. SM (IC⁺) m/z 235 (MH⁺), 207 (M-N₂+H⁺).

Synthesis of 2,3-dichloroquinoxaline (78)

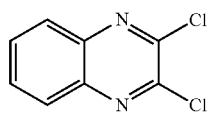

In 100 mL of dichloromethane, 10 g of quinoxaline-2,3-diol (61.67 mmol, 1 eq.) and 11.70 mL of SOCl₂ (160.35 mmol, 2.6 eq.) are dissolved. Added dropwise to this solution are 0.24 mL of DMF (3.08 mmol, 0.05 eq.) and the mixture is brought to reflux for 2 h. Next, the solution is concentrated under vacuum and the residue is next recrystallized in an ACN/water mixture to obtain 10.479 g (52.7 mmol, 85%) of the expected compound.

¹H NMR (250 MHz, Chloroform-d) δ 8.08-7.99 (m, 2H), 7.86-7.77 (m, 2H).

Synthesis of
5,6-dichloropyrazine-2,3-dicarboxylique acid (79)

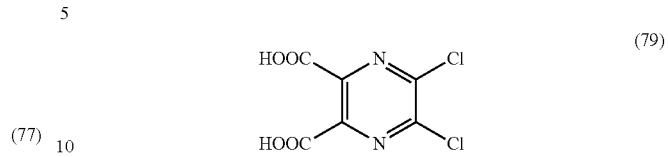

In 150 mL of water, 5 g of 2,3-dichloroquinoxaline (78) (25.12 mmol, 1 eq.) and 25.807 g of KMnO₄ (163.3 mmol, 6.5 eq.) are added. The mixture is brought to reflux for 2 h. After reaction, the hot mixture is filtered to remove the MnO₂. The aqueous phase is acidified with the aqueous HCl. The solution is next concentrated under vacuum and dried. The residue is extracted with acetone, the suspension is filtered on Büchner and the filtrate is concentrated under vacuum to yield 2.005 g of the expected compound (8.46 mmol, 34%).

¹³C NMR (63 MHz, DMSO) δ 163.97, 147.06, 142.66.

Synthesis of 2,3-dichlorofuro[3,4-b]pyrazine-5,7-dione (80)

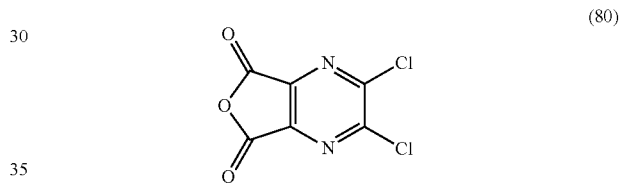

In 30 mL of pure SOCl₂, 2 g of 5,6-dichloropyrazine-2,3-dicarboxylic acid (79) (8.44 mmol) is added. The mixture is brought to reflux for 30 min. The mixture is next concentrated under vacuum to yield the expected product with a quantitative yield.

¹³C NMR (101 MHz, Acetone) δ 158.59, 155.69, 144.33.

Synthesis of 2,3-dichloro-6-propyl-pyrrolo[3,4-b]pyrazine-5,7-dione (81)

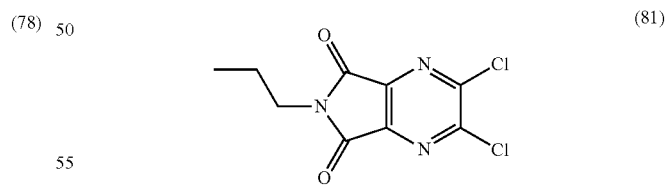

In 20 mL of anhydrous THF under argon, 0.430 g of 2,3-dichlorofuro[3,4-b]pyrazine-5,7-dione (80) (1.96 mmol, 1 eq.) and 0.161 mL of propylamine (1.96 mmol, 1 eq.) are added successively at ambient temperature. The mixture is agitated for one hour, then 0.348 mL of pyridine (4.32 mmol, 2.2 eq.) and 0.25 mL (2.16 mmol, 1.1 eq.) of oxalyl chloride are added to the mixture, which is next brought to reflux for one night. The mixture is dissolved in ethyl acetate and washed with sat NaCl. (2 times). The aqueous phases are re-extracted with EA and the combined organic phases are dried on MgSO₄, filtered and concentrated under vacuum. The residue is dissolved in a minimum of dichloromethane and the product is precipitated by adding petroleum ether. The precipitate is filtered on Büchner and washed with petroleum ether to yield 0.293 g of the expected compound (1.13 mmol, 57%) in the form of a clear beige solid.

¹H NMR (400 MHz, Chloroform-d) δ 3.77 (t, J=7.2 Hz, 2H), 1.75 (h, J=7.6 Hz, 4H), 0.97 (t, J=7.4 Hz, 2H).

¹³C NMR (101 MHz, CDCl₃) δ 162.35, 153.66, 143.78, 40.76, 21.94, 11.39. HRMS (ESI): [M+H]⁺ calculated for C₉H₈Cl₂N₃O₂ 259.998808, measured 259.998893 (0.3 ppm).

Synthesis of benzo[g]quinoxaline-2,3-diol (82)

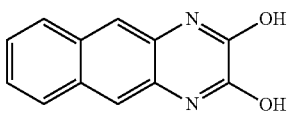

In 10 mL of pure diethyl oxalate, 0.500 g of naphthalene 2,3-diamine (3.16 mmol) is added. The mixture is heated to 110° C. for one night. After cooling, ethanol is added to the mixture. By filtration on Büchner and washing with ethanol, 0.545 g of ochre solid is obtained (2.57 mmol, 81%).

¹H NMR (250 MHz, DMSO-d₆) δ 12.08 (s, 2H), 7.85-7.78 (m, 2H), 7.54 (s, 2H), 7.42-7.35 (m, 2H).

Synthesis of 2,3-dichlorobenzo[g]quinoxaline (83)

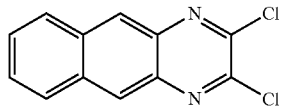

In a flask, 0.677 g of benzo[g]quinoxaline-2,3-diol (82) (3.19 mmol) is dissolved in 20 mL of POCl₃, the solution is brought to reflux for one night. The following day, the mixture is concentrated under reduced pressure and the residue dissolved in dichloromethane and washed with sat NaHCO₃, then sat NaCl. After drying on MgSO₄, filtration and concentration under vacuum, the residue is purified by flash filtration on silica with PE/DCM 1:1 as eluent to obtain 0.229 g of dichloro product (0.92 mmol, 29%) in the form of an ochre solid.

¹H NMR (250 MHz, Chloroform-d) δ 8.57 (s, 2H), 8.11 (m, 2H), 7.64 (m, 2H).

Synthesis of N-prop-2-ynyl-1H-indazole-7-carboxamide (84)

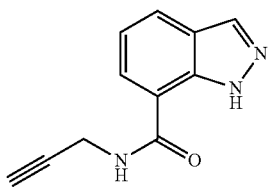

In acetonitrile, 0.200 g of 7-carboxylic indazole acid (1.23 mmol, 1 eq.), 0.237 mm of propargylamine (3.70 mmol, 3 eq.) and 0.515 g of HBTU (1.36 mmol, 1.1 eq.) are successively added. The mixture is agitated for one night at ambient temperature, then the solution is diluted in ethyl acetate and washed with sat NaCl. After drying on MgSO₄, filtration and concentration under reduced pressure, the residue is recovered with dichloromethane and several drops of petroleum ether to form a white precipitate that is filtered on Büchner and washed with petroleum ether to yield a white solid (0.150 g, 0.75 mmol, 61%).

¹H NMR (400 MHz, Acetone-d6) δ 12.38 (s, 1H), 8.38 (s, 1H), 8.13 (s, 1H), 8.01 (dd, J=8.0, 0.9 Hz, 1H), 7.97 (d, J=7.3 Hz, 1H), 7.22 (t, J=7.7 Hz, 1H), 4.29 (dd, J=5.6, 2.4 Hz, 2H), 2.70 (t, J=2.5 Hz, 1H).

¹³C NMR (101 MHz, Acetone) δ 166.82, 134.62, 125.78, 125.26, 120.79, 100.91, 81.33, 72.07.

HRMS (ESI): [M+H]⁺ calculated for C₉H₈Cl₂N₃O₂ 200.081838, measured 200.081715 (0.6 ppm).

Synthesis of 2-methoxy-6-methyl-benzenediazonium tetrafluoroborate (85)

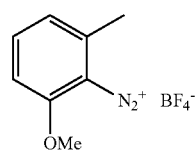

In a flask at 0° C., 1.009 g of 2-methoxy-5-methylaniline (7.35 mmol, 1 eq.) in 8 mL of HBR₄ 50% aq. is added. Added to this solution, dropwise, is 0.608 g of NaNO₂ dissolved in 1 mL of water. The reaction is agitated vigorously for 15 min. at 0° C. and a brown precipitate forms. This precipitate is filtered on Büchner and washed with diethylene ether to yield 1.772 g of the expected disodium salt with a quantitative yield.

¹H NMR (250 MHz, Deuterium Oxide) δ 8.08 (dd, J=8.8, 7.9 Hz, 1H), 7.36 (d, J=8.9 Hz, 1H), 7.28 (d, J=7.8 Hz, 1H), 4.21 (s, 3H), 2.70 (s, 3H).

Synthesis of 7-methoxyindazole (86)

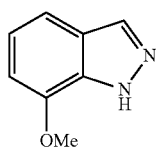

In a flask under argon, 1.750 g of 2-methoxy-6-methyl-benzenediazonium tetrafluoroborate (7.42 mmol, 1 eq.), 0.098 g of 18-6 crown ether (0.37 mmol, 0.05 eq.) activated beforehand and 1,456 g of KOAc (14.83 mmol, 2 eq.) are dissolved in dry chloroform. The mixture is agitated for one night at ambient temperature, then the solution is diluted in dichloromethane and washed with sat NaCl. After drying on MgSO₄, filtration and concentration under vacuum, the residue is purified by flash filtration on silica to provide 0.623 g (4.20 mmol, 57%) in the form of a brown solid.

$^1$H NMR (250 MHz, Chloroform-d) δ 10.52 (s, 1H), 8.05 (s, 0H), 7.34 (dd, J=8.1, 0.7 Hz, 1H), 7.08 (dd, J=8.2, 7.5 Hz, 0H), 6.75 (dd, J=7.5, 0.7 Hz, 1H), 4.00 (s, 3H).

Synthesis of 4-methoxyindazole (87)

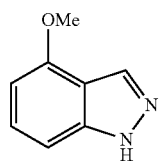

(87)

In 20 mL dioxane, 1.008 g of 2-fluoro-5-methoxy benzaldehyde (6.54 mmol, 1 eq.) and 6.5 mL of hydrazine monohydrate (1 mL/mmol aldehyde) are added. The mixture is heated to reflux for 20 h. After cooling, the mixture is diluted in ethyl acetate and washed with sat NaCl. The organic phase is dried on MgSO$_4$, filtered and concentrated under reduced pressure. The residue is purified by silica chromatography with DCM/MeOH to obtain 0.207 g (1.40 mmol, 21%) of indazole.

$^1$H NMR (400 MHz, Chloroform-d) δ 9.00 (d, J=0.9 Hz, 1H), 7.34 (td, J=8.4, 6.2 Hz, 1H), 6.83-6.70 (m, 2H), 3.90 (s, 3H).

NMR in agreement with the literature Lukin, K.; Hsu, M. C.; Fernando, D.; Leanna, M. R. *J. Org. Chem.* 2006, 71 (21), 8166.

Synthesis of 7-bromo-1H-pyrazolo[3,4-c]pyridine (88)

(88)

In 50 mL of acetic acid, 1 g of 2-bromo-3-amino-4-methyl pyridine (5.35 mmol, 1 eq.) and 0.62 g of potassium acetate (6.95 mmol, 1.3 eq.) are added. Added to this solution at ambient temperature is 0.443 g of sodium nitrite (6.42 mmol, 1.2 eq.) dissolved in 5 mL of water dropwise. After addition, the mixture is heated to 60° C. for one night. Once cooled, the mixture is concentrated under vacuum and the residue is dissolved in ethyl acetate, washed with sat NaHCO$_3$, then sat NaCl. The organic phase is dried on MgSO$_4$, filtered and concentrated under vacuum. The residue is next purified by flash chromatography with PE/EA to yield 0.419 g (2.12 mmol, 40%) of the expected indazole (2.12 mmol, 40%).

$^1$H NMR (250 MHz, Chloroform-d) δ10.48 (bs, 1H), 8.23 (s, 1H), 8.12 (d, J=5.5 Hz, 1H), 7.63 (d, J=5.5 Hz, 1H).

II.1. Synthesis of the Intermediaries by Aromatic Nucleophile Substitution

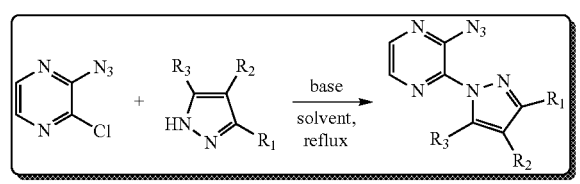

General Procedure A1

In a flask placed under argon atmosphere, the nucleophile (1 eq) is solubilized in anhydrous acetonitrile (concentration comprised between 0.14-0.16M). The potassium carbonate (2 eq) is next introduced. After purging with argon and 10 min. of agitation at ambient temperature, the 2-azido-3-chloropyrazine (13) (1 eq) is introduced in small portions. The obtained suspension is left under reflux agitation of the solvent and under argon atmosphere until total consumption of the 2-azido-3-chloropyrazine (13). The treatment, as well as the purification methods, have been chosen based on the physicochemical characteristics (polarity, solubility, stability, etc.) of each azide.

General treatment: after returning to ambient temperature, the reaction medium is concentrated, the raw residue is recovered with water and is extracted with ethyl acetate. The organic phases are gathered, washed with a solution saturated with sodium chloride, dried on MgSO$_4$, filtered and concentrated under reduced pressure. The raw residue is purified by chromatography on silica gel column.

General Procedure A2

In a flask under argon, 0.3 mmol (1 eq.) of indazole is dissolved in 5 mL of DMF or anhydrous THF. The flask is submerged in an ice bath and 1.1 eq. of NaH (60 wt %) (2.1 eq. if an indazole with an acid function is used) is added to the mixture. The reaction is agitated at 0° C. for 30 min. Next, 1.05 eq. of azido-chloropyrazine dissolved in 1 mL of anhydrous solvent (DMF or THF) is added dropwise. It is left to react for one night while allowing the temperature to rise to the ambient temperature.

2-azido-3-(1H-pyrazol-1-yl)pyrazine (21)

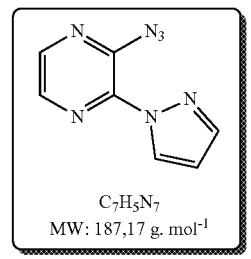

(21)

This compound was prepared according to General procedure A1 with the 1H-pyrazole as nucleophile. The reaction time is 3 h. The follow-up is done by CCM in dichloromethane/ethyl acetate (7:3). After extraction, the desired product (21) is obtained with a yield of 81% (145 mg) in the form of a yellow powder. NMR ($^1$H, 250 MHz, Chloroform-d) δ 9.16 (dd, J=2.8, 0.5 Hz, 1H), 8.68 (d, J=4.5 Hz, 1H), 8.18 (d, J=4.5 Hz, 1H), 8.07 (d, J=1.2 Hz, 1H), 6.70 (dd, J=2.8, 1.6 Hz, 1H). NMR ($^{13}$C, 250 MHz, Chloroform-d) δ 146.47, 132.41, 131.91, 116.77, 111.26. SM (IC+) m/z 188 (MH$^+$), 160 (M-N$_2$+H$^+$).

2-azido-3-(3-nitro-1H-pyrazol-1-yl)pyrazine (22)

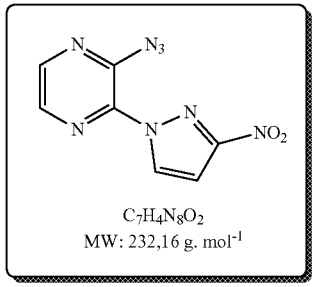

This compound was prepared according to General procedure A1 with the 3-nitro-1H-pyrazole as nucleophile and the anhydrous dichloromethane as solvent. The reaction time is 3 h. The follow-up is done by CCM in dichloromethane/methanol (95/5, R$_4$=0.6). After extraction and purification by chromatography on silica gel column (dichloromethane/methanol: 95/5; solid deposition), the expected product (22) is obtained with a yield of 27% (384 mg) in the form of a yellow powder. NMR ($^1$H, 400 MHz, DMSO-d$_6$) δ 9.57 (d, J=4.6 Hz, 1H), 8.23 (d, J=2.9 Hz, 1H), 8.41 (d, J=4.6 Hz, 1H), 7.51 (d, J=2.9 Hz, 1H). NMR ($^{13}$C, 400 MHz, DMSO-d$_6$) δ 158.5, 140.8, 134.7, 131.4, 120.1, 105.6. SM (IC+) m/z 233 (MH$^+$), 205 (MH$^+$—N$_2$).

2-azido-3-(4-nitro-1H-pyrazol-1-yl)pyrazine (23)

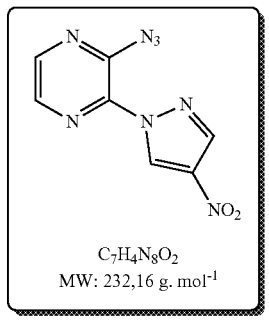

This compound was prepared according to General procedure A1 with the 4-nitro-1H-pyrazole as nucleophile. The reaction time is 4 h. The follow-up is done by CCM in dichloromethane/methanol (95/5, R$_4$=0.45). After extraction, the expected product (23) is obtained with a yield of 76% (840 mg) in the form of a yellow powder. NMR ($^1$H, 250 MHz, DMSO-d$_6$) δ 9.81 (d, J=0.7 Hz, 1H), 9.51 (d, J=4.6 Hz, 1H), 8.82 (d, J=0.7 Hz, 1H), 8.36 (d, J=4.6 Hz, 1H). SM (IC+) m/z 233 (MH$^+$), 205 (MH$^+$—N$_2$).

2-azido-3-(3-methoxy-1H-pyrazol-1-yl)pyrazine (24)

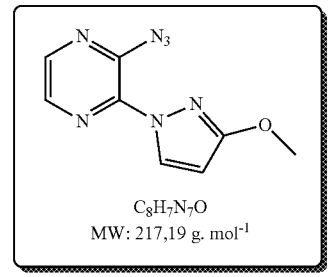

This compound was prepared according to General procedure A1 with the 3-methoxy-1H-pyrazole (8) as nucleophile. The reaction time is 2 h. The follow-up is done by CCM in ethyl acetate/petroleum ether (5:5). After extraction, the expected product (24) is obtained with a yield of 82% (324 mg) in the form of a white powder. NMR ($^1$H, 400 MHz, Chloroform-d$_6$) δ 9.27 (d, J=3.0 Hz, 1H), 8.54 (d, J=4.5 Hz, 1H), 8.15 (d, J=4.5 Hz, 1H), 6.21 (d, J=3.0 Hz, 1H), 4.15 (s, 3H). NMR ($^{13}$C, 400 MHz, Chloroform-d$_6$) δ 135.33, 132.83, 114.90, 100.91, 57.44. SM (IC+) m/z 190 (M-N$_2$+H$^+$), 218 (M+H$^+$), 240 (M+Na$^+$).

2-azido-3-(3-nitro-1H-1,2,4-triazol-1-yl)pyrazine (25)

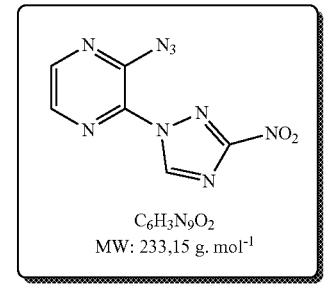

This compound was prepared according to General procedure A1 with the 3-nitro-1H-1,2,4-triazole as nucleophile. The reaction time is 1 h30. The follow-up is done by CCM in dichloromethane/ethyl acetate (7:3). After extraction and purification by chromatography on silica gel column (dichloromethane/ethyl acetate: 7/3; solid deposition), the expected product (25) is obtained with a yield of 93% (140 mg) in the form of a pale-yellow powder. NMR ($^1$H, 400 MHz, chloroform-d) 9.98 (s, 1H), 8.98 (d, J=4.5 Hz, 1H), 8.42 (d, J=4.5 Hz, 1H). NMR ($^{13}$C, 400 MHz, chloroform-d) δ 146.86, 131.35, 118.93. SM (IC+) m/z 206 (M-N$_2$+H$^+$), 234 (M+H$^+$), 256 (M+Na$^+$).

2-azido-3-(1H-1,2,3-triazol-1-yl)pyrazine (26)

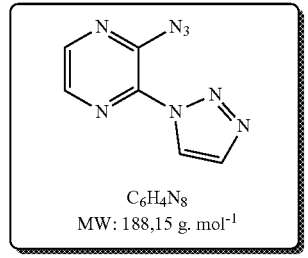

This compound was prepared according to General procedure A1 with the (1H)-1,2,3-triazole as nucleophile. The reaction time is 3 h. The follow-up is done by CCM in dichloromethane/ethyl acetate (7/3, $R_f$=0.59). After extraction, the expected product (26) is obtained with a yield of 95% (170 mg) in the form of a pale-yellow powder. NMR ($^1$H, 400 MHz, chloroform-d) δ 8.83 (d, J=4.5 Hz, 1H), 8.31 (d, J=4.5 Hz, 1H), 8.23 (s, 2H). NMR ($^{13}$C, 400 MHz, chloroform-d) 140.08 (2C), 131.96, 118.47. SM (IC+) m/z 161 (MH$^+$—N$_2$), 189 (MH$^+$), 211 (M+Na$^+$).

2-azido-3-(1H-1,2,4-triazol-1-yl)pyrazine (27)

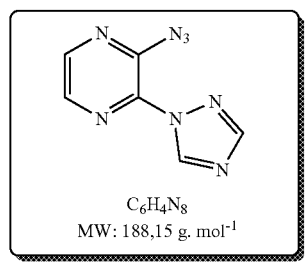

This compound was prepared according to General procedure A1 with the (1H)-1,2,4-triazole as nucleophile. The reaction time is 3 h. The follow-up is done by CCM in dichloromethane/ethyl acetate (8:2). After returning to ambient temperature, the reaction medium is filtered and is rinsed with chloroform. The white solid is recovered in a dichloromethane/water mixture, agitated, and filtered to yield the product (27) with a yield of 81% (1.46 g) in the form of a white powder. NMR ($^1$H, 400 MHz, chloroform-d) δ 9.85 (s, 1H), 8.82 (d, J=4.5 Hz, 1H), 8.39 (s, 1H), 8.28 (d, J=4.5 Hz, 1H). NMR ($^{13}$C, 101 MHz, chloroform-d) δ 154.92, 145.66, 131.81, 117.96. SM (IC+) m/z 189 (MH$^+$), 161 (MH$^+$—N$_2$).

1-(3-azidopyrazin-2-yl)-1H-benzo[d][1,2,3]triazole (28)

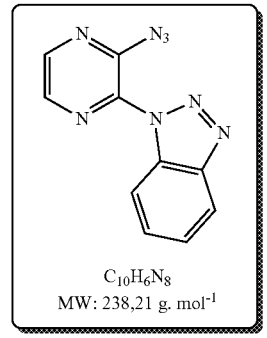

This compound was prepared according to General procedure A1 with the (1H)-1,2,4-triazole as nucleophile. The reaction time is 2 h30. The follow-up is done by CCM in ethyl acetate/petroleum ether (5:5). The reaction mixture is filtered hot (rinsed with hot acetonitrile). The filtrate is concentrated and the obtained solid is triturated in the chloroform/diethyl ether mixture (1/1:v/v). The precipitate is recovered by filtration on Milli-Pore. The expected product (28) is obtained with a yield of 95% (405 mg) in the form of a beige powder. IR (solid): ν (cm$^{-1}$) 3091, 1522, 1481. NMR ($^1$H, 400 MHz, DMSO-d$_6$) δ 9.51 (d, J=4.6 Hz, 1H), 8.57 (dt, J=8.4, 1.0 Hz, 1H), 8.49 (d, J=4.6 Hz, 1H), 8.35 (dt, J=8.3, 1.0 Hz, 1H), 7.85 (ddd, J=8.3, 7.1, 1.1 Hz, 1H), 7.68 (ddd, J=8.2, 7.1, 1.1 Hz, 1H). NMR ($^{13}$C, 101 MHz, DMSO-d$_6$) δ 145.59, 141.86, 139.81, 131.29, 130.25, 126.45, 120.10, 118.90, 114.50. SM (IC+) m/z 211 (MH$^+$—N$_2$), 239 (MH$^+$), 261 (M+Na$^+$);

1-(3-azidopyrazin-2-yl)-1H-indazole (29)

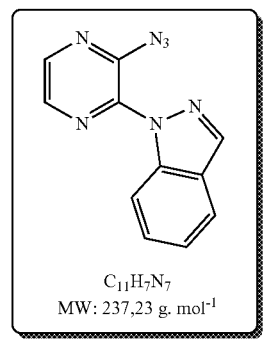

This compound was prepared according to General procedure A1 with the 1,2-benzodiazole as nucleophile. The reaction time is 6 h. After returning to ambient temperature, the reaction medium is filtered on milli-pore. The recovered solid is recovered in a water/acetone mixture (7/3: v/v), is agitated, and the formed precipitate is recovered by filtration on milli-pore. The desired product (29) is obtained with a yield of 80% (855 mg) in the form of a pale-yellow powder. NMR ($^1$H, 400 MHz, DMSO-d6) δ 9.28 (d, J=4.5 Hz, 1H), 8.75 (s, 1H), 8.75 (d, J=8.9 Hz, 1H), 8.33 (d, J=4.6 Hz, 1H), 8.03 (d, J=7.9 Hz, 1H), 7.71 (t, J=8.0 Hz, 1H), 7.49 (t, J=7.6 Hz, 1H). NMR ($^{13}$C, 101 MHz, DMSO-d6) δ 131.24, 129.03, 121.83, 118.19, 118.17, 116.70, 115.17. SM (IC+) m/z 210 (M-N$_2$+H$^+$), 238 (M+H$^+$), 260 (M+Na$^+$).

2-azido-3-(4-(4,4,5,5-tetramethyl-1,3,2-dioxaborolan-2-yl)-1H-pyrazol-1-yl)pyrazine (30)

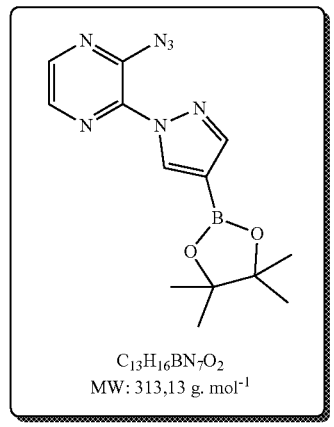

This compound was prepared according to General procedure A1 with the 4-pyrazoleboronic acid pinacol ester as nucleophile. The reaction time is 3 h. The follow-up is done by CCM in dichloromethane/methanol (98:2). The reaction mixture is filtered hot and is rinsed with acetonitrile. The filtrate is concentrated under reduced pressure and the obtained solid is solubilized in several drops of chloroform and is precipitated in the pentane. The precipitate is eliminated by filtration, the filtrate is concentrated and is filtered on silica (dichloromethane/ethyl acetate: 8/2). After several washing operations with pentane, the desired product (30) is obtained with a yield of 87% (210 mg) in the form of a white powder. NMR ($^1$H, 400 MHz, chloroform-d) δ 9.43 (s, 1H), 8.69 (d, J=4.5 Hz, 1H), 8.25 (s, 1H), 8.17 (d, J=4.5 Hz, 1H), 1.37 (s, 12H). NMR ($^{13}$C, 101 MHz, chloroform-d) δ 150.31, 141.66, 138.52, 138.12, 131.62, 116.13, 83.90, 24.67. SM (IC+) m/z 314 (MH$^+$).

2-azido-3-(3,5-dimethyl-4-(4,4,5,5-tetramethyl-1,3,2-dioxaborolan-2-yl)-1H-pyrazol-1-yl)pyrazine (31)

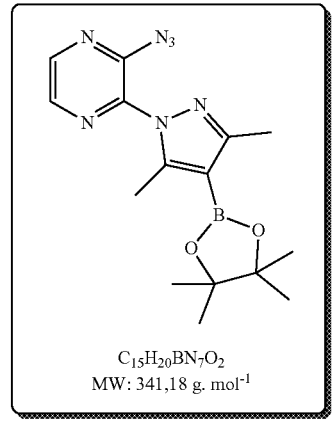

This compound was prepared according to General procedure A1 with the 3,5-dimethyl-4-pyrazoleboronic acid pinacol ester as nucleophile. The reaction time is 3 h. The follow-up is done by CCM in dichloromethane/methanol (98:2). After returning to ambient temperature, the reaction medium is filtered and the filtrate is concentrated. The raw residue is filtered on silica (dichloromethane/ethyl acetate: 8/2). After several washing operations with pentane, the desired product (31) is obtained with a yield of 87% (210 mg) in the form of a white powder. NMR ($^1$H, 400 MHz, chloroform-d) 8.64 (d, J=4.2 Hz, 1H), 8.10 (d, J=4.3 Hz, 1H), 2.83 (s, 3H), 2.53 (s, 3H), 1.34 (s, 12H). NMR ($^{13}$C, 101 MHz, chloroform-d) δ 159.67 (C$_q$), 152.05 (C$_q$), 144.24 (C$_q$), 140.57 (C$_q$), 131.10, 116.26, 83.33 (C$_q$), 25.07, 14.78, 14.47. SM (IC+) m/z 341 (MH$^+$), 313 (M-N$_2$—H$^+$).

2-azido-3-(4-bromo-1H-pyrazol-1-yl)pyrazine (32)

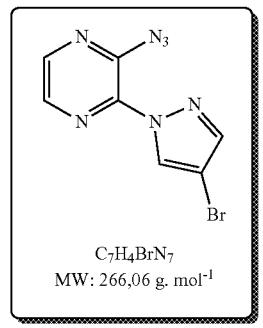

This compound was prepared according to General procedure A1 with the 4-bromo-1H-pyrazole as nucleophile. After 8 h of reflux agitation of the solvent in the medium, an additional quantity of 4-bromo-1H-pyrazole (0.05 eq) is added. The total reaction time is 9 h. The follow-up is done by CCM in petroleum ether/ethyl acetate (6:4). After returning to ambient temperature, the reaction medium is concentrated dry, the obtained residue is recovered with water and is left under agitation at 0° C. for 20 min. The suspension is filtered to yield the desired product (32) with a yield of 96% (3.3 g) in the form of a white powder. NMR ($^1$H, 250 MHz, chloroform-d) δ 9.16 (s, 1H), 8.71 (d, J=4.5 Hz, 1H), 8.17 (d, J=4.5 Hz, 1H), 8.02 (s, 1H). NMR ($^{13}$C, 101 MHz, chloroform-d) δ 146.47, 131.72, 130.93, 116.82, 100.19. SM (IC+) m/z 234 (MH$^+$—N$_2$), 266 (MH$^+$), 288 (MNa$^+$).

2-azido-3-(4-iodo-1H-pyrazol-1-yl)pyrazine (33)

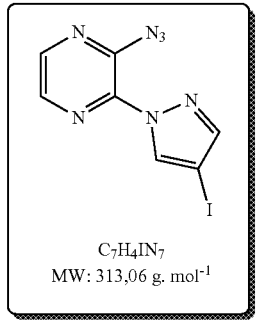

This compound was prepared according to General procedure A1 with the 4-bromo-1H-pyrazole as nucleophile. The reaction time is 2 h. The follow-up is done by CCM in dichloromethane/ethyl acetate (8:2). After returning to ambient temperature, the reaction medium is concentrated dry, the residue is recovered with distilled water and is left under agitation at 0° C. for 20 min. The suspension is filtered and is rinsed in acetonitrile to obtain the desired product (33) with a yield of 93% (2.8 g) in the form of a white powder. NMR ($^1$H, 250 MHz, DMSO-d6) δ 9.35 (d, J=4.6 Hz, 1H), 9.13 (s, 1H), 8.26 (d, J=4.6 Hz, 1H), 8.19 (s, 1H). NMR ($^{13}$C, 400 MHz, DMSO-d6) δ 149.21, 140.62, 139.20, 134.98, 131.50, 118.53, 64.59. SM (IC+) m/z 286 (MH$^+$—N$_2$), 314 (MH$^+$), 335 (MNa$^+$).

1-(3-azidopyrazin-2-yl)-1H-pyrazolo[3,4-b]pyrazine and 2-(3-azido pyrazin-2-yl)-2H-pyrazolo[3,4-b]pyrazine (34.1 and 34.2)

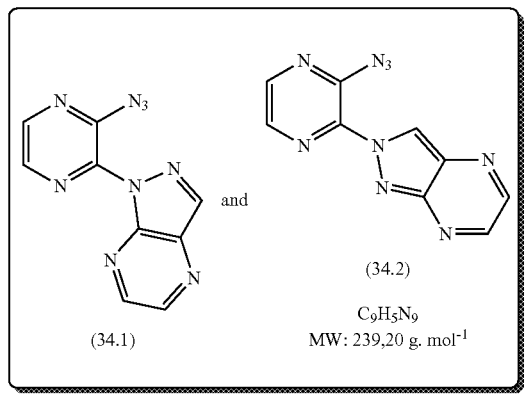

These compounds were prepared according to General procedure A1 with the 1H-pyrazolo[3,4-b]pyrazine as nucleophile. The reaction time is 3 h. The follow-up is done by CCM in dichloromethane/methanol (97:3). After returning to ambient temperature, the reaction medium is concentrated dry, the residue is recovered with distilled water and is left under agitation at 0° C. for 20 min. The suspension is filtered to yield the mixture of two isomers (34.1) and (34.2) with a ratio of 1:0.66 (obtained by NMR). The mixture of two products is engaged in the following reaction without additional purification. (34.1): NMR ($^1$H, 250 MHz, DMSO-d6) δ 9.46 (d, J=4.6 Hz, 1H), 9.06 (s, 1H), 8.88 (d, J=2.3 Hz, 1H), 8.82 (d, J=2.3 Hz, 1H), 8.41 (d, J=4.6 Hz, 1H). (34.2): NMR ($^1$H, 250 MHz, DMSO-d6) 9.91 (s, 1H), 9.57 (d, J=4.6 Hz, 1H), 8.84 (d, J=1.7 Hz, 1H), 8.76 (d, J=1.4 Hz, 1H), 8.45 (d, J=4.6 Hz, 1H). (34.1) and (34.2): SM (IC+) m/z 212 (M-N$_2$+H$^+$), 240 (MH$^+$), 262 (MNa$^+$).

2-azido-3-(1H-pyrazol-1-yl)quinoxaline (35)

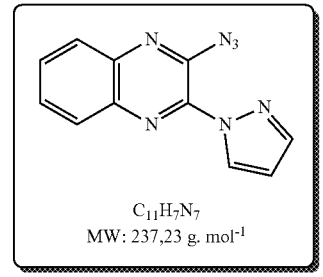

In a flask placed under argon atmosphere, the pyrazole (23 mg, 0.34 mmol, 1 eq), the cesium carbonate (196 mg, 0.6 mmol, 2 eq) and the anhydrous dichloromethane (5 mL) are introduced. In the obtained suspension, a solution of 2-azido-3-chloroquinoxaline (16) (64 mg, 0.3 mmol, 1 eq) in the anhydrous dichloromethane (3 mL) is added dropwise. The reaction medium is left under agitation at ambient temperature for 5 min and 6 h with solvent reflux. The follow-up is done by CCM in ethyl acetate/petroleum ether (7:3). After returning to ambient temperature, the medium is recovered with water and is extracted 3 times with dichloromethane. The organic phases are gathered, dried on MgSO$_4$, filtered and concentrated dry. The raw mixture is purified by silica gel column chromatography (petroleum ether/ethyl acetate: 7/3; solid deposition). The expected product (35) is obtained with a yield of 85% (61 mg) in the form of a yellow powder. NMR ($^1$H, 400 MHz, chloroform-d) δ 9.30 (d, J=2.8 Hz, 1H), 8.72-8.59 (m, 1H), 8.31 (dd, J=6.4, 3.1 Hz, 1H), 8.08 (d, J=2.8 Hz, 1H), 7.86 (dd, J=6.2, 3.4 Hz, 2H), 6.72 (dd, J=2.7, 1.6 Hz, 1H). NMR ($^{13}$C, 101 MHz, chloroform-d) δ 145.63, 139.02, 138.30, 135.49, 131.69, 130.62, 130.43, 129.90, 124.37, 116.55, 110.43. SM (IC+) m/z 210 (M+H$^+$—N$_2$), 238 (M+H$^+$), 260 (M+Na$^+$), 497 (2M+Na$^+$).

2-azido-3-(4-methoxy-1H-pyrazol-1-yl)pyrazine (89)

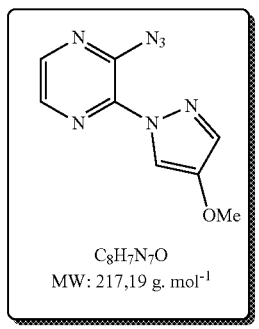

This compound was prepared according to General procedure A1 with the 4-methoxy-1H-pyrazole (prepared according to the method described in WO2014/008197) as nucleophile. The reaction time is 18 h. After returning to ambient temperature, the reaction medium is concentrated dry and is engaged without purification in the following step. SM (IC+) m/z 190 (M-$N_2$+$H^+$), 218 (M+$H^+$), 240 (M+$Na^+$).

2-azido-3-(3-iodo-1H-pyrazol-1-yl)pyrazine (90)

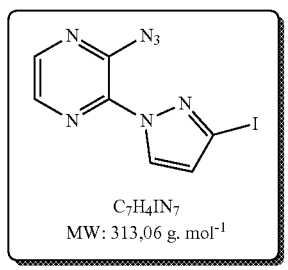

This compound was prepared according to General procedure A1 with the 3-iodo-1H-pyrazole (800 mg, 4.1 mmol, 1 eq) as nucleophile. The reaction time is 1 h45. After returning to ambient temperature, the reaction medium is concentrated dry and is engaged without purification in the following step. NMR ($^1$H, 250 MHz, chloroform-d) δ 9.17 (d, J=2.8 Hz, 1H), 8.69 (d, J=4.5 Hz, 1H), 8.21 (d, J=4.6 Hz, 1H), 6.86 (d, J=2.8 Hz, 1H).

1-(3-azidopyrazin-2-yl)-4,5,6,7-tetrahydro-1H-indazole (91)

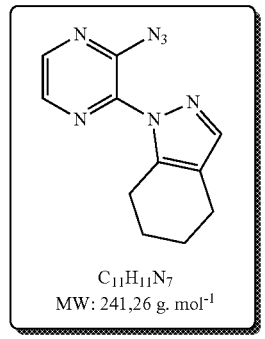

This compound was prepared according to General procedure A1 with the 4,5,6,7-tetrahydro-1H-indazole (230 mg, 1.9 mmol, 1 eq) as nucleophile. The reaction time is 4 h. After returning to ambient temperature, the reaction medium is concentrated dry and is engaged without purification in the following step. SM (IC+) m/z 214 (M-$N_2$+$H^+$), 242 (M+$H^+$).

1-(3-azidopyrazin-2-yl)-4-nitro-1H-indazole (92)

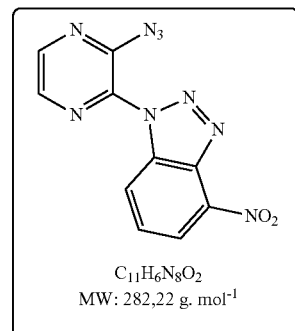

This compound was prepared according to General procedure A1 with the 4-nitroindazole as nucleophile. The reaction time is 3 h. After returning to ambient temperature, the reaction medium is concentrated dry and is engaged without purification in the following step.

1-(3-azidopyrazin-2-yl)-5-nitro-1H-indazole (93)

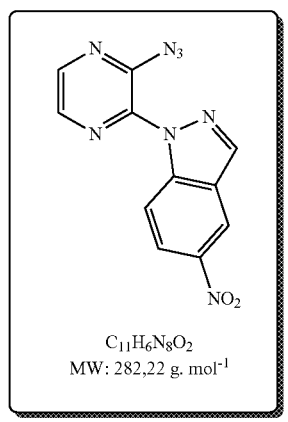
(93)

C₁₁H₆N₈O₂
MW: 282,22 g. mol⁻¹

This compound was prepared according to General procedure A1 with the 5-nitroindazole as nucleophile. The reaction time is 20 h. After returning to ambient temperature, the reaction medium is concentrated dry and is engaged without purification in the following step.

1-(3-azidopyrazin-2-yl)-6-nitro-1H-indazole (94)

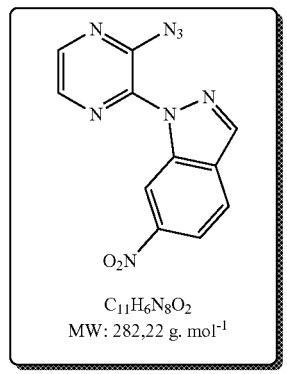
(94)

C₁₁H₆N₈O₂
MW: 282,22 g. mol⁻¹

This compound was prepared according to General procedure A1 with the 6-nitroindazole as nucleophile. The reaction time is 22 h. After returning to ambient temperature, the reaction medium is concentrated dry and is engaged without purification in the following step.

2-(3-azidopyrazin-2-yl)-7-nitro-2H-indazole (95)

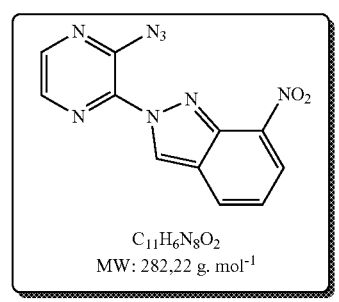
(95)

C₁₁H₆N₈O₂
MW: 282,22 g. mol⁻¹

This compound was prepared according to General procedure A1 with the 7-nitroindazole as nucleophile. The reaction time is 18 h. After returning to ambient temperature, the reaction medium is concentrated dry and is engaged without purification in the following step.

1-(3-azidopyrazin-2-yl)-1H-indazole (96)

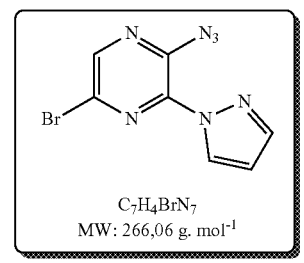
(96)

C₇H₄BrN₇
MW: 266,06 g. mol⁻¹

This compound was prepared according to General procedure A1 with the 1H-pyrazole as nucleophile and compound (77) as halogen derivative. The reaction time is 12 h. After returning to ambient temperature, the reaction medium is concentrated dry and is engaged without purification in the following step. NMR (¹H, 400 MHz, chloroform-d) δ 9.00 (d, J=2.9 Hz, 1H), 8.79 (s, 1H), 8.07 (d, J=1.6 Hz, 1H), 6.68 (dd, J=2.9, 1.6 Hz, 1H). SM (IC+) m/z 239 (M-N₂+H⁺), 267 (MH⁺).

2-azido-5-bromo-3-(1H-1,2,4-triazol-1-yl)pyrazine (97)

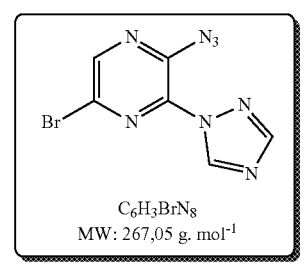
(97)

C₆H₃BrN₈
MW: 267,05 g. mol⁻¹

This compound was prepared according to General procedure A1 with the (1H)-1,2,4-triazole as nucleophile and compound (77) as halogen derivative. The reaction time is 16 h. After returning to ambient temperature, the reaction medium is concentrated dry and is engaged without purification in the following step. NMR ($^1$H, 400 MHz, chloroform-d) δ 9.76 (s, 1H), 8.97 (s, 1H), 8.47 (s, 1H). SM (IC+) m/z 240 (M-$N_2$+$H^+$), 268 ($MH^+$).

2-azido-3-(4-bromo-3,5-dimethyl-pyrazol-1-yl)pyrazine (98)

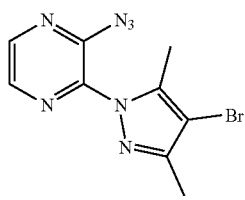

Synthesized according to method A1 from 0.200 g of 2-azido-3-chloro-pyrazine (1.29 mmol, 1 eq.), 0.248 g of 4-bromo-3,5-dimethyl-1H-pyrazole (1.41 mmol, 1.1 eq.) and 0.355 g of $K_2CO_3$ (2.57 mmol, 2 eq.). The residue is next dissolved in a minimum of dichloromethane and the desired product is precipitated by adding petroleum ether. The precipitate is next filtered on Büchner and washed with petroleum ether to yield 0.286 g (0.97 mmol, 76%) of the expected product in the form of a pale-yellow powder.

$^1$H NMR (250 MHz, Chloroform-d) δ 8.67 (d, J=4.5 Hz, 1H), 8.09 (d, J=4.5 Hz, 1H), 2.70 (s, 3H), 2.44 (s, 3H). $^{13}$C NMR (63 MHz, $CDCl_3$) δ 152.67, 143.82, 141.36, 140.09, 130.94, 116.50, 102.75, 13.88, 13.16. HRMS (ESI): $[M+H]^+$ calculated for $C_9H_9BrN_7$ 294.009732, measured 294.009714 (0.1 ppm), $[M-N_2+H]^+$ $C_9H_9BrN_5$ calculated 266.003584, measured 266.003493 (−0.6 ppm).

3-chloro-6-propyl-2-pyrazol-1-yl-pyrrolo[3,4-b]pyrazine-5,7-dione (99)

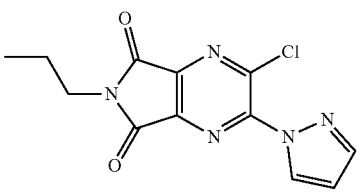

Synthesized according to method A1 from 0.206 g of 2,3-dichloro-6-propyl-pyrrolo[3,4-b]pyrazine-5,7-dione (0.79 mmol, 1 eq.), 0.070 g of pyrazole (1.03 mmol, 1.3 eq.) and 0.142 g of $K_2CO_3$ (1.03 mmol, 1.3 eq.). The residue is next purified by chromatography on silica gel to yield 0.080 g of the desired product (0.27 mmol, 35%).

$^1$H NMR (250 MHz, Chloroform-d) δ 8.49 (dd, J=2.8, 0.7 Hz, 1H), 7.94 (dd, J=1.7, 0.7 Hz, 1H), 6.62 (dd, J=2.8, 1.7 Hz, 1H), 3.83-3.73 (m, 2H), 1.86-1.68 (m, 2H), 0.98 (t, J=7.4 Hz, 3H). $^{13}$C NMR (101 MHz, $CDCl_3$) δ 162.93, 162.55, 148.43, 146.12, 144.57, 142.95, 142.73, 131.82, 109.93, 40.67, 21.98, 11.40. HRMS (ESI): $[M+H]^+$ calculated for $C_{12}H_{11}ClN_5O_2$ 292.059579, measured 292.059488 (0.3 ppm).

3-chloro-2-pyrazol-1-yl-benzo[g]quinoxaline (100)

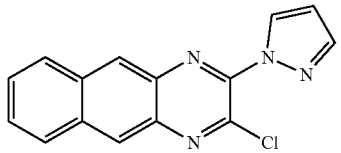

Prepared according to method A1 from 0.118 g of 2,3-dichlorobenzo[g]quinoxaline (0.47 mmol, 1 eq.), 0.042 g of pyrazole (0.62 mmol, 1.3 eq.) and 0.131 g of $K_2CO_3$ (0.95 mmol, 2 eq.). The mixture is brought to reflux by microwaves for 2 h and extracted with ethyl acetate. The residue is purified by chromatography on PE/EA silica to yield 0.069 g of the desired product (0.25 mmol, 52%).

$^1$H NMR (400 MHz, Chloroform-d) δ 8.66 (s, 1H), 8.64 (s, 1H), 8.41 (d, J=2.6 Hz, 1H), 8.12 (ddd, J=9.3, 6.0, 2.9 Hz, 2H), 7.94 (d, J=1.7 Hz, 1H), 7.64 (dd, J=6.5, 3.2 Hz, 2H), 6.61 (dd, J=2.7, 1.7 Hz, 1H).

$^{13}$C NMR (101 MHz, $CDCl_3$) δ 143.13, 142.58, 141.18, 137.37, 135.71, 134.51, 134.35, 131.27, 128.65, 128.54, 127.66, 127.40, 126.76, 108.38. HRMS (ESI): $[M+H]^+$ calculated for $C_{15}H_{10}ClN_4$ 281.058850, measured 281.058480 (1.3 ppm).

2-(3-azidopyrazin-2-yl)indazole-7-sodium carboxylate (101)

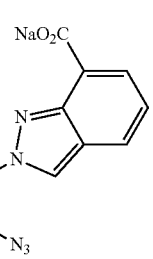

Synthesized according to method A2 from 0.100 g of indazole-7-carboxylique acid (0.62 mmol, 1 eq.), 0.101 g azido-chloropyrazine (0.65 mmol, 1.05 eq.), 0.052 g of NaH (60 wt %) (1.30 mmol, 2.1 eq.). Direct precipitation by adding ethyl acetate and Büchner filtration. Obtained mass: 0.202 g, quantitative.

$^1$H NMR (400 MHz, DMSO-d6) δ 13.05 (s, 1H), 9.92 (s, 1H), 9.56 (d, J=4.4 Hz, 1H), 8.47 (d, J=4.5 Hz, 1H), 8.22 (d, J=8.5 Hz, 1H), 8.09 (dd, J=6.9, 1.1 Hz, 1H), 7.31 (dd, J=8.5, 6.9 Hz, 1H). HRMS (ESI): $[M+H]^+$ calculated for $C_{12}H_8N_7O_2$ 282.073399, measured 282.073194 (0.7 ppm).

1-(3-azidopyrazin-2-yl)indazole-5-sodium sulfonate (102)

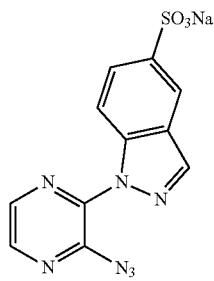

Synthesized according to method A2 from 0.127 g of indazole-sulfonic acid (0.64 mmol, 1 eq.), 0.100 g of pyrazine (0.64 mmol, 1 eq.), 0.054 g of NaH, 1.35 mmol, 2.1 eq.) Direct precipitation by adding ethyl acetate and Büchner filtration. Quantitative, used as is for following reaction.

$^1$H NMR (250 MHz, DMSO-d6) δ 9.27 (d, J=4.6 Hz, 1H), 8.78 (d, J=0.8 Hz, 1H), 8.67 (dt, J=8.8, 0.8 Hz, 1H), 8.33 (d, J=4.6 Hz, 1H), 8.21 (dd, J=1.6, 0.8 Hz, 1H), 7.94 (dd, J=8.8, 1.6 Hz, 1H). HRMS (ESI): [M]$^-$ calculated for $C_{11}H_6N_7O_3S$ 316.025832, measured 316.025876 (−0.5 ppm).

2-(3-azidopyrazin-2-yl)-7-bromo-indazole (103)

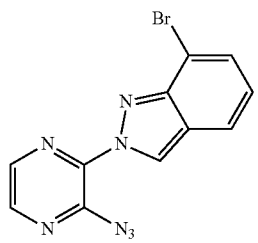

Synthesized according to method A2 from 0.905 g (0.46 mmol, 1 eq.) of 7-bromoindazole, 0.020 g (0.51 mmol, 1.1 eq.) of NaH (60 wt %), 0.075 g (0.48 mmol, 1.05 eq.) of azido-chloropyrazine. Product precipitated by adding 1 mL of water and ethyl acetate to the mixture, filtered on Büchner. Obtained mass 0.133 g (0.42 mmol, 92%).

$^1$H NMR (400 MHz, DMSO-d6) δ 9.88 (s, 1H), 9.54 (d, J=4.5 Hz, 1H), 8.46 (d, J=4.6 Hz, 1H), 7.96 (dd, J=8.6, 0.9 Hz, 1H), 7.73 (dd, J=7.1, 0.8 Hz, 1H), 7.11 (dd, J=8.5, 7.1 Hz, 1H). $^{13}$C NMR (101 MHz, DMSO) δ 148.91, 141.90, 139.92, 131.69, 131.62, 127.59, 124.43, 123.20, 121.78, 119.72, 111.03.

HRMS (ESI): [M+H]$^+$ calculated for $C_{11}H_7BrN_7$ 315.994082, measured 315.994348 (0.8 ppm).

2-(3-azidopyrazin-2-yl)-N-prop-2-ynyl-indazole-7-carboxamide (104)

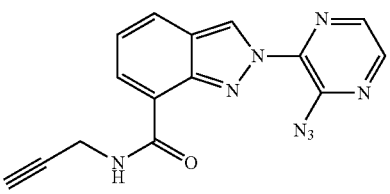

Synthesized according to method A2 from 0.060 g (0.30 mmol, 1 eq.) of N-prop-2-ynyl-1H-indazole-7-carboxamide, 0.25 g (0.63 mmol, 2.1 eq.) of NaH (60 wt %), 0.049 g (0.0.32 mmol, 1.05 eq.) of azido-chloropyrazine. The product is precipitated by adding water and ethyl acetate and is next filtered on Büchner and washed with ethyl acetate to obtain 0.033 g (0.104 mmol, 35%) of indazolo-azido pyrazine.

$^1$H NMR (250 MHz, DMSO-d6) δ 9.82 (s, 1H), 9.76 (t, J=5.5 Hz, 1H), 9.55 (d, J=4.6 Hz, 1H), 8.46 (d, J=4.6 Hz, 1H), 8.23-8.14 (m, 2H), 7.39 (dd, J=8.5, 6.9 Hz, 1H), 4.35 (dd, J=5.6, 2.5 Hz, 2H), 3.20 (t, J=2.55 Hz, 1H). HRMS (ESI): [M+H]$^+$ calculated for $C_{15}H_{11}N_8O$ 319.105033, measured 319.105287 (0.8 ppm).

2-(3-azidopyrazin-2-yl)-7-methoxy-indazole (105)

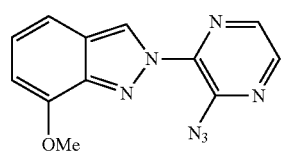

Synthesized according to method A2 from 0.100 g (0.67 mmol, 1 eq.) of 7-methoxyindazole (86), 0.030 g (0.74 mmol, 1.1 eq.) of NaH (60 wt %), 0.110 g (0.71 mmol, 1.05 eq.) of azido-chloropyrazine. The product is precipitated by adding water and ethyl acetate and is next filtered on Büchner and washed with ethyl acetate to obtain 0.126 g (0.47 mmol, 70%) of indazolo-azido pyrazine.

$^1$H NMR (250 MHz, Chloroform-d) δ 9.74 (s, 1H), 8.76 (d, J=4.5 Hz, 1H), 8.31 (d, J=4.5 Hz, 1H), 7.34-7.27 (m, 1H), 7.08 (dd, J=8.6, 7.2 Hz, 1H), 6.60 (d, J=7.2 Hz, 1H), 4.04 (s, 3H). HRMS (ESI): [M+H]$^+$ calculated for $C_{12}H_{10}N_7O$ 268.094134, measured 268.093999 (−0.5 ppm).

1-(3-azidopyrazin-2-yl)-4-methoxy-indazole (106)

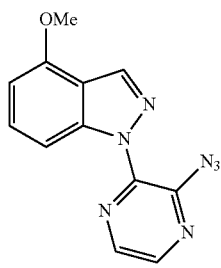

Synthesized according to method A2 from 0.098 g (0.66 mmol, 1 eq.) of 4-methoxyindazole (87), 0.029 g (0.74 mmol, 1.1 eq.) of NaH (60 wt %), 0.103 g (0.66 mmol, 1 eq.) of azido-chloropyrazine. The product is next precipitated by adding water and ethyl acetate and is next filtered on Büchner and washed with ethyl acetate to obtain 0.143 g (0.54 mmol, 81%).

$^1$H NMR (400 MHz, DMSO-d6) δ 9.26 (d, J=4.5 Hz, 1H), 8.70 (s, 1H), 8.33-8.25 (m, 2H), 7.62 (t, J=8.2 Hz, 1H), 6.97 (d, J=7.8 Hz, 1H), 4.02 (s, 3H). HRMS (ESI): [M+H]$^+$ calculated for $C_{12}H_{10}N_7O$ 268.094134, measured 268.094006 (−0.5 ppm), [M-N$_2$+H]$^+$ $C_{12}H_{10}N_5O$ calculated for 240.087638, measured 240.087986 (−0.6 ppm).

2-(3-azidopyrazin-2-yl)-7-bromo-pyrazolo[3,4-c]pyridine (107)

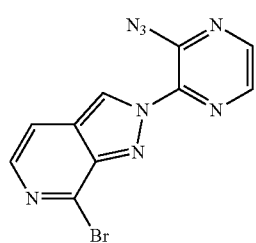

Synthesized according to method A2 from 0.150 g (0.76 mmol, 1 eq.) of 7-bromo-1H-pyrazolo[3,4-c]pyridine (88), 0.033 g (0.83 mmol, 1.1 eq.) of NaH (60 wt %), 0.124 g (0.80 mmol, 1.05 eq.) of azido-chloropyrazine. The product is next precipitated by adding water and ethyl acetate and is next filtered on Büchner and washed with petroleum ether to obtain 0.185 g (0.58 mmol, 77%) of indazolo-azido pyrazine.

$^1$H NMR (250 MHz, DMSO-d6) δ 9.94 (s, 1H), 9.64 (d, J=4.6 Hz, 1H), 8.51 (d, J=4.6 Hz, 1H), 8.00 (d, J=5.9 Hz, 1H), 7.91 (d, J=5.9 Hz, 1H). HRMS (ESI): [M+H]$^+$ calculated for $C_{10}H_6BrN_8$ 316.989331, measured 316.989092 (0.8 ppm).

1-(3-azidopyrazin-2-yl)-1H-indazole-5-carboxylate de sodium (108)

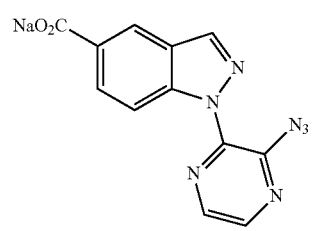

Synthesized according to method A2 from 0.100 g of 5-indazole carboxylic acid (0.617 mmol, 1 eq), 0.051 g of NaH (60 wt %) (1.296 mmol, 2.1 eq), 0.100 g of azidopyrazine (0.648 mmol, 1.05 eq). Direct precipitation by adding ethyl acetate and Büchner filtration. Quantitative yield.

$^1$H NMR (250 MHz, DMSO-d6) δ 9.61 (s, 1H), 9.48 (d, J=4.6 Hz, 1H), 9.30-9.25 (m, 9H), 9.18 (d, J=1.3 Hz, 9H), 8.69 (d, J=0.9 Hz, 9H), 8.41 (d, J=4.4 Hz, 1H), 8.39-8.35 (m, 9H). HRMS (ESI): [M]$^-$ calculated for $C_{12}H_6N_7O_2$ 280.058846, measured 280.059302 (1.6 ppm).

1-(3-azidopyrazin-2-yl)-1H-indazole-4-sodium carboxylate (109)

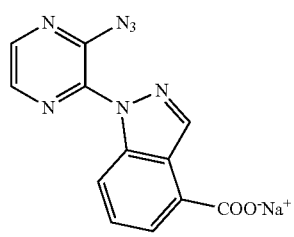

Synthesized according to method A2 from 0.100 g of 4-indazole carboxylic acid (0.617 mmol, 1 eq), 0.051 g of NaH (60 wt %) (1.296 mmol, 2.1 eq), 0.096 g of azidopyrazine (0.648 mmol, 1.05 eq). Direct precipitation by adding ethyl acetate and Büchner filtration. Obtained mass 0.169 g (90%).

$^1$H NMR (250 MHz, DMSO-d6) δ 9.30-9.19 (m, 1H), 8.72 (d, J=8.5 Hz, 1H), 8.30 (d, J=4.6 Hz, 0H), 7.96-7.88 (m, 1H), 7.69-7.55 (m, 1H). HRMS (ESI): $[C_{12}H_6N_7O_2]^-$ calculated for $C_{12}H_6N_7O_2$ 280.058846, measured 280.059302 (1.6 ppm).

1-(3-azidopyrazin-2-yl)-1H-indazole-6-sodium carboxylate (110)

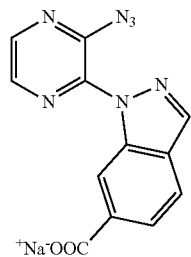

(110)

Synthesized according to method A2 from 0.100 g of 6-indazole carboxylic acid (0.617 mmol, 1 eq), 0.051 g of NaH (60 wt %) (1.296 mmol, 2.1 eq), 0.100 g of azidopyrazine (0.648 mmol, 1.05 eq). Direct precipitation by adding ethyl acetate and Büchner filtration. Quantitative yield.

$^1$H NMR (400 MHz, DMSO-d6) δ 9.62 (d, J=1.1 Hz, 1H), 8.41 (d, J=4.6 Hz, 1H), 7.96 (s, 3H), 7.77-7.75 (m, 2H). HRMS (ESI): [$C_{12}H_6N_7O_2$]_calculated for $C_{12}H_6N_7O_2$ 280.058846, measured 280.059264 (−1.5 ppm).

1-(3-azidopyrazin-2-yl)-5-methyl-1H-indazole (111)

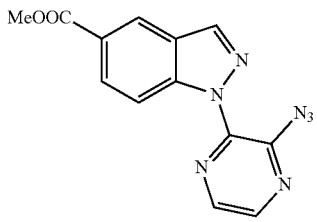

(111)

Synthesized according to method A2 from 0.100 g of 5-indazole methyl ester (0.568 mmol, 1 eq), 0.025 g of NaH (60 wt %) (0.625 mmol, 1.1 eq), 0.088 g of azidopyrazine (0.568 mmol, 1 eq). Direct precipitation by adding water and ethyl acetate and Büchner filtration. Obtained mass 0.128 g (76%).

$^1$H NMR (250 MHz, DMSO-d6) δ 9.34 (d, J=4.6 Hz, 1H), 8.89 (d, J=0.8 Hz, 1H), 8.79 (d, J=8.8 Hz, 1H), 8.68 (dd, J=1.5, 0.7 Hz, 2H), 8.36 (d, J=4.6 Hz, 1H), 8.26 (dd, J=8.8, 1.7 Hz, 1H).

HRMS (ESI): [M+Na]$^+$ calculated for $C_{13}H_9N_7NaO_2$ 318.070993, measured 318.070841 (0.5 ppm).

1-(3-azidopyrazin-2-yl)-6-methyl-1H-indazole (112)

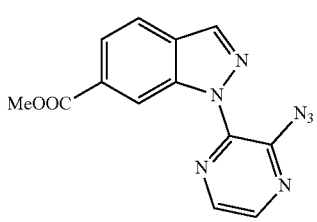

(112)

Synthesized according to method A2 from 0.100 g of 6-indazole methyl ester (0.568 mmol, 1 eq), 0.025 g of NaH (60 wt %) (0.625 mmol, 1.1 eq), 0.088 g of azidopyrazine (0.568 mmol, 1 eq). Direct precipitation by adding water and ethyl acetate and Büchner filtration. Obtained mass 0.090 g (53%).

$^1$H NMR (400 MHz, DMSO-d6) δ 9.34 (d, J=4.6 Hz, 1H), 9.31-9.28 (m, 1H), 8.87 (d, J=0.9 Hz, 1H), 8.41 (d, J=4.6 Hz, 1H), 8.17-8.10 (m, 1H), 8.03 (dd, J=8.3, 1.4 Hz, 1H), 3.96 (s, 3H). HRMS (ESI): [M+Na]$^+$ calculated for $C_{13}H_9N_7NaO_2$ 318.070993, measured 318.071239 (−0.3 ppm). [M+H]$^+$ calculated for $C_{13}H_{10}N_7O_2$ 296.089049, measured 296.089172 (−0.4 ppm).

2-(3-azidopyrazin-2-yl)indazole-7-methyl carboxylate (113)

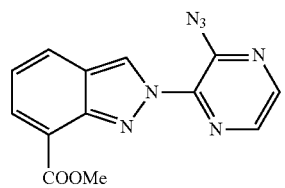

(113)

Synthesized according to method A2 from 0.100 g of 7-indazole methyl ester (0.568 mmol, 1 eq), 0.025 g of NaH (60 wt %) (0.625 mmol, 1.1 eq), 0.088 g of azidopyrazine (0.568 mmol, 1 eq). Direct precipitation by adding water and ethyl acetate and Büchner filtration. Obtained mass 0.051 g (30%).

$^1$H NMR (250 MHz, DMSO-d6) δ 9.90 (s, 1H), 9.54 (s, 1H), 8.47 (s, 1H), 8.33-8.05 (m, 3H), 7.32 (s, 1H), 3.96 (s, 2H). $^1$H NMR (400 MHz, DMSO-d6) δ 9.90 (s, 1H), 9.54 (d, J=4.6 Hz, 1H), 8.47 (d, J=4.5 Hz, 1H), 8.25 (dd, J=8.5, 1.1 Hz, 1H), 8.10 (dd, J=6.9, 1.1 Hz, 1H), 7.31 (d, J=1.5 Hz, 1H), 3.95 (s, 3H). HRMS (ESI): [M-N$_2$+Na]$^+$ calculated for $C_{13}H_9N_5NaO_2$ 290.064845, measured 290.064815 (0.1 ppm).

1-(3-azidopyrazin-2-yl)-1H-indazole-3-methyl carboxylate (114)

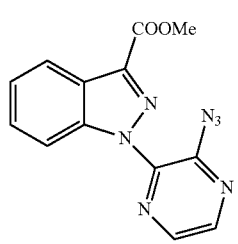

(114)

Synthesized according to method A2 from 0.100 g of 3-indazole methyl ester (0.568 mmol, 1 eq), 0.025 g of NaH (60 wt %) (0.625 mmol, 1.1 eq), 0.088 g of azidopyrazine (0.568 mmol, 1 eq). Direct precipitation by adding water and ethyl acetate and Büchner filtration. Obtained mass 0.125 g (74%).

$^1$H NMR (400 MHz, DMSO-d6) δ 9.43 (d, J=4.7 Hz, 1H), 8.72 (d, J=8.6 Hz, 1H), 8.40 (d, J=4.6 Hz, 1H), 8.30 (d, J=8.0

Hz, 1H), 7.81-7.71 (m, 1H), 7.62 (s, 0H), 4.06 (s, 3H). $^{13}$C NMR (101 MHz, DMSO) δ 161.70, 143.61, 140.31, 140.04, 139.70, 131.11, 129.51, 125.88, 124.19, 121.94, 118.26, 115.36, 52.49. HRMS (ESI): [M+H]$^+$ calculated for $C_{13}H_{10}N_7O_2$ 296.089049, measured 296.088940 (0.4 ppm).

1-(3-azidopyrazin-2-yl)-1H-indazole-4-methyl carboxylate (115)

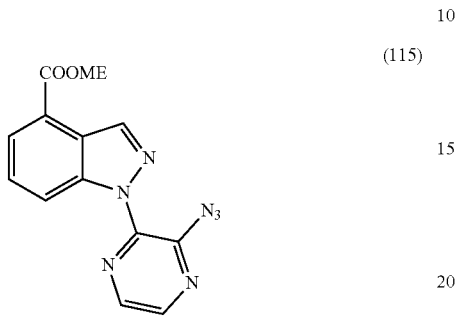

Synthesized according to method A2 from 0.100 g of 3-indazole methyl ester (0.568 mmol, 1 eq), 0.025 g of NaH (60 wt %) (0.625 mmol, 1.1 eq), 0.088 g of azidopyrazine (0.568 mmol, 1 eq). Direct precipitation by adding water and ethyl acetate and Büchner filtration. Obtained mass 0.121 g (72%).

$^1$H NMR (400 MHz, DMSO-d6) δ 9.34 (s, 1H), 9.02 (s, 1H), 8.35 (s, 1H), 8.23-8.07 (m, 2H), 7.84 (s, 1H), 4.02 (s, 3H). $^{13}$C NMR (101 MHz, DMSO) δ 165.40, 143.81, 139.75, 139.55, 139.53, 131.14, 128.78, 126.79, 124.38, 122.75, 120.03, 117.35, 67.00, 59.73, 52.52, 25.11, 20.75, 14.07. HRMS (ESI): [M+H]$^+$ calculated for $C_{13}H_{10}N_7O_2$ 296.089049, measured 296.089090 (-0.1 ppm).

III—Preparation of the Compounds According to the Invention

III.1. Cyclization Via Thermolysis

General procedure B, described below, is implemented to prepare the compounds according to the invention.

General Procedure B

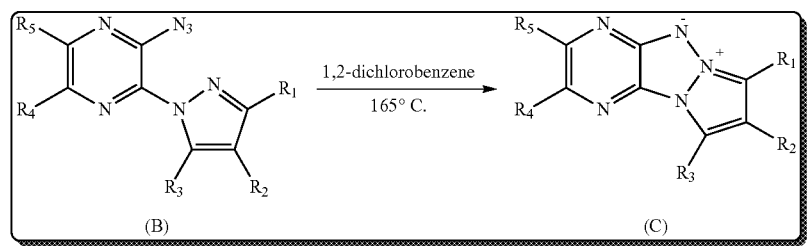

A solution of the intermediary (B) in the 1,2-dichlorobenzene (concentration comprised between 0.06 and 0.1M) placed under argon atmosphere is heated to 165° C. until complete consumption of the starting reagent. After returning to ambient temperature, the solvent is eliminated either by vacuum distillation or by filtration on silica gel by using an apolar solvent (e.g., petroleum ether). The raw product is purified by silica gel column chromatography and is next precipitated in a chloroform/pentane mixture.

Example 1: Pyrazolo[1',2':1,2][1,2,3]triazolo[4,5-b]pyrazin-6-ium-5-ide (36)

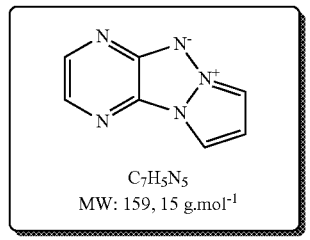

(36)

C$_7$H$_5$N$_5$
MW: 159, 15 g.mol$^{-1}$

This compound was prepared according to General procedure B from 2-azido-3-(1H-pyrazol-1-yl)pyrazine (21) (100 mg, 0.54 mmol, 1 eq) in 1,2-dichlorobenzene (5 mL). The reaction time is 1 h30. The solvent is eliminated by vacuum distillation. The raw product is purified by silica gel column chromatography (dichloromethane/methanol: 98/2; liquid deposition) to obtain the desired product (36: example 1) with a yield of 79% (67 mg) in the form of a yellow powder. Rf (DCM/AcOEt/MeOH: 80/19/1): 0.35. NMR ($^1$H, 400 MHz, chloroform-d) δ 8.44 (d, J=2.6 Hz, 1H), 8.08 (d, J=3.3 Hz, 1H), 7.90 (d, J=2.6 Hz, 1H), 7.84 (d, J=2.5 Hz, 1H), 6.93 (t, J=2.9 Hz, 1H). NMR ($^{13}$C, 101 MHz, chloroform-d) δ 151.64, 142.43, 129.02, 109.32, 108.80, 108.13. SM (IC+) m/z 159 (M+H$^+$).

Example 2: 8-nitropyrazolo[1',2':1,2][1,2,3]triazolo[4,5-b]pyrazin-6-ium-5-ide (37)

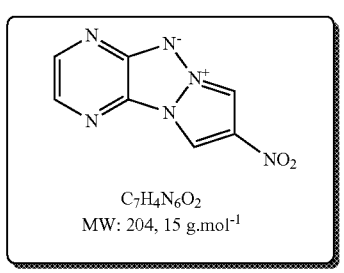

(37)

C$_7$H$_4$N$_6$O$_2$
MW: 204, 15 g.mol$^{-1}$

This compound was prepared according to General procedure B from 2-azido-3-(4-nitro-1H-pyrazol-1-yl)pyrazine (23) (840 mg, 3.63 mmol, 1 eq) in 1,2-dichlorobenzene (37 mL). The reaction time is 4 h. The solvent is eliminated by vacuum distillation. The raw mixture is purified by silica gel column chromatography (3 plateaus, dichloromethane/ethyl acetate: 9/1, dichloromethane/methanol: 98/2 and 95/5). In order to isolate the pure product, several successive purifications were done. The desired product (37: example 2) is obtained with a yield of 69% (513 mg) in the form of a yellow powder. NMR (1H, 400 MHz, chloroform-d) δ 8.71 (d, J=0.7 Hz, 1H), 8.58 (d, J=2.6 Hz, 1H), 8.38 (d, J=0.5 Hz, 1H), 8.08 (d, J=2.6 Hz, 1H). NMR ($^{13}$C, 101 MHz, chloroform-d) 145.43, 133.09, 106.77, 103.91. SM (IC+) m/z 205 (MH+).

Example 3: 7-nitropyrazolo[1',2':1,2][1,2,3]triazolo[4,5-b]pyrazin-6-ium-5-ide (38)

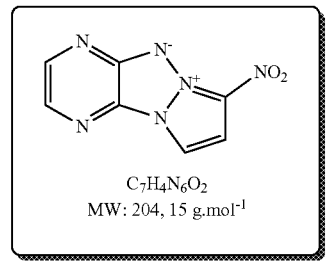

(38)

C$_7$H$_4$N$_6$O$_2$
MW: 204, 15 g.mol$^{-1}$

This compound was prepared according to General procedure B from 2-azido-3-(3-nitro-1H-pyrazol-1-yl)pyrazine (22) (380 mg, 1.64 mmol, 1 eq) in 1,2-dichlorobenzene (15 mL). The reaction time is 1 h. After returning to ambient temperature, the solvent is eliminated by vacuum distillation. The obtained brown solid is washed several times with pentane to eliminate the traces of solvent. The desired product (38: example 3) is obtained with a yield of 93% (513 mg) in the form of a brown powder. NMR ($^1$H, 250 MHz, chloroform-d) δ 8.86 (d, J=2.5 Hz, 1H), 8.42 (d, J=2.4 Hz, 1H), 8.06 (d, J=3.9 Hz, 1H), 7.67 (d, J=4.0 Hz, 1H). SM (IC+) m/z 205 (M+H$^+$).

Example 4: 7-nitro-[1,2,4]triazolo[1',2':1,2][1,2,3]triazolo[4,5-b]pyrazin-6-ium-5-ide (39)

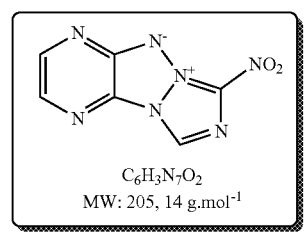

(39)

C$_6$H$_3$N$_7$O$_2$
MW: 205, 14 g.mol$^{-1}$

This compound was prepared according to General procedure B from 2-azido-3-(3-nitro-1H-1,2,4-triazol-1-yl)pyrazine (25) (130 mg, 0.56 mmol, 1 eq) in 1,2-dichlorobenzene (7.5 mL). The reaction time is 3 h. After returning to ambient temperature, the raw mixture is purified by silica gel column chromatography (4 plateaus: petroleum ether: 100%; dichloromethane/ethyl acetate: 100/0, 98/2 and 95/5; liquid deposition). The desired product (39: example 4) is obtained with a yield of 14% (16 mg). NMR ($^1$H, 400 MHz, chloroform-d) δ 8.98 (d, J=2.4 Hz, 1H), 8.80 (s, 1H), 8.54 (d, J=2.4 Hz, 1H). NMR ($^{13}$C, 101 MHz, chloroform-d) δ 147.70, 138.71, 120.76. SM (IC+) m/z 206 (MH$^+$)

Example 5: 7-methoxypyrazolo[1',2':1,2][1,2,3]triazolo[4,5-b]pyrazin-6-ium-5-ide (40)

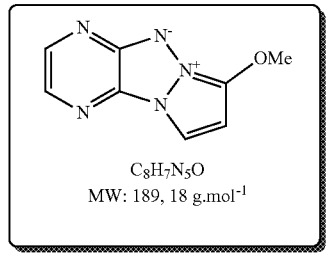

(40)

C$_8$H$_7$N$_5$O
MW: 189, 18 g.mol$^{-1}$

This compound was prepared according to General procedure B from compound (24) (320 mg, 1.47 mmol, 1 eq) in 1,2-dichlorobenzene (15 mL). The reaction time is 2 h. After returning to ambient temperature, the solvent is eliminated by vacuum distillation and the raw residue is purified by silica gel column chromatography (dichloromethane/methanol: 97/3; solid deposition). The desired product (40: example 5) is obtained with a yield of 51% (142 mg) in the form of a brown powder. NMR ($^1$H, 400 MHz, Chloroform-d) δ 8.32 (d, J=2.8 Hz, 1H), 7.96 (d, J=3.5 Hz, 1H), 7.70 (d, J=2.8 Hz, 1H), 6.48 (d, J=3.5 Hz, 1H), 4.24 (s, 3H). NMR ($^{13}$C, 101 MHz, Chloroform-d) δ 143.10, 142.65, 128.35, 110.29, 95.74, 60.15. SM (IC+) m/z 206 (MH$^+$).

Example 6: [1,2,3]triazolo[2',1':1,2][1,2,3]triazolo[4,5-b]pyrazin-9-ium-10-ide (41)

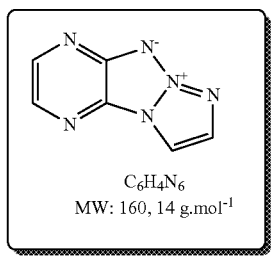

(41)

C$_6$H$_4$N$_6$
MW: 160, 14 g.mol$^{-1}$

This compound was prepared according to General procedure B from compound (26) (30 mg, 0.19 mmol, 1 eq) in 1,2-dichlorobenzene (1 mL). The reaction time is 3 h. After returning to ambient temperature, the solvent is eliminated by vacuum distillation and the raw residue is purified by silica gel column chromatography (dichloromethane/methanol: 97/3; or dichloromethane/ethyl acetate: 7/3; solid deposition). The desired product (41: example 6) is obtained with a yield of 80% (26 mg) in the form of a pale-yellow powder. NMR ($^1$H, 400 MHz, Chloroform-d) δ 8.72 (d, J=2.4 Hz, 1H), 8.35 (d, J=2.4 Hz, 1H), 8.22 (d, J=1.1 Hz, 1H), 8.02 (d, J=1.2 Hz, 1H). NMR ($^{13}$C, 101 MHz, Chloroform-d) δ 150.92, 144.68, 138.32, 135.51, 127.36, 104.83. SM (IC+) m/z 161 (MH$^+$)

Example 7: [1,2,4]triazolo[1',2':1,2][1,2,3]triazolo[4,5-b]pyrazin-6-ium-5-ide (42)

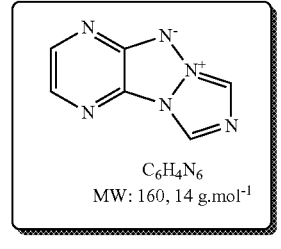

(42)

C$_6$H$_4$N$_6$
MW: 160, 14 g.mol$^{-1}$

This compound was prepared according to General procedure B from compound (27) (470 mg, 2.50 mmol, 1 eq) in 1,2-dichlorobenzene (37 mL). The reaction time is 3 h. After returning to ambient temperature, the raw mixture is purified by silica gel column chromatography (2 plateaus: petroleum ether: 100%; dichloromethane/methanol: 97/3). The desired product (42: example 7) is obtained with a yield of 60% (238 mg) in the form of a yellow powder. NMR ($^1$H, 400 MHz, Chloroform-d) δ 8.80 (s, 1H), 8.58 (d, J=2.4 Hz, 1H), 8.46 (s, 1H), 8.03 (d, J=2.4 Hz, 1H). NMR ($^{13}$C, 101 MHz, Chloroform-d) δ 153.79, 145.45, 131.68, 123.44, 119.38. SM (IC$^+$) m/z 161 (M+H$^+$).

Example 8: Benzo[4',5'][1,2,3]triazolo[1',2':1,2][1,2,3]triazolo[4,5-b]pyrazin-6-ium-5-ide (43)

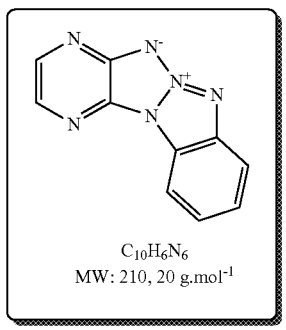

(43)

C$_{10}$H$_6$N$_6$
MW: 210, 20 g.mol$^{-1}$

This compound was prepared according to General procedure B from compound (28) (1.49 mmol) in 1,2-dichlorobenzene (20 mL). The reaction time is 1 h45. After returning to ambient temperature, the raw mixture is purified by silica gel column chromatography (3 plateaus: petroleum ether: 100%; dichloromethane/ethyl acetate: 10/0, 9/1; liquid deposition). The product (43: example 8) is obtained with a yield of 73% (229 mg) in the form of a yellow-green powder. NMR ($^1$H, 400 MHz, Chloroform-d) δ 8.74 (d, J=2.6 Hz, 1H), 8.42 (d, J=2.6 Hz, 1H), 8.30 (d, J=8.2 Hz, 1H), 8.06 (d, J=8.1 Hz, 1H), 7.67 (td, J=7.4, 1.1 Hz, 2H). NMR ($^{13}$C, 101 MHz, Chloroform-d) δ 143.60, 143.10, 136.05, 130.77, 127.54, 125.25, 122.42, 117.98, 110.80. SM (IC$^+$) m/z 211 (MH$^+$).

Example 9: Pyrazino[2',3':4,5][1,2,3]triazolo[1,2-a]indazol-6-ium-5-ide (44)

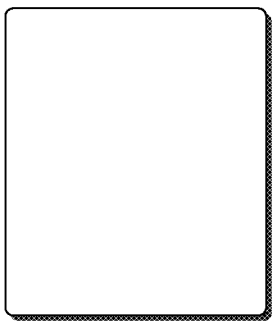

(44)

This compound was prepared according to General procedure B from compound (29) (2.11 mmol) in 1,2-dichlorobenzene (35 mL). The reaction time is 1 h. After returning to ambient temperature, the raw mixture is purified by silica gel column chromatography (3 plateaus: petroleum ether: 100%; dichloromethane/ethyl acetate: 10/0, 9/1 and 8/2; solid deposition). The product (44: example 9) is obtained with a quantitative yield (450 mg) in the form of an orange solid. NMR ($^1$H, 400 MHz, Chloroform-d) δ 8.39 (d, J=2.8 Hz, 1H), 8.31 (d, J=8.3 Hz, 1H), 8.16 (s, 1H), 7.99 (d, J=2.8 Hz, 1H), 7.86 (d, J=8.2 Hz, 1H), 7.61 (t, J=7.7 Hz, 1H), 7.54 (t, J=7.6 Hz, 1H). NMR ($^{13}$C, 101 MHz, Chloroform-d) δ 152.98, 141.28, 132.42, 130.84, 125.91, 125.72, 125.52, 123.79, 119.95, 111.26, 102.35. SM (IC$^+$) m/z 210 (MH$^+$).

Example 10: 8,9,10,11-tetrahydropyrazino[2',3':4,5][1,2,3]triazolo[1,2-a]indazol-6-ium-5-ide (45)

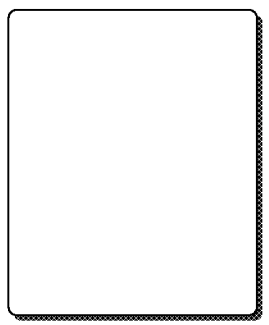

(45)

This compound was prepared according to General procedure B from compound (91) (1.9 mmol) in 1,2-dichlorobenzene (25 mL). The reaction time is 2 h. After returning to ambient temperature, the raw mixture is purified by silica gel column chromatography (3 plateaus: petroleum ether: 100%; dichloromethane/ethyl acetate/methanol: 80/20/0, 80/18/2; solid deposition). The product (45: example 10) is obtained with a yield of 79% (332 mg) in the form of a yellow powder. NMR ($^1$H, 400 MHz, Chloroform-d) δ 8.33 (d, J=2.8 Hz, 1H), 7.81 (s, 1H), 7.77 (d, J=2.8 Hz, 1H), 3.00 (t, J=6.5 Hz, 2H), 2.83 (t, J=6.5 Hz, 2H), 2.06-1.97 (m, 2H), 1.96-1.84 (m, 2H). NMR (13C, 101 MHz, Chloroform-d) δ 142.26, 128.57, 107.06, 22.71, 21.79, 21.43, 20.58. SM (IC+) m/z 214 (MH$^+$).

Example 11: pyrazolo[1',2':1,2][1,2,3]triazolo[4,5-b]quinoxalin-4-ium-5-ide (46)

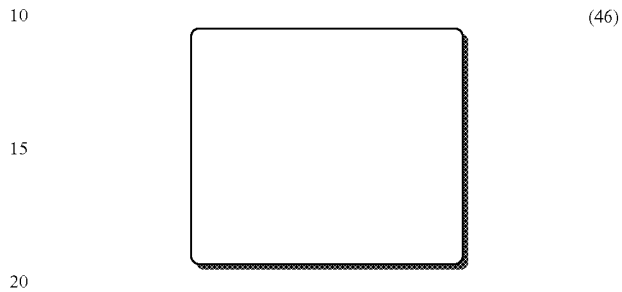

(46)

This compound was prepared according to General procedure B from compound (35) (0.23 mmol) in 1,2-dichlorobenzene (2 mL). The reaction time is 29 h. The solvent is eliminated by vacuum distillation. After returning to ambient temperature, the raw residue is purified by chromatography on silica gel column (dichloromethane/methanol: 10/0, 98/2 and 95/5; solid deposition). The product (46: example 11) is obtained with a yield of 53% (26 mg) in the form of a dark brown powder. NMR ($^1$H, 400 MHz, Chloroform-d) δ 8.24 (d, J=3.4 Hz, 1H), 8.04 (d, J=8.5 Hz, 1H), 8.01 (d, J=8.4 Hz, 1H), 7.93 (d, J=2.4 Hz, 1H), 7.7 (t, J=7.6 Hz, 1H), 7.53 (t, J=7.6 Hz, 1H), 6.95 (t, J=2.4 Hz, 1H). NMR ($^{13}$C, 101 MHz, Chloroform-d) δ 152.66, 143.53, 135.23, 132.08, 129.62, 128.41, 127.91, 125.43, 113.51, 112.18, 110.18. SM (IC+) m/z 210 (MH$^+$).

Example 12: 8-(4,4,5,5-tetramethyl-1,3,2-dioxaborolan-2-yl)pyrazolo[1',2':1,2][1,2,3]triazolo[4,5-b]pyrazin-6-ium-5-ide (47)

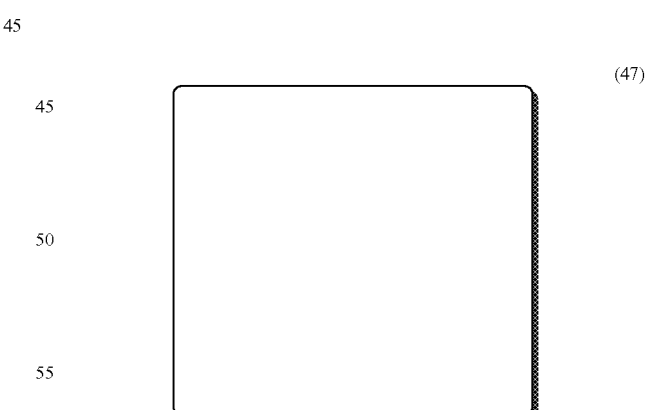

(47)

This compound was prepared according to General procedure B from compound (30) (0.36 mmol) in 1,2-dichlorobenzene (5 mL). The reaction time is 45 min. The solvent is eliminated by vacuum distillation. After returning to ambient temperature, the reaction medium is concentrated. The obtained raw residue is solubilized in a minimum of chloroform and is diluted in pentane (precipitation of impurities). The filtrated is concentrated and is co-evaporated with chloroform. The product (47: example 12) is obtained with a yield of 65% (67 mg) in the form of a yellow powder. NMR ($^1$H, 400 MHz, Chloroform-d) δ 8.38 (d, J=2.6 Hz, 1H), 8.28 (s, 1H), 7.95 (s, 1H), 7.84 (d, J=2.5 Hz, 1H), 1.34 (s, 12H). NMR ($^{13}$C, 400 MHz, Chloroform-d) δ 153.31, 143.53, 129.86, 129.12, 116.15, 113.31, 84.71, 24.90. SM (IC$^+$) m/z 286 (MH$^+$), 204 (MH$^+$-C$_6$H$_{12}$).

Example 13: 7,9-dimethyl-8-(4,4,5,5-tetramethyl-1,3,2-dioxaborolan-2-yl) pyrazolo[1',2':1,2][1,2,3]triazolo[4,5-b]pyrazin-6-ium-5-ide (48)

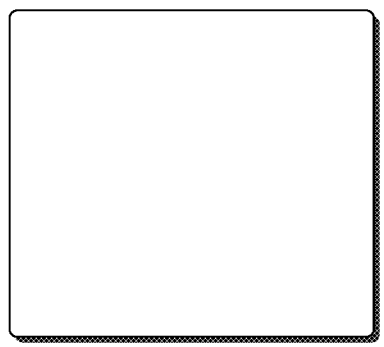

(48)

This compound was prepared according to General procedure B from compound (31) (0.59 mmol) in 1,2-dichlorobenzene (10 mL). The reaction time is 30 min. The solvent is eliminated by evaporation under reduced pressure. The obtained raw residue is solubilized in a minimum of chloroform and is diluted in pentane (precipitation of impurities). The filtrated is concentrated and is co-evaporated with chloroform. The product (48: example 13) is obtained with a yield of 69% (127 mg) in the form of a yellow powder. NMR ($^1$H, 400 MHz, chloroform-d) δ 8.25 (d, J=2.9 Hz, 1H), 7.69 (d, J=2.9 Hz, 1H), 2.99 (s, 3H), 2.72 (s, 3H), 1.37 (s, 12H). NMR ($^{13}$C, 400 MHz, Chloroform-d) δ 154.26 (C$_q$), 142.43, 131.99 (C$_q$), 131.53 (C$_q$), 127.94, 125.26 (C$_q$), 83.96 (C$_q$), 25.08, 11.51, 10.68. SM (IC+) m/z 314 (MH$^+$).

Example 14: 8-bromopyrazolo[1',2':1,2][1,2,3]triazolo[4,5-b]pyrazin-6-ium-5-ide (49)

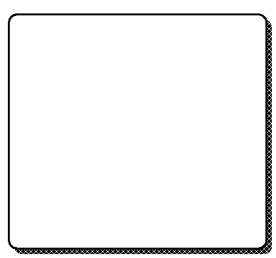

(49)

This compound was prepared according to General procedure B from compound (32) (5.6 mmol) in 1,2-dichlorobenzene (90 mL). The reaction time is 20 min. After returning to ambient temperature, the raw mixture is purified by silica gel column chromatography (petroleum ether: 100%; dichloromethane/ethyl acetate: 10/0 and 9/1; solid deposition). The product (49: example 14) is obtained with a yield of 97% (1.34 g) in the form of a yellow powder. NMR ($^1$H, 400 MHz, Chloroform-d) δ 8.50 (d, J=2.8 Hz, 1H, H), 8.11 (s, 1H), 7.97 (d, J=2.4 Hz, 1H, H), 7.87 (s, 1H). NMR ($^{13}$C, 101 MHz, Chloroform-d) δ 151.48 (C$_q$), 143.86, 131.27, 128.87 (C$_q$), 110.12, 109.50, 98.49. SM (IC$^+$) m/z 239 (MH$^+$).

Example 15: 8-iodopyrazolo[1',2':1,2][1,2,3]triazolo[4,5-b]pyrazin-6-ium-5-ide (50)

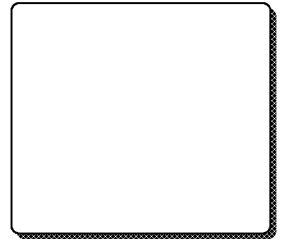

(50)

This compound was prepared according to General procedure B from compound (33) (7.67 mmol) in 1,2-dichlorobenzene (120 mL). The reaction time is 20 min. After returning to ambient temperature, the raw mixture is purified by silica gel column chromatography (petroleum ether: 100%; dichloromethane/ethyl acetate: 10/0, 8/2; solid deposition). The product (50: example 15) is obtained with a yield of 93% (2.03 g) in the form of a yellow-orange powder. R$_f$ (DCM/AcOEt/MeOH: 80/19/1): 0.32. NMR ($^1$H, 400 MHz, Chloroform-d) δ 8.50 (d, J=2.6 Hz, 1H), 8.14 (s, 1H), 7.96 (d, J=2.6 Hz, 1H), 7.87 (s, 1H). NMR ($^{13}$C, 101 MHz, Chloroform-d) δ 150.91, 142.91, 130.07, 127.73, 113.37, 112.02. SM (IC+) m/z 286 (MH$^+$).

Example 16: 7-iodopyrazolo[1',2':1,2][1,2,3]triazolo[4,5-b]pyrazin-6-ium-5-ide (51)

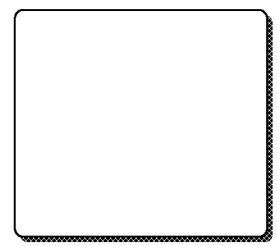

(51)

This compound was prepared according to General procedure B from compound (90) (4.1 mmol) in 1,2-dichlorobenzene (30 mL). The reaction time is 2 h. After returning to ambient temperature, the raw mixture is purified by silica gel column chromatography (2 plateaus: petroleum ether: 100%; dichloromethane/ethyl acetate: 8/1; solid deposition). The product (51: example 16) is obtained with a quantitative yield (888 mg) in the form of a yellow-orange powder. NMR ($^1$H, 400 MHz, Chloroform-d) δ 8.49 (d, J=2.7 Hz, 1H), 8.08 (d, J=3.4 Hz, 1H), 7.93 (d, J=2.7 Hz, 1H), 7.02 (d, J=3.4 Hz, 1H). NMR ($^{13}$C, 101 MHz, Chloroform-d) δ 152.22, 143.82, 130.99, 130.67, 117.52, 111.95, 56.64. SM (IC+) m/z 286 (MH$^+$).

Example 17: Compound (52.1) and Compound (52.2)

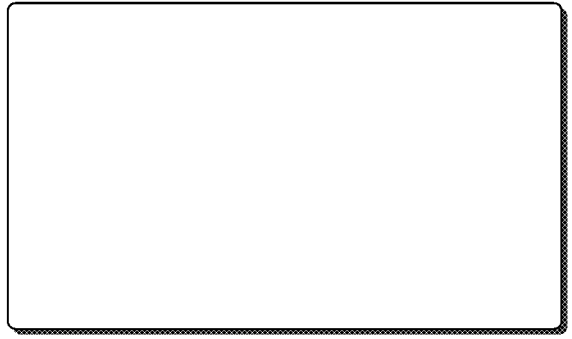

This compound was prepared according to General procedure B from the mixture of two isomers (34.1 and 34.2) (0.84 mmol) in 1,2-dichlorobenzene (12 mL). The reaction time is 1 h. After returning to ambient temperature, the raw mixture is purified by silica gel column chromatography (2 plateaus: petroleum ether: 100%; ethyl acetate/cyclohexane: 4/6). After two successive purifications, the products (52.1) and (52.2) are isolated in the form of an orange powder and a red powder, with yields of 20% (35 mg) and 4% (7 mg). (52.1): NMR ($^1$H, 400 MHz, Chloroform-d) δ 8.87 (d, J=2.4 Hz, 1H), 8.64 (d, J=2.4 Hz, 1H), 8.60 (d, J=2.8 Hz, 1H), 8.38 (s, 1H), 8.27 (d, J=2.9 Hz, 1H). NMR ($^{13}$C, 101 MHz, Chloroform-d) 144.51, 142.81, 139.03, 134.12, 100.92. SM (IC+) m/z 212 (MH$^+$). (52.2): NMR ($^1$H, 400 MHz, Chloroform-d) δ 8.93 (d, J=1.9 Hz, 1H), 8.82 (d, J=2.4 Hz, 1H), 8.77 (s, 1H), 8.67 (d, J=1.9 Hz, 1H), 8.29 (d, J=2.3 Hz, 1H). NMR ($^{13}$C, 101 MHz, Chloroform-d) δ 147.07, 146.88, 141.21, 134.45, 100.14, 99.98. SM (IC+) m/z 212 (MH$^+$).

Example 18: Benzo[d][1,2,3]triazolo[1,2-a][1,2,3]triazol-10-ium-9-ide (53)

(53)

In a dry sealed tube placed under argon, the 1-(2-nitrophenyl)-1H-pyrazole (1) (760 mg, 4.02 mmol, 1 eq) and the triethyl phosphite (15 mL, 87 mmol, 22 eq) are introduced. The reaction medium is heated by microwaves at 176° C. for 1 h30. After returning to ambient temperature, the solvent is eliminated by vacuum distillation. The raw mixture is purified by silica gel column chromatography (2 plateaus: petroleum ether/ethyl acetate: 8/2 and 5/5; solid deposition). After two successive purifications, the compound (53: example 18) is obtained with a yield of 24% (151 mg) in the form of a light-yellow powder. NMR($^1$H, 400 MHz, Chloroform-d) δ 7.67-7.62 (m, 1H), 7.60 (d, J=2.6 Hz, 0H), 7.49 (d, J=8.4 Hz, 1H), 7.36 (ddd, J=8.3, 7.1, 1.2 Hz, 1H), 6.96 (ddd, J=8.1, 7.0, 1.0 Hz, 1H), 6.79 (t, J=2.9 Hz, 1H). NMR ($^{13}$C, 400 MHz, Chloroform-d) δ 126.26, 116.17, 112.93, 109.74, 108.91, 104.57, 103.77. SM (IC+) m/z 190 (M+H$^+$), 212 (M+Na$^+$).

Example 19: Pyrazolo[1',2':1,2][1,2,3]triazolo[4,5-d]pyrimidin-9-ium-10-ide (54)

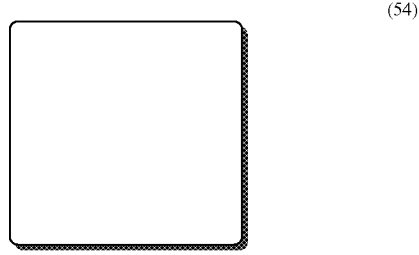
(54)

This compound was prepared according to General procedure B from compound (20) (0.096 mmol) in 1,2-dichlorobenzene (0.75 mL). The reaction time is 20 min. After returning to ambient temperature, the raw mixture is purified by silica gel column chromatography (3 plateaus: petroleum ether: 100%; dichloromethane/methanol: 10/0 and 95/5; solid deposition). The product (54: example 19) is obtained with a yield of 66% (15 mg) in the form of a beige powder. NMR ($^1$H, 400 MHz, Chloroform-d) δ 8.91 (s, 1H), 8.88 (s, 1H), 7.96 (d, J=3.2 Hz, 1H), 7.89 (d, J=2.4 Hz, 1H), 6.93 (se, 1H). NMR ($^{13}$C, 101 MHz, Chloroform-d) δ 160.88, 156.43, 136.24, 113.86, 111.40, 109.73, 109.40. SM (IC+) m/z 160 (MH$^+$).

Example 38: 8-methoxypyrazolo[1',2':1,2][1,2,3]triazolo[4,5-b]pyrazin-6-ium-5-ide (116)

(116)

This compound was prepared according to General procedure B from compound (89) (0.52 mmol) in 1,2-dichlorobenzene (12 mL). The reaction time is 2 h. After returning to ambient temperature, the raw mixture is purified by silica gel column chromatography (2 plateaus: petroleum ether: 100%; dichloromethane/ethyl acetate: 8/2). The product (116: example 38) is obtained with a yield of 40% (39 mg) in the form of a yellow-brown powder. NMR ($^1$H, 400 MHz, Chloroform-d) δ 8.40 (d, J=2.7 Hz, 1H), 7.89 (d, J=2.7 Hz, 1H), 7.70 (s, 1H), 7.66 (s, 1H). NMR ($^{13}$C, 101 MHz, Chloroform-d) δ 142.33, 130.28, 99.58, 94.93, 58.98, the quaternary carbons are not visible. SM (IC+) m/z 190 (MH$^+$).

Example 39: 8-nitropyrazino[2',3':4,5][1,2,3]triazolo[1,2-a]indazol-6-ium-5-ide (117)

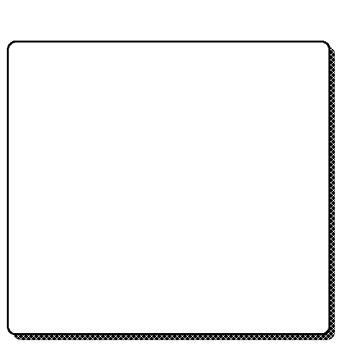

(117)

This compound was prepared according to General procedure B from compound (92) (1.2 mmol) in 1,2-dichlorobenzene (11 mL). The reaction time is 2 h30. After returning to ambient temperature, the raw mixture is purified by silica gel column chromatography (2 plateaus: petroleum ether: 100%; dichloromethane/methanol: 99/1). The product (117: example 39) is obtained with a yield of 88% in the form of an orange powder. NMR ($^1$H, 400 MHz, DMSO-d6) δ 9.21 (s, 1H), 8.71 (d, J=8.2 Hz, 1H), 8.59-8.55 (m, 1H), 8.27 (d, J=2.8 Hz, 1H), 7.80 (t, J=8.1 Hz, 1H). NMR ($^{13}$C, 101 MHz, DMSO-d6) δ 142.0, 132.7, 126.5, 123.59, 122.4, 117.8, 102.3. SM (IC$^+$) m/z 255 (MH$^+$).

Example 40: 9-nitropyrazino[2',3':4,5][1,2,3]triazolo[1,2-a]indazol-6-ium-5-ide (118)

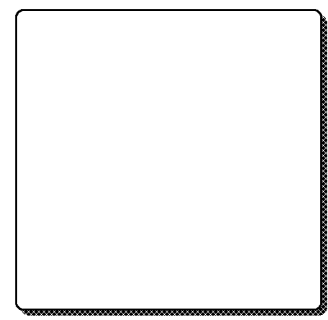

(118)

This compound was prepared according to General procedure B from compound (93) (0.64 mmol) in 1,2-dichlorobenzene (6 mL). The reaction time is 1 h30. After returning to ambient temperature, the raw mixture is purified by silica gel column chromatography (4 plateaus: petroleum ether: 100%; dichloromethane/methanol: 99/1, 98/2, 97/3). The product (118: example 40) is obtained with a yield of 70% in the form of an orange powder. NMR ($^1$H, 400 MHz, DMSO-d6) δ 8.83 (d, J=1.3 Hz, 1H), 8.51 (d, J=2.9 Hz, 1H), 8.45-8.43 (m, 1H), 8.31 (s, 1H), 8.12 (d, J=2.8 Hz, 1H). NMR ($^{13}$C, 101 MHz, DMSO-d6) δ 142.45, 132.38, 126.94, 123.19, 119.58, 116.35, 111.74, 102.26, some quaternary carbons, in particular those of pyrazine, are not visible. SM (IC$^+$) m/z 255 (MH$^+$).

Example 41: 10-nitropyrazino[2',3':4,5][1,2,3]triazolo[1,2-a]indazol-6-ium-5-ide (119)

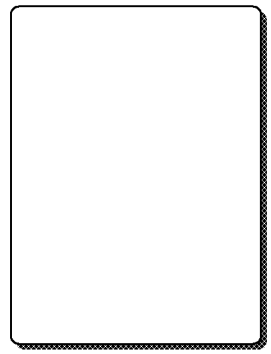

(119)

This compound was prepared according to General procedure B from compound (94) (0.64 mmol) in 1,2-dichlorobenzene (6 mL). The reaction time is 1 h. After returning to ambient temperature, the raw mixture is purified by silica gel column chromatography (4 plateaus: petroleum ether: 100%; dichloromethane/methanol: 99/1, 98/2, 97/3). The product (119: example 41) is obtained with a yield of 92% in the form of a red powder. NMR ($^1$H, 400 MHz, DMSO-d6) 8.98 (s, 1H), 8.92 (s, 1H), 8.55 (s, 1H), 8.36 (d, J=9.0 Hz, 1H), 8.26 (s, 1H), 8.15 (d, J=9.0 Hz, 1H). SM (IC$^+$) m/z 255 (MH$^+$).

Example 42: 7-nitropyrazino[2',3':4,5][1,2,3]triazolo[2,1-a]indazol-6-ium-5-ide (120)

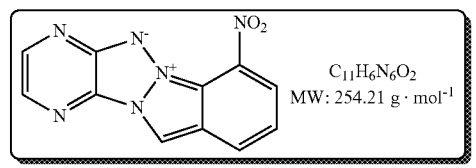

(120)

This compound was prepared according to General procedure B from compound (95) (2.2 mmol) in 1,2-dichlorobenzene (21 mL). The reaction time is 2 h. After returning to ambient temperature, the raw mixture is purified by silica gel column chromatography (4 plateaus: petroleum ether: 100%; dichloromethane/methanol: 99/1, 98/2, 96/4). The product (120: example 42) is obtained with a yield of 67% in the form of a dark red powder. NMR ($^1$H, 400 MHz, DMSO-d6) δ 9.49 (s, 1H), 8.73 (d, J=2.5 Hz, 1H), 8.42 (d, 1H), 8.30 (dd, J=7.5, 0.8 Hz, 1H), 8.23 (d, J=2.5 Hz, 1H), 7.62 (t, J=8.0 Hz, 1H). NMR ($^{13}$C, 101 MHz, DMSO-d6) δ 150.7, 145.98, 136.1, 132.22, 127.0, 127.99, 124.92, 123.90, 122.91, 112.0, 104.31. SM (IC$^+$) m/z 255 (MH$^+$).

Example 43: 2-bromopyrazolo[1',2':1,2][1,2,3]tri-azolo[4,5-b]pyrazin-6-ium-5-ide (121)

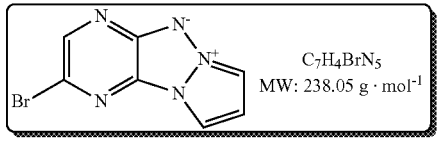

This compound was prepared according to General procedure B from compound (96) (1.9 mmol) in 1,2-dichlorobenzene (8.5 mL). The reaction time is 40 min. After returning to ambient temperature, the raw mixture is purified by silica gel column chromatography (3 plateaus: petroleum ether: 100%; dichloromethane/ethyl acetate: 95/5, 9/1). The product (121: example 43) is obtained with a yield of 46% in the form of a gold flakes. NMR ($^1$H, 400 MHz, chloroform-d) δ 8.51 (s, 1H), 8.07 (dd, J=3.3, 0.5 Hz, 1H), 7.85 (dd, J=2.7, 0.5 Hz, 1H), 6.95 (dd, J=3.4, 2.6 Hz, 1H). NMR ($^{13}$C, 101 MHz, chloroform-d) δ 150.89 (Cq), 144.90, 127.97 (Cq), 122.41 (Cq), 110.52, 110.14, 109.37. SM (IC+) m/z 239 (MH$^+$).

Example 44: 2-bromo-[1,2,4]triazolo[1',2':1,2][1,2,3]triazolo[4,5-b]pyrazin-6-ium-5-ide (122)

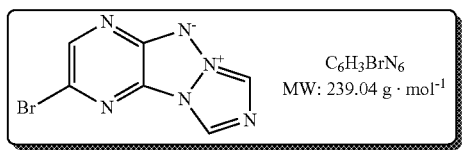

This compound was prepared according to General procedure B from compound (97) (0.6 mmol) in 1,2-dichlorobenzene (3 mL). The reaction time is 90 min. After returning to ambient temperature, the raw mixture is purified by silica gel column chromatography (4 plateaus: petroleum ether: 100%; dichloromethane/methanol: 99/1, 98/2, 97/3). The product (122: example 44) is obtained with a yield of 15% in the form of a gold solid. NMR ($^1$H, 400 MHz, chloroform-d) δ 8.78 (s, 1H), 8.66 (s, 1H), 8.47 (s, 1H). NMR ($^{13}$C, 101 MHz, chloroform-d) δ. SM (IC+) m/z 240 (MH$^+$).

Example 45: Synthesis of Compound (123)

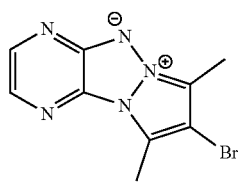

Synthesized using the thermolysis method from 0.150 g of 2-azido-3-(4-bromo-3,5-dimethyl-pyrazol-1-yl)pyrazine (98) (0.51 mmol) at 160° C. for one hour. Obtained mass: 0.122 g (0.46 mmol, 90%), yellow powder.

$^1$H NMR (400 MHz, Chloroform-d) δ 8.33 (s, 0H), 7.78 (d, J=2.4 Hz, 1H), 2.84 (d, J=1.2 Hz, 2H), 2.62 (s, 3H). $^{13}$C NMR (101 MHz, CDCl$_3$) δ 152.24, 142.63, 131.08, 129.13, 122.36, 118.84, 98.73, 10.28, 9.83. HRMS (ESI): [M+H]$^+$ calculated for C$_9$H$_9$BrN$_5$ 266.003584, measured 266.003483 (0.4 ppm).

Example 46: phthalimide triazapentalene (124)

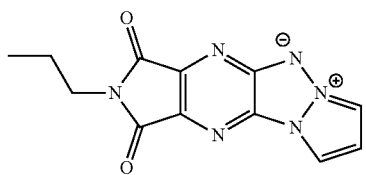

In 10 mL of dry acetonitrile, 0.080 g of 3-chloro-6-propyl-2-pyrazol-1-yl-pyrrolo[3,4-b]pyrazine-5,7-dione (99) (0.27 mmol, 1 eq.) and 0.020 g of sodium azide (0.30 mmol, 1.1 eq.) are dissolved. The mixture is heated for 1 h at 70° C. and the solution becomes orange. The mixture is next dissolved in ethyl acetate and washed with sat NaCl. The organic phase is dried on MgSO$_4$, filtered and purified by chromatography on silica with a DCM/EA mixture as eluent providing 0.029 g of the expected product (0.107 mmol, 40%) in the form of a golden yellow solid.

$^1$H NMR (400 MHz, DMSO-d$_6$) δ 9.05-9.00 (m, 1H), 8.76 (d, J=1.9 Hz, 1H), 7.33 (t, J=2.5 Hz, 1H), 3.58 (t, J=6.8 Hz, 2H), 1.63 (h, J=6.7 Hz, 3H), 0.93-0.85 (m, 3H). $^{13}$C NMR (101 MHz, DMSO) δ 165.26, 165.18, 154.55, 145.95, 132.57, 129.00, 116.30, 114.94, 111.61, 21.56, 11.26. HRMS (ESI): [M+H]$^+$ calculated for C$_{12}$H$_{11}$N$_6$O$_2$ 271.093800, measured 271.093924 (0.5 ppm).

Example 47: 2-azido-3-pyrazol-1-yl-benzo[g]quinoxaline (125)

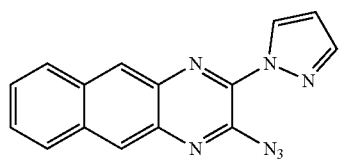

In 5 mL of acetonitrile, 0.065 g (0.23 mmol, 1 eq.) of 3-chloro-2-pyrazol-1-yl-benzo[g]quinoxaline (100) and 0.075 g of sodium azide (1.16 mmol, 5 eq.) are added. The mixture is heated to reflux for one night. After cooling, the mixture is extracted with ethyl acetate and washed with sat NaCl. After drying on MgSO$_4$, filtration and concentration under vacuum, the residue is purified by chromatography on PE/EA silica to obtain 0.025 g (0.087 mmol, 38%) of the expected azide.

$^1$H NMR (250 MHz, Chloroform-d) δ 9.31 (d, J=2.8 Hz, 1H), 9.05 (s, 2H), 8.79 (s, 2H), 8.21-8.06 (m, 6H), 7.80-7.64 (m, 4H), 6.72 (ddd, J=2.8, 1.6, 0.4 Hz, 2H). $^{13}$C NMR (101 MHz, CDCl$_3$) δ 145.43, 138.54, 138.44, 133.50, 132.79, 132.69, 131.47, 129.13, 128.87, 128.85, 128.19, 127.95, 122.41, 114.53, 110.24. HRMS (ESI): [M+H]⁺ calculated for $C_{15}H_{10}N_7$ 288.099220, measured 288.099782 (1.9 ppm), [M-N₂+H]⁺ calculated for $C_{15}H_{10}N_5$ 260.093072, measured 260.093339 (1 ppm).

Example 48: Synthesis of Compound (126)

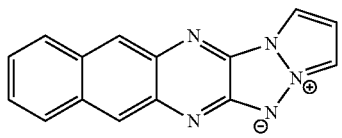
(126)

Synthesized using the thermolysis method from 0.025 g (0.087 mmol) of 2-azido-3-pyrazol-1-yl-benzo[g]quinoxaline (125) at 180° C. for 24 h. Obtained mass: 0.017 g (0.066 mmol, 75%), red powder.

¹H NMR (400 MHz, DMSO-d6) δ 8.96 (d, J=3.5 Hz, 1H), 8.64 (d, J=2.5 Hz, 1H), 8.61 (s, 1H), 8.38 (s, 1H), 8.14 (d, J=8.4 Hz, 1H), 8.09 (d, J=8.4 Hz, 1H), 7.54 (ddd, J=8.2, 6.5, 1.2 Hz, 1H), 7.51-7.45 (m, 1H), 7.21 (dd, J=3.6, 2.5 Hz, 1H). ¹³C NMR (101 MHz, DMSO) δ 153.15, 140.09, 135.10, 133.25, 133.13, 129.79, 127.89, 127.14, 126.17, 125.89, 124.37, 122.60, 117.85, 115.79, 110.99, 40.15, 39.94, 39.73, 39.52, 39.31, 39.10, 38.89. HRMS (ESI): [M+H]⁺ calculated for $C_{15}H_{10}N_5$ 260.093072, measured 260.092575 (−1.9 ppm).

Example 49: Triazapentalene 5-sulfonate (127)

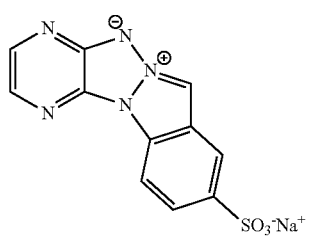
(127)

Synthesized using the thermolysis method from the raw reaction of (102) at 180° C. for 62 h. Precipitation by adding ethyl acetate. Obtained mass: 0.140 g (0.45 mmol, 70% over 2 steps), ochre powder. Analytical sample obtained by purification on silica C18 with water/MeOH as eluent.

¹H NMR (400 MHz, Methanol-d4) δ 8.65 (s, 1H), 8.48-8.46 (m, 1H), 8.38 (d, J=8.7 Hz, 1H), 8.31 (d, J=3.0 Hz, 1H), 8.13 (dd, J=8.6, 1.5 Hz, 1H), 8.04 (d, J=3.0 Hz, 1H). ¹³C NMR (101 MHz, MeOD) δ 153.86, 144.13, 141.31, 131.89, 127.54, 125.07, 124.76, 119.53, 111.94, 105.72. HRMS (ESI): [M+H]⁺ calculated for $C_{11}H_8N_5O_3S$ 290.034237, measured 290.034255 (−0.1 ppm).

Example 50: Triazapentalene 7-carboxylate (128)

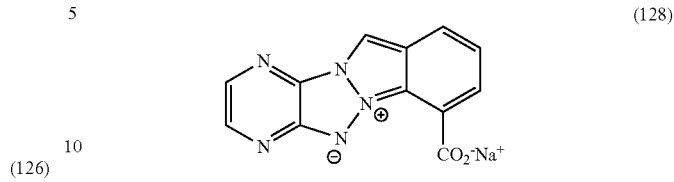
(128)

Synthesized using the thermolysis method from the raw reaction of (101) at 170° C. for 24 h. Precipitation by adding ethyl acetate. Obtained mass: 0.120 g (0.44 mmol, 70% over 2 steps), red powder. Analytical sample purified by DCM/EtOH chromatography+1% NH₃. 9 mg obtained.

¹H NMR (250 MHz, DMSO-d6) δ 9.21 (s, 1H), 8.62 (d, J=2.8 Hz, 1H), 8.09 (d, J=2.6 Hz, 1H), 8.02-7.91 (m, 1H), 7.58 m, 1H), 7.50-7.38 (m, 1H). HRMS (ESI): [M+H]⁺ calculated for $Cl_2H_8N_5O_2$ 254.067251, measured 254.067243 (0 ppm).

Example 51: 7-bromotriazapentalene (129)

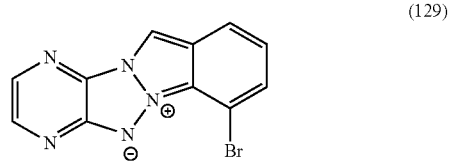 [SMILES: Brc1cccc2cn3c4nccnc4[n-][n+]3c12]
(129)

Synthesized using the thermolysis method from 0.095 g (0.30 mmol) of 2-(3-azidopyrazin-2-yl)-7-bromo-indazole (103) at 140° C. for 2 h.

Silica column chromatography with a PE/EA gradient to provide 0.055 g of the expected product (0.19 mmol, 64%). Red powder.

¹H NMR (400 MHz, Chloroform-d) δ 8.68 (d, J=2.5 Hz, 1H), 8.53 (s, 1H), 8.10 (d, J=2.4 Hz, 1H), 7.81 (d, J=8.6 Hz, 1H), 7.66 (dd, J=7.3, 0.8 Hz, 1H), 7.31-7.26 (m, 1H). ¹³C NMR (101 MHz, CDCl₃) δ 145.84, 132.01, 129.13, 127.11, 126.11, 124.50, 118.96, 105.53, 100.61. HRMS (ESI): [M+H]⁺ calculated for $C_{11}H_7BrN_5$ 287.987934, measured 287.988055 (0.4 ppm).

Example 52: Synthesis of 7-propargylamide triazapentalene (130)

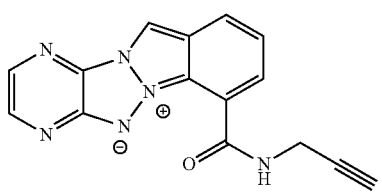
(130)

Synthesized using the thermolysis method from 0.029 g (0.09 mmol) of 2-(3-azidopyrazin-2-yl)-N-prop-2-ynyl-indazole-7-carboxamide (104) for 1 h at 150° C. Silica column chromatography with a PE/EA gradient to provide 0.003 g of the expected product (0.010 mmol, 11%). Orange powder.

¹H NMR (250 MHz, Chloroform-d) δ 11.42 (s, 1H), 8.72-8.64 (m, 3H), 8.14 (d, J=2.5 Hz, 1H), 8.05 (d, J=8.5 Hz, 1H), 7.60 (dd, J=8.6, 7.3 Hz, 1H), 4.49 (dd, J=4.9, 2.5 Hz, 2H), 2.34 (t, J=2.5 Hz, 1H). HRMS (ESI): [M+H]⁺ calculated for $C_{15}H_{11}N_6O$ 291.098885, measured 291.099003 (0.4 ppm).

Example 53: 7-methoxy triazapentalene (131)

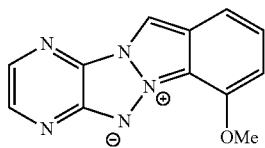

(131)

Synthesized using the thermolysis method from 0.068 g (0.25 mmol) of 2-(3-azidopyrazin-2-yl)-7-methoxy-indazole (105) for 2 h at 140° C.

Silica column chromatography with a PE/EA gradient to provide 0.009 g of the expected product (0.038 mmol, 15%). Red powder.

¹H NMR (400 MHz, Chloroform-d) δ 8.63 (d, J=2.5 Hz, 1H), 8.44 (s, 1H), 8.04 (d, J=2.5 Hz, 1H), 7.37 (d, J=8.6 Hz, 1H), 7.30 (dd, J=8.7, 7.4 Hz, 1H), 6.76 (d, J=7.4 Hz, 1H), 4.17 (s, 3H). ¹³C NMR (101 MHz, CDCl₃) δ 151.74, 147.85, 145.19, 131.27, 127.43, 126.23, 124.80, 115.42, 111.63, 103.57, 100.68, 56.44. HRMS (ESI): [M+H]⁺ calculated for $C_{12}H_{10}N_5O$ 240.087986, measured 240.087862 (0.5 ppm).

Example 54: 4-methoxytriazapentalene (132)

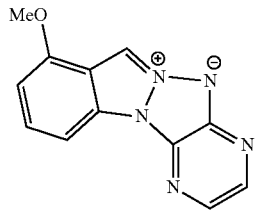

(132)

Synthesized using the thermolysis method from 0.054 g (0.20 mmol) of 1-(3-azidopyrazin-2-yl)-4-methoxy-indazole (106) for 3 h30 at 145° C. Silica column chromatography with a PE/EA gradient to provide 0.048 g of the expected product (quantitative). Yellow powder.

¹H NMR (250 MHz, Chloroform-d) δ 8.37 (d, J=2.8 Hz, 1H), 8.19 (s, 1H), 7.95 (d, J=2.9 Hz, 1H), 7.86 (d, J=8.3 Hz, 1H), 7.52 (t, J=8.2 Hz, 1H), 6.87 (d, J=8.0 Hz, 1H), 4.05 (s, 3H). ¹³C NMR (101 MHz, CDCl₃) δ 153.20, 152.53, 141.36, 130.51, 127.20, 126.90, 115.71, 104.37, 103.81, 101.19, 55.95. HRMS (ESI): [M+H]⁺ calculated for $C_{12}H_{10}N_5O$ 240.087638, measured 240.087986 (-1.5 ppm).

Example 55: 9-(methoxycarbonyl)pyrazino[2',3':4,5][1,2,3]triazolo[1,2-a]indazol-6-ium-5-ide (133)

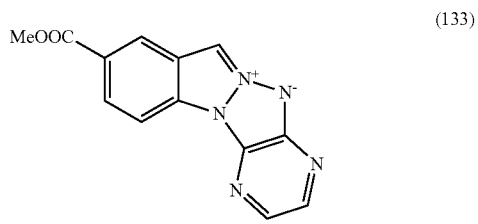 [SMILES: COC(=O)c1ccc2c(c1)c[n+]1[n-]c3nccnc3n21]

(133)

Synthesized using the thermolysis method from 0.029 g (0.098 mmol) of 1-(3-azidopyrazin-2-yl)-5-methyl-1H-indazole (111) for 2 h at 130° C.

Silica column chromatography with a PE/EA gradient to provide 0.013 g of the expected product (49%). Yellow powder.

¹H NMR (250 MHz, Chloroform-d) δ 8.64 (d, J=1.2 Hz, 1H), 8.45 (s, 1H), 8.35 (s, 1H), 8.25 (d, J=0.8 Hz, 1H), 8.06 (s, 1H), 4.01 (s, 3H). ¹³C NMR (101 MHz, CDCl₃) δ 166.47, 152.97, 141.93, 132.19, 131.54, 127.68, 127.37, 126.20, 123.52, 122.61, 111.13, 102.57, 52.74, 0.14. HRMS (ESI): [M+H]⁺ calculated for $C_{13}H_{10}N_5O_2$ 268.082901, measured 268.082845 (0.2 ppm).

Example 56: 8-(methoxycarbonyl)pyrazino[2',3':4,5][1,2,3]triazolo[1,2-a]indazol-6-ium-5-ide (134)

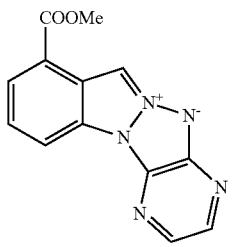

(134)

Synthesized using the thermolysis method from 0.083 g (0.281 mmol) of methyl 1-(3-azidopyrazin-2-yl)-1H-indazole-4-carboxylate (115) for 2 h at 130° C.

Silica column chromatography with a PE/EA gradient to provide 0.056 g of the expected product (74%). Yellow powder.

¹H NMR (250 MHz, Chloroform-d) δ 8.72 (d, J=0.9 Hz, 1H), 8.52 (s, 1H), 8.49 (s, 1H), 8.46 (d, J=2.9 Hz, 1H), 8.06 (d, J=2.9 Hz, 1H), 7.64 (dd, J=8.3, 7.6 Hz, 1H), 4.07 (s, 3H).

¹³C NMR (63 MHz, CDCl₃) δ 165.93, 152.77, 141.90, 131.76, 128.40, 126.18, 124.44, 123.12, 121.34, 115.58, 103.74, 52.71, 0.15. HRMS (ESI): [M+H]⁺ calculated for $C_{13}H_{10}N_5O_2$ 268.082901, measured 268.082705 (0.7 ppm).

Example 57: 10-(methoxycarbonyl)pyrazino[2',3':4,5][1,2,3]triazolo[1,2-a]indazol-6-ium-5-ide (135)

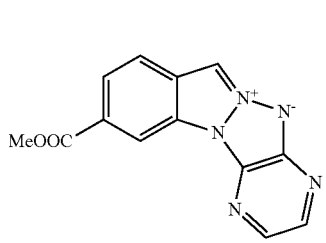

(135)

Synthesized using the thermolysis method from 0.071 g (0.24 mmol) of 1-(3-azidopyrazin-2-yl)-6-methyl-1H-indazole (112) for 2 h at 130° C. Silica column chromatography with a PE/EA gradient to provide 0.047 g of the expected product (72%). Yellow powder.

$^1$H NMR (250 MHz, Chloroform-d) δ 9.01 (s, 1H), 8.56-8.44 (m, 1H), 8.19 (s, 2H), 4.16-3.87 (m, 3H). $^{13}$C NMR (101 MHz, CDCl$_3$) δ 166.51, 152.53, 142.02, 132.32, 126.73, 126.60, 126.28, 125.01, 119.40, 113.24, 101.94, 52.72, 31.08. HRMS (ESI): [M+H]$^+$ calculated for C$_{13}$H$_{10}$N$_5$O$_2$ 268.082901, measured 268.083053 (−0.6 ppm) IR: 3084.54, 2951.99, 1712.19, 1221.02, 1163.67, 1022.85, 960.77, 763.66, 749.73, 718.82 cm$^{-1}$

Example 58: 7-(methoxycarbonyl)pyrazino[2',3':4,5][1,2,3]triazolo[1,2-a]indazol-6-ium-5-ide (136)

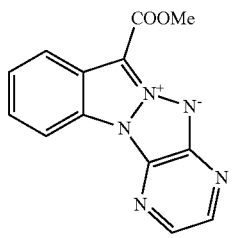

(136)

Synthesized using the thermolysis method from 0.100 g (0.34 mmol) of methyl 1-(3-azidopyrazin-2-yl)-1H-indazole-4-carboxylate (114) for 2 h to 130° C. Silica column chromatography with a PE/EA gradient to provide 0.074 g of the expected product (81%). Yellow powder.

$^1$H NMR (400 MHz, Chloroform-d) δ 8.67 (d, J=2.7 Hz, 1H), 8.31 (d, J=2.7 Hz, 1H), 7.75-7.55 (m, 1H), 4.18 (s, 3H). $^{13}$C NMR (101 MHz, CDCl$_3$) δ 143.17, 135.37, 127.13, 125.95, 124.99, 124.07, 121.49, 111.10, 52.62.

HRMS (ESI): [M+H]$^+$ calculated for C$_{13}$H$_{10}$N$_5$O$_2$ 268.082901, measured 268.082915 (−0.1 ppm) IR: 3072.28, 2952.75, 1690.06, 1462.51, 1296.16, 1241.92, 1019.41, 915.05, 866.28, 759.74, 740.15 cm$^{-1}$ Melting point: 248.7° C.

Example 59: Synthesis of Compound (137)

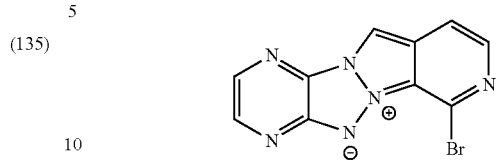

(137)

Synthesized using the thermolysis method from 0.101 g (0.32 mmol) of 2-(3-azidopyrazin-2-yl)-7-bromo-pyrazolo[3,4-c]pyridine (107) for 2 h at 140° C. Silica column chromatography with a PE/EA gradient to provide 30 g of the expected product (orange powder).

$^1$H NMR (250 MHz, Chloroform-d) δ 8.85 (d, J=2.3 Hz, 1H), 8.50 (s, 1H), 8.33 (d, J=2.4 Hz, 1H), 8.21 (d, J=6.1 Hz, 1H), 7.63 (d, J=6.2 Hz, 1H). HRMS (ESI): [M+H]$^+$ calculated for C$_{10}$H$_6$BrN$_6$ 288.983183, measured 288.982549 (2.2 ppm).

Example 60: Synthesis of Compound (138)

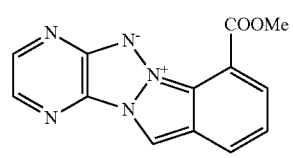

(138)

Synthesized using the thermolysis method from 0.026 g (0.088 mmol) of methyl-(3-azidopyrazin-2-yl)-1H-indazole-7-carboxylate (113) for 1 day at 130° C. Silica column chromatography with a PE/EA gradient to provide 0.005 g of the expected product (21%). Red powder.

$^1$H NMR (250 MHz, Chloroform-d) δ 8.66 (d, J=2.5 Hz, 0H), 8.64 (s, 0H), 8.09-8.02 (m, 1H), 8.00 (dd, J=7.2, 1.0 Hz, 0H), 7.49 (dd, J=8.6, 7.1 Hz, 0H), 4.18 (s, 1H). $^{13}$C NMR (63 MHz, CDCl$_3$) δ 165.55, 151.53, 145.85, 131.71, 128.58, 124.67, 124.44, 124.03, 120.15, 119.15, 118.91, 101.19, 53.56, 53.08, 31.06. HRMS (ESI): [M+H]$^+$ calculated for C$_{13}$H$_{10}$N$_5$O$_2$ 268.082901, measured 268.082803 (−0.4 ppm).

III.2. Suzuki Coupling

General procedure C, described below, is implemented to prepare the compounds according to the invention.

General Procedure C

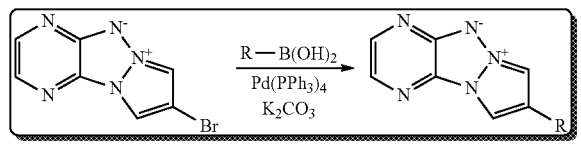

In a dry flask (or sealed tube) placed under argon atmosphere, the 8-bromopyrazolo[1',2':1,2][1,2,3]triazolo[4,5-b]pyrazin-6-ium-5-ide (49) (1 eq) is solubilized in the 1,4-dioxane/H$_2$O (or 1,4-dioxane/EtOH) mixture (2.5/1: v/v; 0.3M). After the introduction of the boronic acid (1.5 eq) and potassium carbonate (6 eq), the reaction medium is degassed for 5 min. The Pd(PPh₃)₄ (5 mol %) is introduced last. The obtained suspension is left under reflux agitation of the solvent (or by microwaves at 150° C.) until total consumption of the boron derivative. After returning to ambient temperature, the reaction medium is concentrated dry and the raw residue is purified by silica gel column chromatography and is next precipitated in a chloroform/pentane mixture.

Example 20: 8-phenylpyrazolo[1',2':1,2][1,2,3]triazolo[4,5-b]pyrazin-6-ium-5-ide (55)

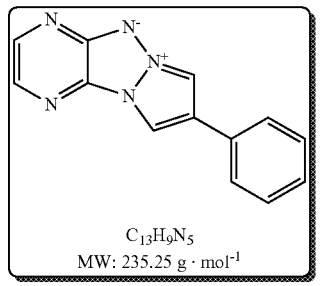

(55)

$C_{13}H_9N_5$
MW: 235.25 g·mol⁻¹

This compound was prepared according to General procedure C in a flask, using phenylboronic acid (28 mg, 0.22 mmol, 1.5 eq) in the 1,4-dioxane/H₂O (3.5 mL/1.5 mL). The reaction mixture is left under reflux agitation of the solvent for 45 min. The raw residue is purified by silica gel column chromatography (dichloromethane/ethyl acetate: 8/2; solid deposition). After precipitation in the chloroform/pentane, the product (55: example 20) is obtained with a yield of 88% (29 mg) in the form of a yellow powder. NMR (¹H, 250 MHz, chloroform-d) δ 8.45 (d, J=2.7 Hz, 1H), 8.28 (s, 1H), 8.09 (s, 1H), 7.93 (d, J=2.7 Hz, 1H), 7.62 (dd, J=8.2, 1.4 Hz, 2H), 7.55-7.36 (m, 3H). NMR (¹³C, 400 MHz, chloroform-d) δ 143.41, 130.46, 130.13, 129.55, 128.91, 127.05, 126.59, 106.72, 106.21, 77.67, 77.16, 76.65. SM (IC+) m/z 236 (MH⁺).

Example 21: 8-(4-methoxyphenyl)pyrazolo[1',2':1,2][1,2,3]triazolo[4,5-b]pyrazin-6-ium-5-ide (56)

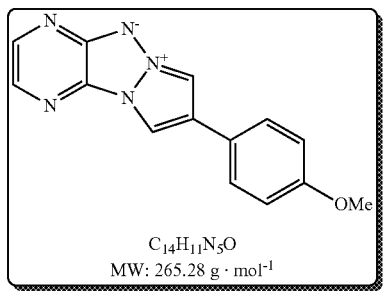

(56)

$C_{14}H_{11}N_5O$
MW: 265.28 g·mol⁻¹

This compound was prepared according to General procedure C in a flask, using 4-methoxy phenylboronic acid (74 mg, 0.47 mmol, 1.5 eq) in the 1,4-dioxane/H₂O (7.5 mL/3 mL). The reaction mixture is left under reflux agitation of the solvent for 5 h. The raw residue is purified by chromatography on silica gel column (dichloromethane/ethyl acetate: 8/2 and dichloromethane/methanol 97/3; solid deposition). The product (56: example 21) is obtained with a yield of 70% (97 mg) in the form of a yellow powder. NMR (¹H, 400 MHz, chloroform-d) δ 8.43 (d, J=2.7 Hz, 1H), 8.19 (s, 1H), 8.03 (s, 1H), 7.91 (d, J=2.7 Hz, 1H), 7.54 (d, J=8.7 Hz, 2H), 7.02 (d, J=8.7 Hz, 2H). NMR (¹³C, 101 MHz, chloroform-d) δ 160.42, 143.34, 130.50, 127.84, 126.93, 122.76, 114.97, 106.58, 105.66, 55.60. SM (IC+) m/z 266 (MH⁺).

Example 22: 8-(4-(dimethylamino)phenyl)pyrazolo[1',2':1,2][1,2,3]triazolo[4,5-b]pyrazin-6-ium-5-ide (57)

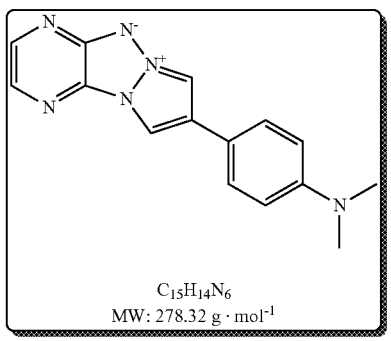

(57)

$C_{15}H_{14}N_6$
MW: 278.32 g·mol⁻¹

This compound was prepared according to General procedure C in a flask, using 4-(N,N-dimethylamino)phenylboronic acid (72 mg, 0.47 mmol, 1.5 eq) in the 1,4-dioxane/H₂O (7.5 mL/3 mL). The reaction mixture is left under reflux agitation of the solvent for 18 h. The raw residue is purified by silica gel column chromatography (dichloromethane/ethyl acetate: 9/1 and 7/3; solid deposition). After precipitation in the chloroform/pentane mixture and washing operations with pentane, the desired product (57: example 22) is obtained with a yield of 82% (73 mg) in the form of a yellow powder. NMR (¹H, 400 MHz, DMSO-d6) δ 8.97 (s, 1H), 8.85 (s, 1H), 8.33 (d, J=2.8 Hz, 1H), 7.88 (d, J=2.8 Hz, 1H), 7.69 (d, J=8.8 Hz, 2H), 6.80 (d, J=8.8 Hz, 2H), 2.95 (s, 6H). SM (IC+) m/z 279 (MH⁺).

Example 23: 8-(pyrimidin-5-yl)pyrazolo[1',2':1,2][1,2,3]triazolo[4,5-b]pyrazin-6-ium-5-ide (58)

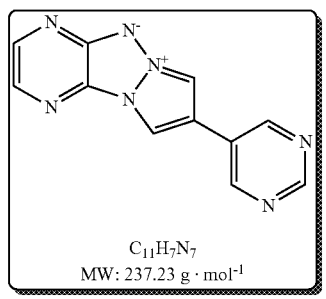

(58)

$C_{11}H_7N_7$
MW: 237.23 g·mol⁻¹

This compound was prepared according to General procedure C in a sealed tube, using pyrimidine-5-boronic acid (93 mg, 0.47 mmol, 1.5 eq) in 1,4-dioxane/H₂O (7.5 mL/3 mL). The reaction medium is heated by microwaves at 150° C. for 20 min (change of color from yellow to brown). The raw residue is purified by chromatography on silica gel column (dichloromethane/methanol: 97/3 and 95/5; solid deposition). After precipitation in the chloroform/pentane mixture and washing operations with pentane, the desired product (58: example 23) is obtained with a yield of 74% (56 mg) in the form of a yellow powder. NMR ($^1$H, 250 MHz, DMSO-d6) δ 9.35 (s, 1H), 9.31 (s, 1H), 9.15 (s, 1H), 9.08 (s, 1H), 8.40 (d, J=2.7 Hz, 1H), 7.94 (d, J=2.7 Hz, 1H). NMR ($^{13}$C, 101 MHz, DMSO-d6) δ 158.09, 154.54, 152.44, 143.37, 130.34, 119.63, 109.28, 107.67. SM (IC+) m/z 238 (MH$^+$).

Example 24: 8-(4-(ethoxycarbonyl)phenyl)pyrazolo[1',2':1,2][1,2,3]triazolo[4,5-b]pyrazin-6-ium-5-ide (59)

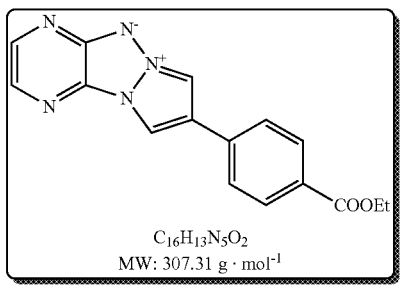

(59)

C$_{16}$H$_{13}$N$_5$O$_2$
MW: 307.31 g·mol$^{-1}$

This compound was prepared according to General procedure C in a sealed tube, using 4-(ethoxycarbonyl)phenylboronic acid (93 mg, 0.48 mmol, 1.6 eq) in the 1,4-dioxane/EtOH (7.5 mL/3 mL). The reaction medium is heated by microwaves at 150° C. for 20 min (change of color from yellow to brown). The raw residue is purified by chromatography on silica gel column (dichloromethane/methanol: 100/0 and 97/3; solid deposition). After precipitation in the chloroform/pentane mixture and washing operations with pentane, the desired product (59: example 24) is obtained with a yield of 85% (84 mg) in the form of a yellow powder. NMR ($^1$H, 400 MHz, chloroform-d) δ 8.48 (d, J=2.3 Hz, 1H), 8.35 (s, 1H), 8.15 (d, J=3.3 Hz, 2H), 7.95 (d, J=2.4 Hz, 1H), 7.69 (d, J=8.2 Hz, 2H), 4.42 (q, J=7.1 Hz, 2H), 1.43 (t, J=7.1 Hz, 3H). NMR ($^{13}$C, 400 MHz, chloroform-d) δ 165.86, 152.07, 143.35, 134.32, 130.46, 126.00, 125.62, 106.39, 61.08, 14.30. SM (IC+) m/z 308 (MH$^+$).

Example 25: 8-(4-cyanophenyl)pyrazolo[1',2':1,2][1,2,3]triazolo[4,5-b]pyrazin-6-ium-5-ide (60)

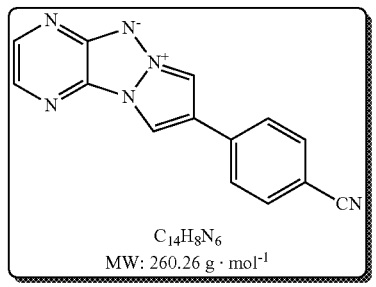

(60)

C$_{14}$H$_8$N$_6$
MW: 260.26 g·mol$^{-1}$

This compound was prepared according to General procedure C in a sealed tube, using 4-cyanophenylboronic acid (48 mg, 0.32 mmol, 1.5 eq) in the 1,4-dioxane/H$_2$O (7.5 mL/3 mL). The reaction medium is heated by microwaves at 150° C. for 30 min (change of color from yellow to green-brown). After returning to ambient temperature, the reaction medium is filtered on millipore and is rinsed with 1,4-dioxane. After washing with pentane, the desired product (60: example 25) is obtained with a quantitative yield (58 mg) in the form of a greenish powder. NMR ($^1$H, 250 MHz, DMSO-d6) δ 9.32 (s, 1H), 9.08 (s, 1H), 8.37 (d, J=2.7 Hz, 1H), 8.07 (d, J=8.7 Hz, 2H), 7.97 (d, J=8.7 Hz, 2H), 7.96 (d, J=2.7 Hz, 1H). SM (IC+) m/z 261 (MH$^+$).

Example 26: 8-(4-carboxyphenyl)pyrazolo[1',2':1,2][1,2,3]triazolo[4,5-b]pyrazin-6-ium-5-ide (61)

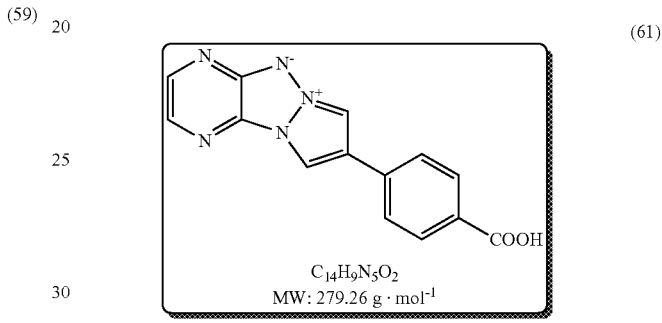

(61)

C$_{14}$H$_9$N$_5$O$_2$
MW: 279.26 g·mol$^{-1}$

This compound was prepared according to General procedure C in a sealed tube, using 4-ethoxycarbonyl)phenylboronic acid (93 mg, 0.48 mmol, 1.6 eq) in the 1,4-dioxane/H$_2$O (7.5 mL/3 mL). The reaction medium is heated by microwaves at 150° C. for 20 min (change of color from yellow to brown). The raw residue is purified by chromatography on silica gel column (dichloromethane/methanol: 100/0, 97/3, 90/10 and 70/30; solid deposition). The product (61: example 26) is obtained with a yield of 85% (84 mg) in the form of a yellow powder. SM (IC+) m/z 280 (MH$^+$)

Example 27: 8-(thiophen-2-yl)pyrazolo[1',2':1,2][1,2,3]triazolo[4,5-b]pyrazin-6-ium-5-ide (62)

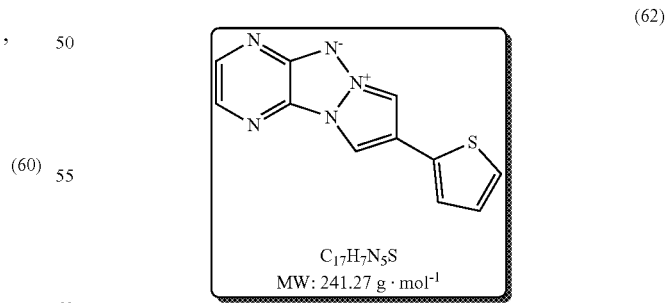

(62)

C$_{17}$H$_7$N$_5$S
MW: 241.27 g·mol$^{-1}$

This compound was prepared according to General procedure C in a sealed tube, using 2-thienylboronic acid (62 mg, 0.48 mmol, 1.5 eq) in the 1,4-dioxane/H$_2$O (7.5 mL/3 mL). The reaction medium is heated by microwaves at 150° C. for 1 h (change of color from yellow to brown). The raw residue is purified by silica gel column chromatography (dichloromethane/ethyl acetate: 100/0 and 90/10; solid deposition). The desired product (62: example 27) is obtained with a yield of 86% (67 mg) in the form of a yellow powder. NMR ($^1$H, 400 MHz, chloroform-d) δ 8.45 (d, J=2.0 Hz, 1H), 8.20 (s, 1H), 8.01 (s, 1H), 7.93 (d, J=2.4 Hz, 1H), 7.37 (d, J=5.1 Hz, 1H), 7.31 (d, J=3.5 Hz, 1H), 7.13 (t, J=3.65 Hz, 1H). NMR ($^{13}$C, 101 MHz, chloroform-d) δ 152.31, 143.48, 132.06, 130.72, 129.35, 128.31, 126.07, 125.56, 120.91, 106.49, 105.95. SM (IC+) m/z 242 (MH$^+$).

Example 28: 7-phenylpyrazolo[1',2':1,2][1,2,3]triazolo[4,5-b]pyrazin-6-ium-5-ide (63)

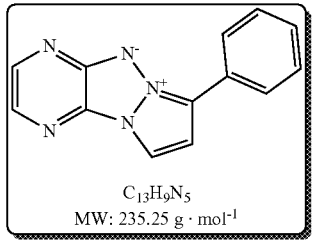

(63)

C$_{13}$H$_9$N$_5$
MW: 235.25 g·mol$^{-1}$

This compound was prepared according to General procedure C in a dry flask, using the 7-iodopyrazolo[1',2':1,2][1,2,3]triazolo[4,5-b]pyrazin-6-ium-5-ide (51) (100 mg, 0.35 mmol, 1 eq) and the phenylboronic acid (65 mg, 0.53 mmol, 1.5 eq) in the 1,4-dioxane/H$_2$O (5.6 mL/2.2 mL) The reaction mixture is left under reflux agitation of the solvent for 1 h30. After returning to ambient temperature, the reaction medium is concentrated dry and the raw residue is purified by silica gel column chromatography (dichloromethane/methanol 100/0, 95/5; solid deposition). After precipitation in the chloroform/pentane mixture and washing operations with pentane, the desired product (63: example 28) is obtained with a yield of 28% (80 mg) in the form of an orange powder. NMR ($^1$H, 250 MHz, chloroform-d) δ 8.47 (d, J=2.9 Hz, 1H), 8.38 (d, J=7.3 Hz, 2H), 8.15 (d, J=3.4 Hz, 1H), 7.92 (d, J=2.7 Hz, 2H), 7.61-7.52 (m, 1H), 7.44 (d, J=7.2 Hz, 1H). NMR ($^{13}$C, 101 MHz, chloroform-d) δ 142.34, 129.42, 128.22, 128.00, 125.97, 125.14, 109.91, 106.54.

Example 62: 8-(5-acetylthiophen-2-yl)pyrazolo[1',2':1,2][1,2,3]triazolo[4,5-b]pyrazin-6-ium-5-ide (139)

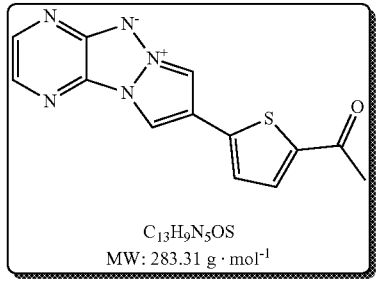

(139)

C$_{13}$H$_9$N$_5$OS
MW: 283.31 g·mol$^{-1}$

This compound was prepared according to General procedure C in a flask, using 5-acetyl-2-thienylboronic acid (55 mg, 0.32 mmol, 1.5 eq) in the 1,4-dioxane/H$_2$O (4.25 mL/1.75 mL). The reaction mixture is left under reflux agitation of the solvent for 48 h. The raw residue is purified by silica gel column chromatography (dichloromethane/ethyl acetate: 100/0 and 90/10; solid deposition). After precipitation in the chloroform/pentane mixture and washing operations with pentane, the desired product (139: example 62) is obtained with a yield of 8% in the form of a yellow powder. NMR ($^1$H, 400 MHz, chloroform-d) δ 8.49 (d, J=2.6 Hz, 1H), 8.29 (s, 1H), 8.07 (s, 1H), 7.98 (d, J=2.6 Hz, 1H), 7.69 (d, J=4.2 Hz, 2H), 7.33 (d, J=3.9 Hz, 1H), 2.60 (s, 3H). NMR ($^{13}$C, 101 MHz, chloroform-d, 3K scans) δ no carbon is visible. SM (IC+) m/z 284 (MH$^+$).

Example 63: 8-(2,6-dimethoxyphenyl)pyrazolo[1',2':1,2][1,2,3]triazolo[4,5-b]pyrazin-6-ium-5-ide (140)

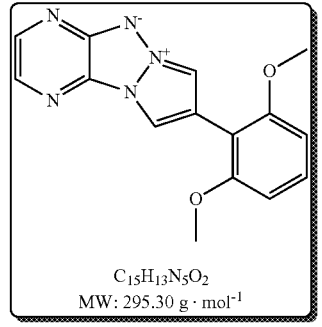

(140)

C$_{15}$H$_{13}$N$_5$O$_2$
MW: 295.30 g·mol$^{-1}$

This compound was prepared according to General procedure C in a sealed tube, using 2,6-dimethoxyphenylboronic acid (49 mg, 0.26 mmol, 1.5 eq) in the 1,4-dioxane/H$_2$O (4.25 mL/1.75 mL). The reaction medium is heated by microwaves at 150° C. for 20 min. The raw residue is purified by silica gel column chromatography (dichloromethane/ethyl acetate: 90/10 and 70/30; solid deposition); The product (140: example 63) is obtained with a yield of 80% (41 mg) in the form of a yellow powder. NMR ($^1$H, 400 MHz, chloroform-d) δ 8.61 (s, 1H), 8.44 (s, 1H), 8.37 (d, J=2.8 Hz, 1H), 7.83 (d, J=2.8 Hz, 1H), 7.32 (t, J=8.4 Hz, 1H), 6.71 (d, J=8.4 Hz, 2H), 3.94 (s, 6H). NMR ($^{13}$C, 101 MHz, chloroform-d) δ 157.76, 152.73, 142.63, 129.55, 128.91, 117.40, 111.39, 111.17, 107.52, 104.30, 55.90. SM (IC+) m/z 296 (MH$^+$).

Example 64: 8-(furan-2-yl)pyrazolo[1',2':1,2][1,2,3]triazolo[4,5-b]pyrazin-6-ium-5-ide (141)

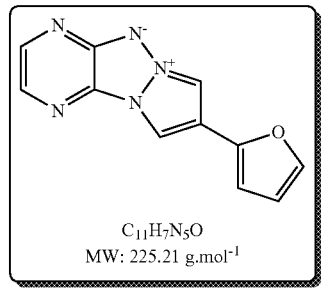

(141)

C$_{11}$H$_7$N$_5$O
MW: 225.21 g.mol$^{-1}$

This compound was prepared according to General procedure C in a sealed tube, using 2-furanylboronic acid (30 mg, 0.26 mmol, 1.5 eq) in the 1,4-dioxane/H$_2$O (4.75 mL/1.75 mL). The reaction medium is heated by microwaves at 150° C. for 18 min. The raw residue is purified by silica gel column chromatography (dichloromethane/ethyl acetate: 100/0 and 90/10; solid deposition). The product (141: example 64) is obtained with a yield of 83% in the form of a yellow-green powder. NMR ($^1$H, 400 MHz, chloroform-d) δ 8.45 (d, J=2.7 Hz, 1H), 8.23 (s, 1H), 8.03 (s, 1H), 7.93 (d, J=2.7 Hz, 1H), 7.52 (dd, J=1.9, 0.8 Hz, 1H), 6.66 (dd, J=3.4, 0.8 Hz, 1H), 6.53 (dd, J=3.4, 1.8 Hz, 1H). NMR ($^{13}$C, 101 MHz, chloroform-d) δ 152.36 (Cq), 144.99 (Cq), 143.30, 142.82, 130.51, 129.24 (Cq), 117.98 (Cq), 111.74, 107.32, 105.32, 104.97. SM (IC+) m/z 226 (MH$^+$).

Example 65: (E)-8-styrylpyrazolo[1',2': 1,2][1,2,3]triazolo[4,5-b]pyrazin-6-ium-5-ide (142)

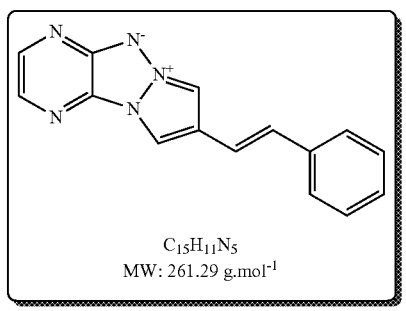

(142)

C$_{15}$H$_{11}$N$_5$
MW: 261.29 g.mol$^{-1}$

This compound was prepared according to General procedure C in a sealed tube, using E-2-phenylvinylboronic acid (120 mg, 0.79 mmol, 1.5 eq) in the 1,4-dioxane/H$_2$O (7.5 mL/3 mL). The reaction medium is heated by microwaves at 150° C. for 30 min. The raw residue is purified by silica gel column chromatography (dichloromethane/ethyl acetate: 100/0, 95/5 and 90/10; solid deposition). The desired product (142: example 65) is obtained with a yield of 62% in the form of a yellow powder. NMR ($^1$H, 400 MHz, chloroform-d) δ 8.43 (d, J=2.7 Hz, 1H), 8.12 (s, 1H), 8.00 (s, 1H), 7.91 (d, J=2.7 Hz, 1H), 7.52 (d, J=7.3 Hz, 3H), 7.40 (t, J=7.4 Hz, 3H), 7.32 (t, J=7.3 Hz, 1H), 7.10 (d, J=16.4 Hz, 1H), 7.02 (d, J=16.4 Hz, 1H). NMR ($^{13}$C, 101 MHz, chloroform-d) δ 135.98, 132.19, 130.32, 129.26, 128.87, 128.49, 126.54, 124.57, 116.53, 107.09, 106.32, 33.41. SM (IC+) m/z 262 (MH$^+$).

Example 66: 2-(phenyl)pyrazolo[1',2':1,2][1,2,3]triazolo[4,5-b]pyrazin-6-ium-5-ide (143)

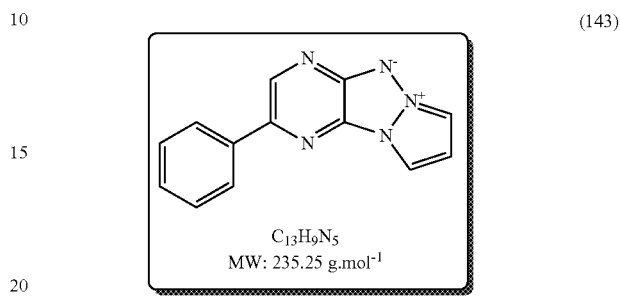

(143)

C$_{13}$H$_9$N$_5$
MW: 235.25 g.mol$^{-1}$

This compound was prepared according to General procedure C in a flask, using phenylboronic acid (11 mg, 0.09 mmol, 1.5 eq) in the 1,4-dioxane/H$_2$O (3.5 mL/1.5 mL). The reaction mixture is left under reflux agitation of the solvent for 1 h30. The raw residue is purified by chromatography on silica gel column (petroleum ether/ethyl acetate: 7/3, 6/4 and 5/5; solid deposition). After precipitation in the chloroform/pentane, the product (143: example 66) is obtained with a quantitative yield in the form of a yellow powder. NMR ($^1$H, 400 MHz, chloroform-d) δ 8.95 (s, 1H), 8.13 (d, J=3.3 Hz, 1H), 8.01 (d, J=8.4 Hz, 2H), 7.85 (d, J=2.6 Hz, 1H), 7.51 (t, J=7.6 Hz, 2H), 7.41 (t, J=7.4 Hz, 1H), 6.94 (t, J=3.0 Hz, 1H). NMR ($^{13}$C, 400 MHz, chloroform-d) δ 151.42, 149.39, 141.13, 139.44, 136.93, 129.04, 128.40, 126.14, 110.18, 109.68, 109.10. SM (IC+) m/z 236 (MH$^+$).

Example 67: 2-(pyrimidin-5-yl)pyrazolo[1',2':1,2][1,2,3]triazolo[4,5-b]pyrazin-6-ium-5-ide (144)

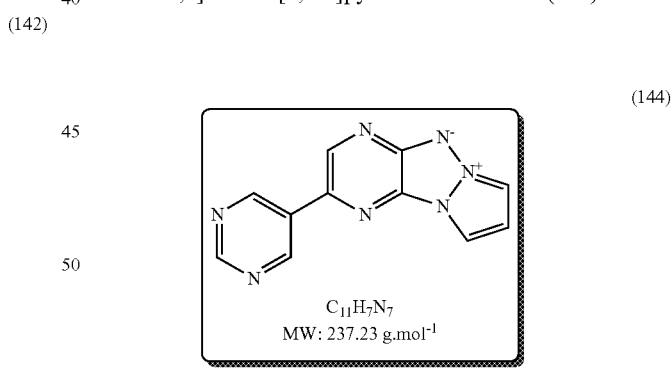

(144)

C$_{11}$H$_7$N$_7$
MW: 237.23 g.mol$^{-1}$

This compound was prepared according to General procedure C in a dry flask and under argon, using pyrimidine-5-boronic acid (39 mg, 0.32 mmol, 1.5 eq) in the 1,4-dioxane/H$_2$O (5 mL/2 mL). The reaction mixture is left under reflux agitation of the solvent for 4 h. The raw residue is purified by silica gel column chromatography (dichloromethane/ethyl acetate: 8/2; solid deposition). The desired product (144: example 67) is obtained with a quantitative yield (53 mg) in the form of an orange powder. NMR ($^1$H, 400 MHz, chloroform-d) δ 9.36 (s, 2H), 9.23 (s, 1H), 8.95 (s, 1H), 8.19 (dd, J=3.4, 0.5 Hz, 1H), 7.92 (dd, J=2.7, 0.5 Hz, 1H), 7.00 (dd, J=3.4, 2.7 Hz, 1H). NMR ($^{13}$C, 101 MHz, chloroform-d) δ 157.79, 153.89, 140.66, 132.94, 130.59, 111.40, 110.37, 110.14. SM (IC+) m/z 238 (MH+).

Example 68: 2-(4-nitrophenyl)pyrazolo[1',2':1,2][1,2,3]triazolo[4,5-b]pyrazin-6-ium-5-ide (145)

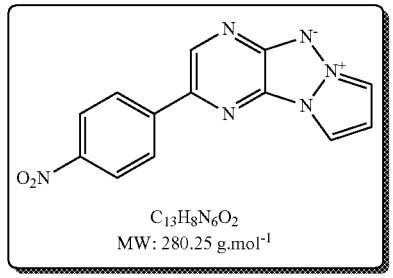

(145)

C₁₃H₈N₆O₂
MW: 280.25 g.mol⁻¹

This compound was prepared according to General procedure C in a dry flask and under argon, using 4-nitrophenylboronic acid (275 mg, 1 mmol, 1.5 eq) in the 1,4-dioxane/H₂O. The reaction mixture is left under reflux agitation of the solvent for 6 h. The raw residue is purified by chromatography on silica gel column (dichloromethane/methanol: 99/1,98/2, 97/3; solid deposition). The desired product (145: example 68) is obtained with a yield of 79% in the form of a red powder. NMR (¹H, 400 MHz, chloroform-d) 9.2 (s, 1H), 8.8 (m, 1H), 8.5 (m, 1H), 8.36 (qd, J=9.1, 2.3 Hz, 4H), 7.23 (t, J=3.0 Hz, 1H). NMR (¹³C, 101 MHz, chloroform-d) δ 152.4, 146.9, 143.5, 141.8, 134.2, 129.8, 126.4, 124.7, 114.1, 112.5, 111.2. SM (IC+) m/z 281 (MH+).

Example 69: Synthesis of Compound (146)

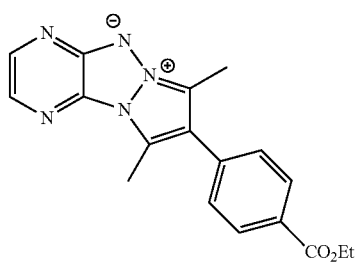

(146)

In a toluene/THF/water 1:1:1 mixture (15 mL), 0.050 g of 4-bromo-3,5-dimethyl-pyrazolo-pyrazino triazapentalene (123) (0.19 mmol, 1 eq.), 0.109 g of para-ethylcarboxyphenyl boronic acid (0.56 mmol, 3 eq.), and 0.080 g of sodium carbonate (0.75 mmol, 4 eq.) are dissolved. The mixture is degassed by bubbling argon for 5 minutes, then 0.022 g of Pd(PPh₃)₄ (0.019 mmol, 0.1 eq.) is added. The solution is heated by microwaves with reflux for 2 h (600 W, 85° C.). After cooling, the solution is diluted in ethyl acetate and washed with sat NaCl. The organic phase is dried on MgSO₄, filtered and purified by 4 successive chromatographies on silica using different effluents (PE/EA, DCM/MeOH, DCM/Et2O then PE/EA). After purification, 21 mg of the expected product is obtained in the form of a yellow powder (0.063 mmol, 33%).

¹H NMR (250 MHz, Chloroform-d) δ 8.33 (d, J=2.8 Hz, 1H), 8.22-8.17 (m, 2H), 7.78 (d, J=2.8 Hz, 1H), 7.50-7.43 (m, 2H), 4.44 (q, J=7.1 Hz, 2H), 2.88 (s, 3H), 2.64 (s, 3H), 1.43 (t, J=7.1 Hz, 3H).

¹³C NMR (101 MHz, CDCl₃) δ 166.22, 153.00, 142.49, 135.92, 135.05, 131.50, 130.37, 130.30, 129.89, 128.74, 128.39, 125.65, 121.87, 121.22, 118.00, 61.42, 30.47, 14.50, 10.12, 9.79.

HRMS (ESI): [M+H]⁺ calculated for C₁₈H₁₈N₅O₂ 336.145501, measured 336.145456 (−0.1 ppm).

Example 70: Synthesis of 7-(2-thiophene)-triazapentalene (147)

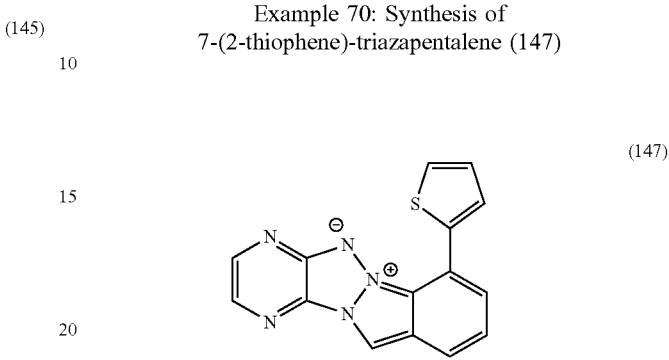

(147)

In a flask, 0.055 g of 7-bromotriazapentalene (129) (0.19 mmol, 1 eq.), 0.049 g of thiophene-2-boronic acid (0.38 mmol, 2 eq.) and 0.079 g of K₂CO₃ (0.57 mmol, 3 eq.) in a THF/water 1:1 mixture are dissolved. The mixture is degassed by bubbling argon, then one adds 0.011 g of Pd(PPh₃)₄ (0.01 mmol, 0.05 eq.). The solution is heated with reflux by microwaves for 2 h at a power of 680 W, the starting product not being fully consumed, one adds 1 eq. of boronic acid and 0.05 eq. of catalyst and the reaction is heated for 2 h50 more. The mixture is next diluted in ethyl acetate and washed with sat NaCl. After drying on MgSO₄, filtration and concentration under reduced pressure, the residue is purified by chromatography with PE/EA as eluent to yield 20 mg of the expected product (0.069 mmol, 36%).

¹H NMR (250 MHz, Chloroform-d) δ 8.60 (d, J=2.3 Hz, 2H), 8.12 (dd, J=3.7, 1.1 Hz, 1H), 8.04 (d, J=2.5 Hz, 1H), 7.82 (dd, J=8.5, 1.0 Hz, 1H), 7.60 (dd, J=7.1, 0.9 Hz, 1H), 7.50-7.40 (m, 2H), 7.32-7.26 (m, 1H).

HRMS (ESI): [M+H]⁺ calculated for C₁₅H₁₀N₅S 292.065143, measured 292.065085 (−0.2 ppm).

III.3. Stille Coupling

General procedure D, described below, is implemented to prepare the compounds according to the invention.

General Procedure D

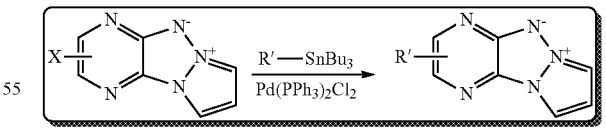

The stannylation derivative (1 eq) is introduced dropwise into a dry flask (or sealed tube) placed under argon atmosphere, containing a suspension of the halogen intermediary (for example compound 121) (1 eq) in toluene (0.25M). The reaction medium is released with argon for 10 min; next, the Pd(PPh₃)₂Cl₂ (10 mol %) is introduced. The obtained suspension is left under reflux agitation of the solvent until total consumption of the halogen derivative. After returning to ambient temperature, the reaction medium is concentrated dry and the raw residue is purified by silica gel column chromatography and is next precipitated in a chloroform/pentane mixture.

Example 71: 2-(pyridin-2-yl)pyrazolo[1',2': 1,2][1,2,3]triazolo[4,5-b]pyrazin-6-ium-5-ide (148)

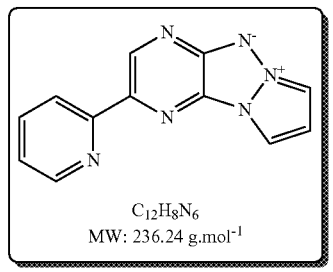

(148)

C₁₂H₈N₆
MW: 236.24 g.mol⁻¹

This compound was prepared according to General procedure D using 2-(tributylstannyl)pyridine (1 mmol). The reaction mixture is left under reflux agitation of the solvent for 30 h. The raw residue is purified by chromatography on silica gel column (DCM/MeOH: 100/0, 99/1, 98/2, 97/3; solid deposition). The product (148: example 71) is obtained with a yield of 87% in the form of an orange powder. NMR ($^1$H, 400 MHz, chloroform-d) δ 9.51 (t, 1H), 8.65 (d, J=4.2 Hz, 1H), 8.11 (d, J=3.0 Hz, 1H), 7.84 (m, 1H), 7.77 (t, J=7.7 Hz, 1H), 7.23 (t, 1H), 6.91 (t, 1H). NMR (13C, 101 MHz, chloroform-d) δ 154.8, 152.4, 149.5, 142.7, 137.7, 137.0, 128.4, 122.8, 120.0, 110.7, 109.7. SM (IC+) m/z 237 (MH+).

Example 72: 2-(pyrimidin-2-yl)pyrazolo[1',2':1,2][1,2,3]triazolo[4,5-b]pyrazin-6-ium-5-ide (149)

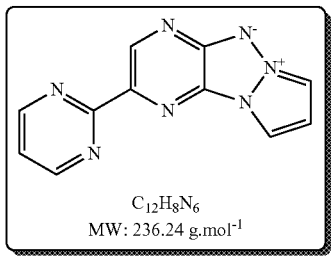

(149)

C₁₂H₈N₆
MW: 236.24 g.mol⁻¹

This compound was prepared according to General procedure D using 2-(tributylstannyl)pyrimidine (0.2 mmol). The reaction mixture is left under reflux agitation of the solvent for 24 h. The raw residue is purified by chromatography on silica gel column (DCM/AcOEt/MeOH: 85/10/5; solid deposition). The desired product (149: example 72) is obtained with a yield of 60% in the form of an orange powder. NMR ($^1$H, 400 MHz, chloroform-d) δ 9.71 (s, 1H), 8.87 (d, J=4.8 Hz, 2H), 8.31 (d, J=3.4 Hz 1H); 7.88 (d, J=2.7 Hz, 1H), 7.23 (t, 1H), 6.92 (t, J=3.0 Hz, 1H). NMR ($^{13}$C, 101 MHz, chloroform-d) δ 162.8, 157.7 (2C), 153.0, 145.4, 135.7, 129.2, 119.4, 112.4, 110.7, 109.8. SM (IC+) m/z 238 (MH⁺).

III.4. Sonogashira Coupling

General procedure E, described below, is implemented to prepare the compounds according to the invention.

General Procedure E

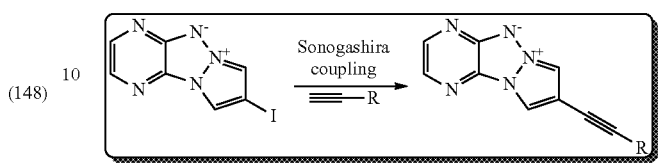

In a dry sealed tube under argon, the iodine derivative (50: example 15) (1 eq) is solubilized in an ACN/DMF (4/1: v/v, C=0.1M mixture). The distilled triethyl amine (2 eq) and the alkyne (2 eq) are added next. The reaction mixture is degassed, then the Pd(Ph₃)₂Cl₂ (0.1 eq) and the CuI (0.1 eq) are introduced. The reaction medium is left under agitation at ambient temperature until the iodine derivative is completely consumed. The solvent is next eliminated by vacuum evaporation and the raw residue is purified by silica gel column chromatography.

Ethyl 2-(2-naphthamido)pent-4-ynoate (64.2)

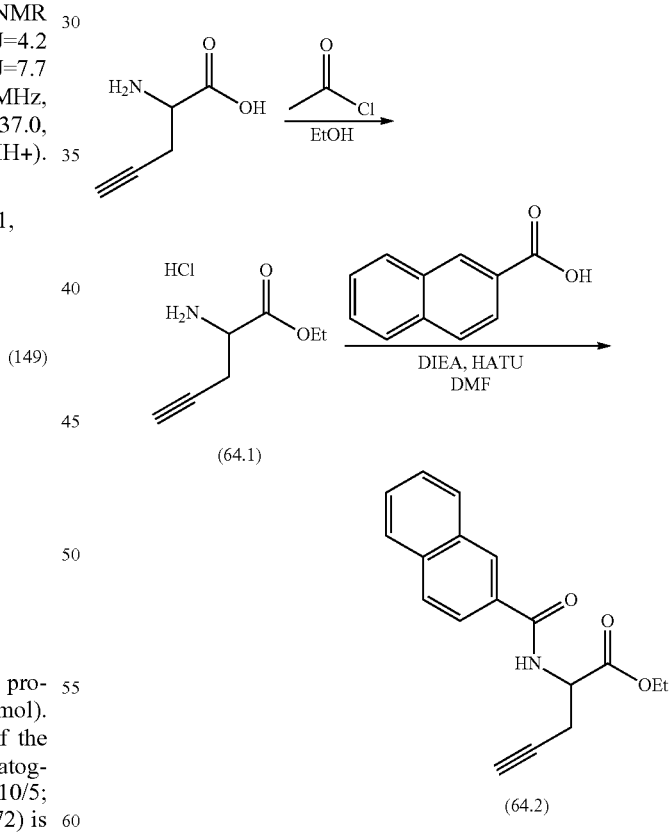

The acetyl chloride (580 μL, 8.22 mmol, 3.1 eq) is introduced into a flask containing ethanol (12 mL) cooled to 0° C. After 30 min of agitation at 0° C., the L,D-propargylglycine (300 mg, 2.65 mmol, 1 eq) is introduced in small portions. The solution is left to return to ambient temperature, then is brought to reflux for 4 h. The solvent is evaporated to obtain the salified product (64.1) in the form of a white solid with a quantitative yield (478 mg).

The intermediary (64.1) and the 2-naphthalenecarboxilic acid (456.3 mg, 2.65 mmol, 1 eq) are solubilized in the anhydrous DMF (9 mL). After adding the DIEA (1.4 mL, 7.95 mmol, 3 eq), the reaction medium is cooled to 0° C. The HATU (1 g, 2.65 mmol, 1 eq) is introduced last in small portions. The reaction medium is left under agitation at 0° C. for 2 h. After returning to ambient temperature, the solvent is evaporated and the raw solid is resolubilized in the AcOEt. The organic phase is washed successively with a saturated solution of $NaHCO_3$, then with water and with a NaCl saturated solution. The organic phase is dried on $MgSO_4$, filtered and concentrated dry to yield a brownish oil (847 mg). The raw product is purified by silica gel column chromatography (dichloromethane: 100%; solid deposition). The desired product (64.2) is obtained with a yield of 85% 683 mg: over both steps) in the form of a pale yellow solid. NMR ($^1$H, 250 MHz, chloroform-d) δ 8.35 (dd, J=1.7, 0.9 Hz, 1H), 7.99-7.78 (m, 4H), 7.64-7.47 (m, 2H), 7.15 (d, J=7.6 Hz, 1H), 4.99 (dt, J=7.6, 4.6 Hz, 1H), 4.32 (qd, J=7.1, 4.5 Hz, 2H), 2.07 (t, J=2.6 Hz, 1H). NMR ($^{13}$C, 400 MHz, chloroform-d) δ 170.68, 167.14, 135.08, 132.73, 131.11, 129.16, 128.69, 127.97, 126.96, 123.71, 78.67, 71.84, 62.28, 51.28, 22.81, 14.34.

Ethyl 2-((tert-butoxycarbonyl)amino)pent-4-ynoate (65.2)

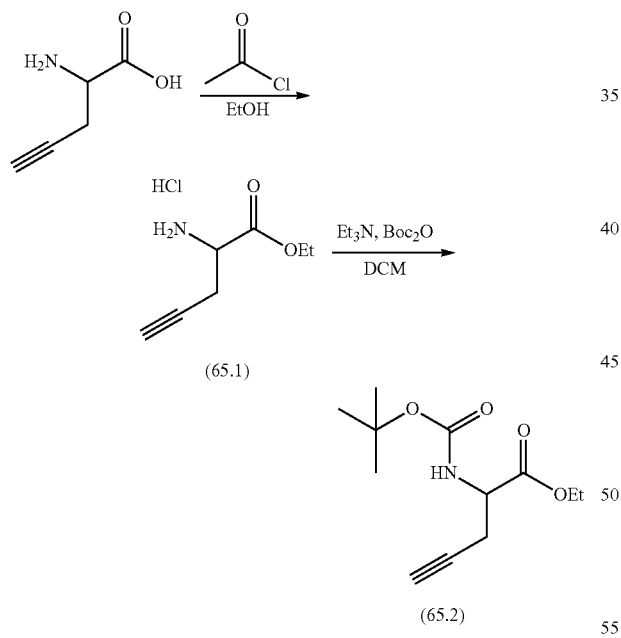

The acetyl chloride (2 mL, 27.40 mmol, 6.2 eq) is introduced into a flask containing Ethanol (40 mL) cooled to 0° C. After 30 min of agitation at 0° C., the L,D-propargylglycine (500 mg, 4.42 mmol, 1 eq) is introduced in small portions. The solution is left to return to ambient temperature, then is left under reflux agitation of the solvent for 4 h. The solvent is evaporated to obtain the salified product (65.1) in the form of a white solid with a quantitative yield.

The triethyl amine (3.1 mL, 22.10 mmol, 5 eq) is added to a solution containing ester (65.1) in the distilled dichloormethane (11 mL). After 10 min of agitation at ambient temperature, the di-tert-butyl dicarbonate (1.45 g, 6.64 mmol, 1.5 eq) is introduced. The reaction mixture is left under agitation at ambient temperature for 18 h. The medium is next washed with a solution of $K_2CO_3$ at 5% water, then washed with a saturated $NaHCO_3$ solution, dried on $MgSO_4$, filtered and concentrated dry. The raw product is purified by silica gel column chromatography (Cyclohexane/AcOEt: 8/2; liquid deposition). The desired product (65.2) in its racemic form is obtained with a yield of 97% (1.03 g: over 2 steps) in the form of a colorless oil. $R_f$ (Cyclohexane/AcOEt: 8/2): 0.44. NMR ($^1$H, 250 MHz, acetonitrile-$d_3$) δ 5.34 (d, J=7.1 Hz, 1H, NH), 4.52-4.40 (m, 1H), 4.24 (p, J=7.0 Hz, 2H), 2.73 (s, 1H), 1.45 (s, 9H), 1.29 (t, J=7.1 Hz, 3H). NMR ($^{13}$C, 400 MHz, chloroform-d) δ 170.73, 155.25, 80.27, 78.72, 71.64, 61.90, 52.08, 28.44, 27.06, 23.02, 14.31. SM (IC+) m/z 142 (M-$C_5H_7O_2$+$Na^+$), 164 (M-$C_5H_7O_2$+$H^+$), 186 (M-$C_4H_8$+$H^+$), 208 (M-$C_4H_7$+$Na^+$), 242 (M+$H^+$), 264 (M+$Na^+$).

Example 29: 8-(4-(2-naphthamido)-5-ethoxy-5-oxopent-1-yn-1-yl)pyrazolo[1′,1,2′:1,2][1,2,3]triazolo[4,5-b]pyrazin-6-ium-5-ide (66)

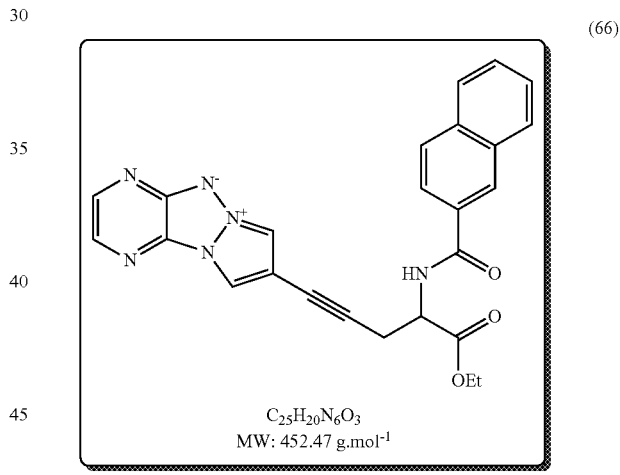

This compound was prepared according to General procedure E from ethyl 2-(2-naphthamido)pent-4-ynoate (64.2) (1.2 mmol). The reaction medium is left under agitation at ambient temperature for 4 h until total solubilization. The raw residue is purified by silica gel column chromatography (solid deposition; DCM/AcOEt: gradient from 100/0 to 7/3). The desired product (66: example 29) is obtained with a yield of 79% (477 mg) in the form of an orange powder. $R_f$ (DCM/AcOEt: 8/2): 0.25. NMR ($^1$H, 400 MHz, Acetone-$d_6$) δ 8.53 (d, J=6.9 Hz, 2H), 8.39 (s, 1H), 8.22 (s, 1H), 8.02 (d, J=4.3 Hz, 3H), 7.97 (d, J=8.3 Hz, 1H), 7.91 (s, 1H), 7.60 (p, J=7.0 Hz, 2H), 5.00 (t, J=5.9 Hz, 1H), 4.28 (p, J=6.4, 5.9 Hz, 2H), 3.21 (d, J=6.7 Hz, 2H), 2.96 (s, 1H) 1.30 (t, J=6.8 Hz, 3H). NMR ($^{13}$C, 101 MHz, Acetone-$d_6$) δ 171.21, 167.57, 153.41, 143.83, 135.80, 133.67, 132.43, 130.90, 129.84, 129.07, 128.63, 128.60, 127.63, 125.01, 113.72, 111.50, 108.10, 90.01, 72.91, 62.12, 52.93, 23.34, 14.58. SM (IC+) m/z 453 (M+$H^+$).

Example 30: 8-(4-((tert-butoxycarbonyl)amino)-5-ethoxy-5-oxopent-1-yn-1-yl)pyrazolo[1',2':1,2][1,2,3]triazolo[4,5-b]pyrazin-6-ium-5-ide (67)

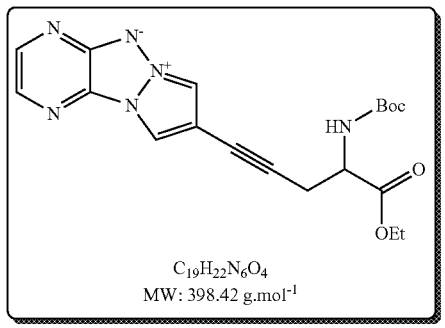

(67)

C$_{19}$H$_{22}$N$_6$O$_4$
MW: 398.42 g.mol$^{-1}$

This compound was prepared according to General procedure E from ethyl 2-(2-Boc)pent-4-ynoate (65.2) (1.26 mmol). The reaction medium is left under agitation at ambient temperature for 4 h (partial solubilization). The raw residue is purified by silica gel column chromatography (solid deposition; DCM/AcOEt from 100/0 to 9/1, then DCM/MeOH 98/2). The desired product (67: example 30) is obtained with a yield of 87% (420 mg) in the form of an orange powder. R$_f$(DCM/AcOEt: 8/2): 0.39. NMR ($^1$H, 400 MHz, acetonitrile-d$_3$) δ 8.32 (s, 1H), 8.24 (s, 1H), 7.93 (s, 1H), 7.86 (s, 1H), 5.87 (d, J=7.0 Hz, 1H), 4.46-4.32 (m, 1H), 4.17 (p, J=6.7 Hz, 2H), 2.92 (d, J=6.0 Hz, 2H), 1.39 (s, 9H), 1.23 (t, J=7.1 Hz, 3H). NMR ($^{13}$C, 101 MHz, acetonitrile-d$_3$) 142.95, 130.16, 112.84, 110.62, 61.45, 59.98, 52.44, 27.54, 22.81, 20.17, 13.59. (the quaternary carbons are not visible) SM (IC+) m/z 399 (MH$^+$).

Example 31: 8-(3-((tert-butoxycarbonyl)amino)prop-1-yn-1-yl)pyrazolo[1',2':1,2][1,2,3]triazolo[4,5-b]pyrazin-6-ium-5-ide (68)

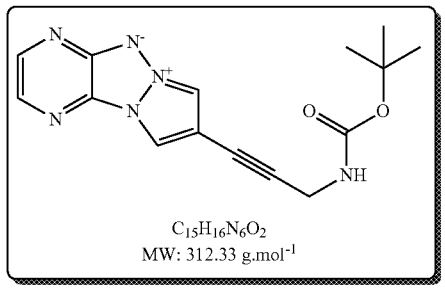

(68)

C$_{15}$H$_{16}$N$_6$O$_2$
MW: 312.33 g.mol$^{-1}$

This compound was prepared according to General procedure E from tert-butyl prop-2-ynylcarbamate (112 mg, 0.70 mmol, 2 eq). The reaction medium is left under agitation at ambient temperature for 2 h (total solubilization). The raw residue is purified by chromatography on silica gel column (DCM/AcOEt/MeOH: 10/0/0, 8/2/0 then 8/1.8/0.2; solid deposition). The desired product (68: example 31) is obtained with a yield of 78% (85 mg) in the form of a yellow powder. R$_f$(DCM/AcOEt: 8/2): 0.2. NMR ($^1$H, 400 MHz, chloroform-d) δ 8.47 (s, 1H, H$_1$ or H$_2$), 8.11 (s, 1H, H$_3$ or H$_4$), 7.95 (s, 1H, H$_1$ or H$_2$), 7.86 (s, 1H, H$_3$ or H$_4$), 4.81 (se, 1H, H$_6$), 4.19 (d, J=5.1 Hz, 2H, H$_5$), 1.48 (s, 9H, H$_7$). NMR ($^{13}$C, 400 MHz, chloroform-d) δ 155.43, 152.80, 143.78, 132.29, 130.91, 128.69, 112.22, 110.69, 107.17, 90.09, 80.30, 72.07, 28.51. SM (IC+) m/z 313 (M+H$^+$), 257 (M-tBu+H$^+$).

Example 32: 7-(3-((tert-butoxycarbonyl)amino)prop-1-yn-1-yl)pyrazolo[1',2':1,2][1,2,3]triazolo[4,5-b]pyrazin-6-ium-5-ide (69)

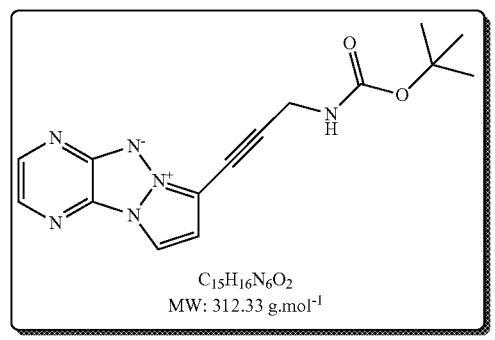

(69)

C$_{15}$H$_{16}$N$_6$O$_2$
MW: 312.33 g.mol$^{-1}$

This compound was prepared according to General procedure E from tert-butyl prop-2-ynylcarbamate (2.1 mmol). The reaction medium is left under reflux agitation of the solvent for 18 h (total solubilization). The raw residue is purified by chromatography on silica gel column (DCM/AcOEt: 10/0 and 8/2; solid deposition). The desired product (69: example 32) is obtained with a yield of 37% (123 mg) in the form of a yellow powder. NMR ($^1$H, 250 MHz, chloroform-d) δ 8.52 (d, J=2.7 Hz, 1H), 8.02-7.92 (m, 2H), 6.97 (d, J=3.5 Hz, 1H), 4.34 (s, 2H), 1.55 (s, 9H). SM (IC+) m/z 313 (MH$^+$), 257 (M-tBu+H+), 184 (M-C$_6$H$_{10}$N+H$^+$).

Example 33: 8-(phenylethynyl)pyrazolo[1',2':1,2][1,2,3]triazolo[4,5-b]pyrazin-6-ium-5-ide (70)

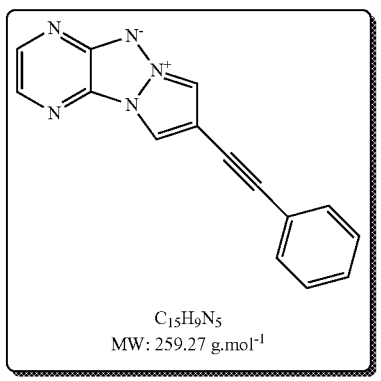

(70)

C$_{15}$H$_9$N$_5$
MW: 259.27 g.mol$^{-1}$

This compound was prepared according to General procedure E from phenyl-acetylene (1.1 mmol). The reaction medium is left under agitation at ambient temperature for 1 h30. The raw residue is purified by chromatography on silica gel column (DCM/AcOEt: 10/0, 9/1; solid deposition). The desired product (70: example 33) is obtained with a yield of 51% (41 mg) in the form of a yellow powder. $R_f$ (DCM/AcOEt/MeOH: 80/19/1): 0.85. NMR ($^1$H, 250 MHz, chloroform-d) δ 8.48 (d, J=2.7 Hz, 1H), 8.21 (s, 1H), 7.98 (s, 1H), 7.95 (d, J=2.7 Hz, 1H), 7.60-7.52 (m, 2H), 7.43-7.35 (m, 3H). NMR ($^{13}$C, 400 MHz, chloroform-d) δ 152.66, 143.75, 131.83, 130.87, 129.34, 128.69, 122.01, 111.91, 110.51, 107.86, 93.27, 78.13. SM (IC+) m/z 260 (MH$^+$).

Example 34: 8-((4-methoxyphenyl)ethynyl)pyrazolo[1,2':1,2][1,2,3]triazolo[4,5-b]pyrazin-6-ium-5-ide (71)

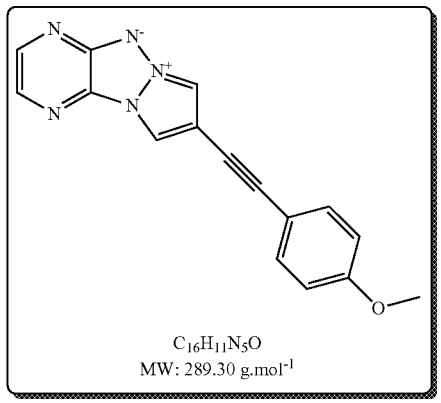

(71)

$C_{16}H_{11}N_5O$
MW: 289.30 g.mol$^{-1}$

This compound was prepared according to General procedure E from 1-ethynyl-4-methoxybenzene (0.73 mmol). The reaction medium is left under agitation at ambient temperature for 6 h (color change from yellow to green). The raw residue is purified by chromatography on silica gel column (DCM/AcOEt: 10/0, 9/1; solid deposition in DCM. The desired product (71: example 34) is obtained with a yield of 44% (41 mg) in the form of a yellow powder. $R_f$ (DCM/AcOEt/MeOH: 80/19/1): 0.41. NMR ($^1$H, 400 MHz, chloroform-d) δ 8.46 (d, J=2.7 Hz, 1H), 8.18 (s, 1H), 7.94 (d, J=1.6 Hz, 3H), 7.55-7.46 (m, 2H), 6.95-6.87 (m, 2H). NMR ($^{13}$C, 400 MHz, chloroform-d) δ 160.59, 152.64, 143.66, 133.38, 130.77, 129.16, 114.36, 114.01, 111.69, 110.54, 108.35, 93.36, 55.51. SM (IC+) m/z 290 (MH$^+$).

Example 73: 8-((4-(trifluoromethyl)phenyl)ethynyl)pyrazolo[1',2':1,2][1,2,3]triazolo[4,5-b]pyrazin-6-ium-5-ide (150)

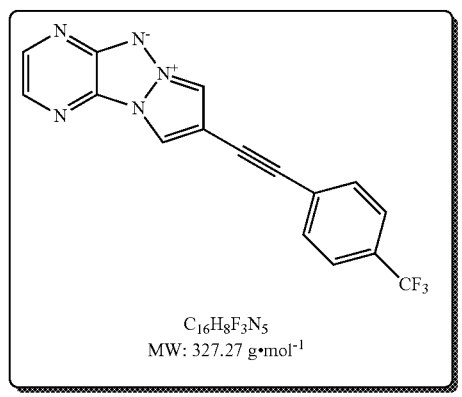

(150)

$C_{16}H_8F_3N_5$
MW: 327.27 g·mol$^{-1}$

This compound was prepared according to General procedure E from 4-trifluorophenylacetylene (1.05 mmol). The reaction medium is left under agitation at ambient temperature for 24 h. The raw residue is purified by chromatography on silica gel column (DCM/AcOEt: 100/0, 95/5; solid deposition in DCM. The desired product (150: example 73) is obtained with a yield of 58% (41 mg) in the form of a yellow powder. NMR (1H, 400 MHz, chloroform-d) δ 8.49 (d, J=2.7 Hz, 1H), 8.25 (s, 1H), 7.99 (s, 1H), 7.97 (d, J=2.7 Hz, 1H), 7.66 (s, 4H). NMR (13C, 101 MHz, chloroform-d) δ 152.53, 143.79, 131.91, 130.99, 130.95, 125.67, 125.50, 125.46, 111.89, 110.18, 106.95, 91.63, 80.36. SM (IC+) m/z 328 (MH+).

Example 35: 8-((triethylsilyl)ethynyl)pyrazolo[1',2':1,2][1,2,3]triazolo[4,5-b]pyrazin-6-ium-5-ide (72)

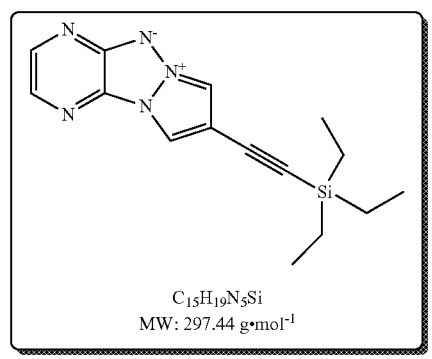

(72)

$C_{15}H_{19}N_5Si$
MW: 297.44 g·mol$^{-1}$

This compound was prepared according to General procedure E from triethyl(ethynyl)silane (0.73 mmol). The reaction medium is left at ambient temperature for 7 h (color change from yellow to green). The raw residue is purified by chromatography on silica gel column (DCM/Cyclohexane: 10/0, 8/2; solid deposition in DCM). The desired product (72: example 35) is obtained with a yield of 62% (65 mg) in the form of a yellow powder. $R_f$ (cyclohexane/AcOEt: 5/5): 0.71. NMR ($^1$H, 250 MHz, chloroform-d) δ 8.45 (d, J=2.7

Hz, 1H), 8.15 (s, 1H), 7.92 (d, J=2.7 Hz, 1H), 7.88 (s, 1H), 1.06 (t, J=7.8 Hz, 9H), 0.71 (q, J=7.8 Hz, 6H). SM (IC+) m/z 298 (MH+).

Example 36: 8-((trimethylsilyl)ethynyl)pyrazolo[1',2':1,2][1,2,3]triazolo[4,5-b]pyrazin-6-ium-5-ide (73)

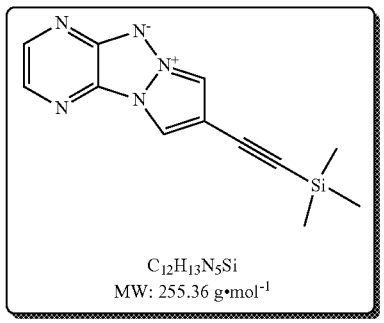

This compound was prepared according to General procedure E from trimethyl(ethynyl)silane (500 µL, 3.7 mmol, 2 eq) is added. The reaction medium is left under agitation at ambient temperature for 2 h (color change from yellow to green-brown). The raw residue is purified on silica gel column by chromatography (Cyclohexane/AcOEt: 6/4; solid deposition). The desired product (73: example 36) is obtained with a yield of 68% (304 mg) in the form of a yellow powder. NMR ($^1$H, 400 MHz, chloroform-d) δ 8.46 (d, J=2.7 Hz, 1H), 8.14 (s, 1H), 7.94 (d, J=2.6 Hz, 1H), 7.88 (s, 1H), 0.29 (s, 9H).

Example 37: 8-ethynylpyrazolo[1',2':1,2][1,2,3]triazolo[4,5-b]pyrazin-6-ium-5-ide (74)

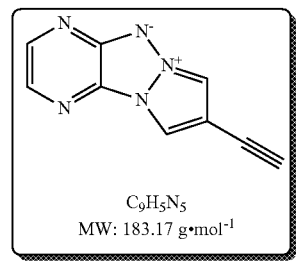

The compound (73: example 36) (230 mg, 0.90 mmol, 1 eq) is solubilized in an anhydrous ammonia solution in methanol at 7N (28 mL). The reaction mixture is left under agitation at ambient temperature for 25 min. The solvent is evaporated under reduced pressure and the raw residue is filtered on silica gel (DCM/AcOEt: 7/3) to yield the desired product (74: example 34) with a yield of 89% (147 mg) in the form of a light yellow-green powder. NMR ($^1$H, 400 MHz, chloroform-d) δ 8.47 (d, J=2.7 Hz, 1H), 8.19 (s, 1H), 7.95 (d, J=2.7 Hz, 1H), 7.92 (s, 1H), 3.23 (d, J=2.6 Hz, 1H). NMR ($^{13}$C, 101 MHz, chloroform-d) δ 152.56, 143.77, 130.89, 128.85, 112.62, 110.67, 106.36, 81.58, 72.58. SM (IC+) m/z 184 (MH+).

Example 74: Synthesis of Compound (151)

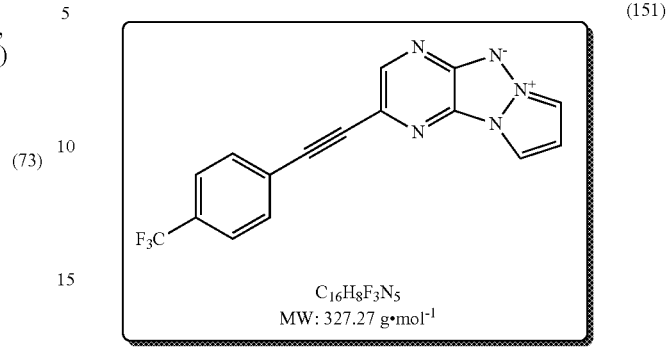

This compound was prepared according to General procedure E from 4-trifluorophenylacetylene (0.12 mmol). The reaction medium is left under agitation at ambient temperature for one night. After extraction with AcOEt and concentration, the raw residue is purified by chromatography on silica gel column (petroleum ether/AcOEt: 70/30; solid deposition in DCM). The desired product (151: example 74) is obtained with a yield in the form of a yellow powder. NMR ($^1$H, 400 MHz, chloroform-d) δ 8.69 (s, 1H), 8.14 (d, J=3.4 Hz, 1H), 7.89 (d, J=2.6 Hz, 1H), 7.72 (d, J=8.1 Hz, 2H), 7.64 (d, J=8.2 Hz, 2H), 6.97 (t, J=3.0 Hz, 1H). NMR ($^{13}$C, 101 MHz, chloroform-d) δ 151.20, 147.49, 132.03, 125.54, 123.53, 111.42, 110.44, 110.08, 89.72, 89.07. SM (IC+) m/z 328 (MH+).

Example 75: Synthesis of 7-(3-((tert-butoxycarbonyl)amino)prop-1-yn-1-yl)pyrazino[2',3':4,5][1,2,3]triazolo[2,1-a]indazol-6-ium-5-ide (152)

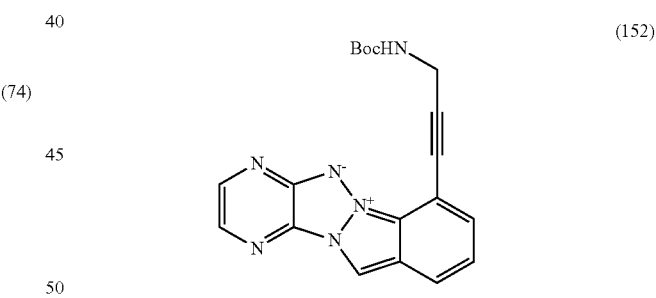

In a 100 mL tricol, 110 mg of alkyne (0.7 mmol-2 eq); 100 mg of 7-bromo indazole (129) (0.35 mmol-1 eq) and 18 mg of triphenylphosphine (0.07 mmol-0.2 eq) are introduced, dissolved in 10 mL of anhydrous triethylamine and 5 mL of anhydrous THF. The medium is then degassed with argon for fifteen minutes. Then, 14 mg of Pd(dba)$_2$ (0.02 mmol-0.05 eq) and 4 mg of CuI (0.02 mmol-0.05 eq) are added. The reaction medium is lastly brought to reflux of the solvent (80° C.). After returning to ambient temperature, the reaction medium is filtered on celite, and extracted with ethyl acetate (×2). The organic phases are gathered and washed with a solution saturated with NaHCO$_3$, dried on MgSO$_4$ and concentrated dry. The raw residue is next purified by silica gel column chromatography (dichloromethane: 100% then DCM/MeOH-gradient: 1%) to yield 0.044 g of red solid (35%).

$^1$H NMR (250 MHz, Chloroform-d) δ 8.64 (d, J=2.5 Hz, 1H), 8.53 (s, 1H), 8.07 (d, J=2.6 Hz, 1H), 7.81 (d, J=8.7 Hz, 1H), 7.39 (d, J=8.6 Hz, 1H), 4.39 (s, 1H). $^{13}$C NMR (101 MHz, CDCl$_3$) δ 151.44, 145.41, 131.51, 129.78, 128.69, 128.57, 127.36, 125.30, 123.14, 121.84, 120.16, 108.83, 101.05, 93.57, 78.34, 31.91, 28.56. HRMS (ESI): [M+H]$^+$ calculated for C$_{19}$H$_{19}$N$_6$O$_2$ 363.156400, measured 363.156550 (−0.4 ppm).

III.5. Functionalization of Position 4 of the Structures of Type [pyrazino]-1,3a,6a-triazapentalene 1-morpholinobutane-1,3-dione (153)

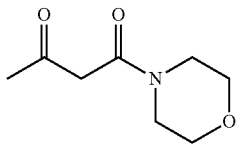

(153)

C$_8$H$_{13}$NO$_3$
MW: 171.20 g•mol$^{-1}$

The 4-DMAP (95 mg, 0.78 mmol, 0.1 eq) and morpholine (2.4 mL, 15.5 mL, 2 eq) are introduced into a solution of ethyl acetoacetate (1 mL, 7.8 mmol, 1 eq) in anhydrous toluene (80 mL). The reaction medium is placed under reflux agitation overnight (about 18 h). After returning to temperature, the solvent is evaporated under reduced pressure and the raw residue is purified by silica gel column chromatography (Cyclohexane/AcOEt: 9/1, 7/3, 5/5, 3/7; solid deposit). The desired product (153) is obtained with a yield of 95% in the form of a pale yellow crystalline solid. NMR ($^1$H, 400 MHz, chloroform-d) δ 3.70-3.61 (m, 6H), 3.56 (s, 2H), 3.48-3.34 (m, 2H), 2.28 (s, 3H).

NMR in agreement with the bibliographical data (*Eur. J. O. Chem.* 2013, 19, 4131-4145).

4-morpholino-4-thioxobutan-2-one (154)

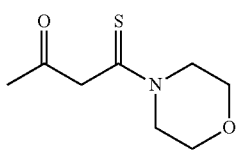

(154)

C$_8$H$_{13}$NO$_2$S
MW: 187.26 g•mol$^{-1}$

In a sealed tube, containing a solution of 1-morpholinobutane-1,3-dione (100 mg, 0.58 mmol, 1 eq) in the anhydrous toluene (5 mL), the Lawesson reagent (122 mg, 0.29 mmol, 0.5 eq) is introduced. The obtained suspension is heated by microwaves at 140° C. for 5 min. After returning to temperature, the solvent is evaporated under reduced pressure and the raw residue is purified by silica gel column chromatography (Petroleum ether/AcOEt: 7/3, 5/5; solid deposition). The desired product (154) is obtained with a yield of 79% in the form of a brown crystalline solid. NMR ($^1$H, 400 MHz, chloroform-d) δ 4.33 (t, J=4.9 Hz, 2H), 4.20 (s, 2H), 3.83-3.63 (m, 8H), 2.31 (d, J=1.2 Hz, 3H). NMR ($^{13}$C, 101 MHz, chloroform-d) δ 201.57, 192.96, 66.41, 66.36, 58.79, 51.29, 49.99, 30.26. SM (IC+) m/z 188 (MH$^+$).

4-(1-(3-chloropyrazin-2-yl)-3-methyl-1H-pyrazol-5-yl)morpholine (155)

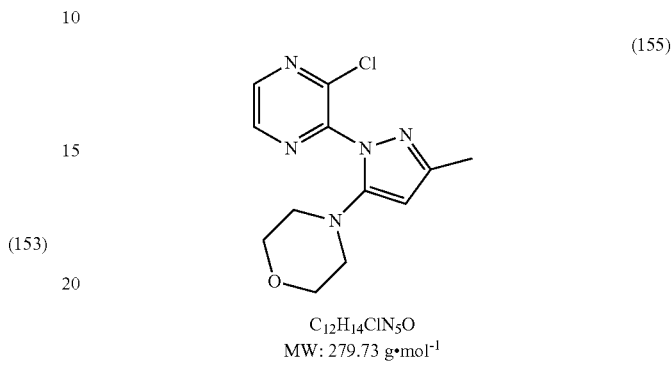

(155)

C$_{12}$H$_{14}$ClN$_5$O
MW: 279.73 g•mol$^{-1}$

In a sealed tube, dry and placed under argon, containing 4-morpholino-4-thioxobutan-2-one (50 mg, 0.27 mmol, 1 eq) and (3-chloropyrazin-2-yl)hydrazine (12) (48 mg, 0.32 mmol, 1.2 eq) in toluene (2.4 mL), pyridine (4.5 eq) is introduced. The obtained suspension is heated by microwaves at 140° C. for 45 min. After returning to temperature, the raw mixture is recovered by toluene (20 mL) and is washed with a HCl solution (0.5M). The aqueous phase is washed with a solution saturated with NaCl, dried on MgSO$_4$ and concentrated dry. The raw residue is purified by silica gel column chromatography (Cyclohexane/AcOEt: 6/4 and 5/5; solid deposition). The desired product (155) is obtained with a yield of 59% in the form of a light brown solid. NMR ($^1$H, 400 MHz, chloroform-d) δ 8.51 (d, J=2.4 Hz, 1H), 8.46 (d, J=2.4 Hz, 1H), 5.77 (d, J=0.5 Hz, 1H), 3.64-3.55 (m, 4H), 2.90-2.81 (m, 4H), 2.30 (d, J=0.4 Hz, 3H).

4-(1-(3-azidopyrazin-2-yl)-3-methyl-1H-pyrazol-5-yl)morpholine (156)

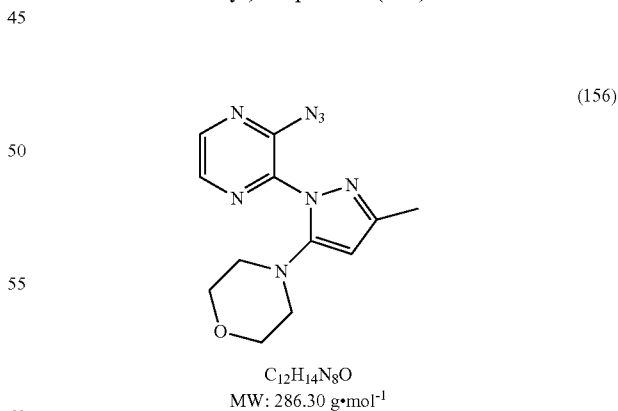

(156)

C$_{12}$H$_{14}$N$_8$O
MW: 286.30 g•mol$^{-1}$

The NaN$_3$ (70 mg, 1.1 mmol, 2 eq) is introduced into a solution of (155) (150 mg, 0.54 mmol, 1 eq) in the DMF (5 mL). The solution is heated at 100° C. for 9 h. After returning to ambient temperature, the reaction medium is concentrated and is purified by silica gel column chromatography (DCM/AcOEt: 9/1; solid deposition). The desired product (156) is obtained with a yield of 27% in the form of yellow crystals. NMR ($^1$H, 400 MHz, chloroform-d) δ 8.64 (d, J=4.5 Hz, 1H), 8.11 (d, J=4.5 Hz, 1H), 5.89 (s, 1H), 3.79 (dd, J=5.6, 3.7 Hz, 4H), 3.11 (dd, J=5.6, 3.7 Hz, 4H), 2.41 (s, 3H). NMR ($^{13}$C, 101 MHz, chloroform-d) δ 155.43, 154.33, 143.54, 130.98, 116.07, 97.66, 66.33, 52.54, 14.68, a quaternary carbon is not visible. SM (IC$^+$) m/z 287 (MH$^+$), 252 (MH$^+$—N$_2$), 309 (MNa$^+$).

Example 77: 7-methyl-9-morpholinopyrazolo[1',2': 1,2][1,2,3]triazolo[4,5-b]pyrazin-6-ium-5-ide (157)

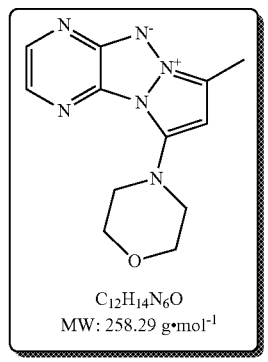

(157)

C$_{12}$H$_{14}$N$_6$O
MW: 258.29 g•mol$^{-1}$

This compound was prepared according to General procedure B from compound (156) (0.9 mmol) in 1,2-dichlorobenzene (2.5 mL). The reaction time is 2 h. After returning to ambient temperature, the raw mixture is purified by silica gel column chromatography (3 plateaus: petroleum ether: 100%; cyclohexane/ethyl acetate: 6/4, then dichloromethane/ethyl acetate 9/1). The product (157: example 77) is obtained with a yield of 85% in the form of an orange powder. NMR ($^1$H, 400 MHz, chloroform-d) δ 8.16 (d, J=2.9 Hz, 1H), 7.59 (d, J=2.9 Hz, 1H), 5.89 (s, 1H), 4.06-3.93 (m, 4H), 3.51-3.34 (m, 4H), 2.59 (s, 3H). NMR ($^{13}$C, 101 MHz, chloroform-d) δ 141.47, 139.04, 132.20, 127.11, 120.60, 100.09, 93.20, 66.28, 49.74, 10.78. SM (IC$^+$) m/z 259 (MH$^+$).

Example 78: Synthesis of Compound (158)

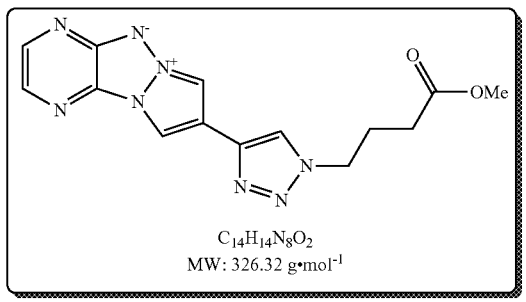

(158)

C$_{14}$H$_{14}$N$_8$O$_2$
MW: 326.32 g•mol$^{-1}$

The compound (73: example 36) (20 mg, 0.11 mmol, 1 eq) is solubilized in a tBuOH/H$_2$O (1.4 mL/0.4 mL) mixture. The methyl 4-azidobutanoate (prepared according to WO2010/082050) (19 mg, 0.13 mmol, 1.2 eq), the sodium ascorbate (8.4 mg) and the copper sulfate pentahydrate (7.3 mg) are introduced. The obtained suspension is left under agitation at ambient temperature for 24 h, then 5 h at 50° C. After returning to ambient temperature, the reaction medium is concentrated and is purified by silica gel column chromatography (DCM/MeOH: 100/0, 95/5 and 9/1). The product (158: example 78) is obtained with a yield of 86% in the form of a yellow powder. NMR ($^1$H, 400 MHz, methanol-d4) δ 8.75 (s, 1H), 8.50 (s, 1H), 8.39 (s, 1H), 8.33 (d, J=2.9 Hz, 1H), 7.94 (d, J=3.6 Hz, 1H), 4.53 (t, J=6.7 Hz, 3H), 3.64 (s, 4H), 2.46-2.36 (m, 1H), 2.31-2.19 (m, 1H). SM (IC+) m/z 327 (MH$^+$).

III.6. Functionalization of the Tetracyclic Polynitrogens

Example 79: Synthesis of Compound (159)

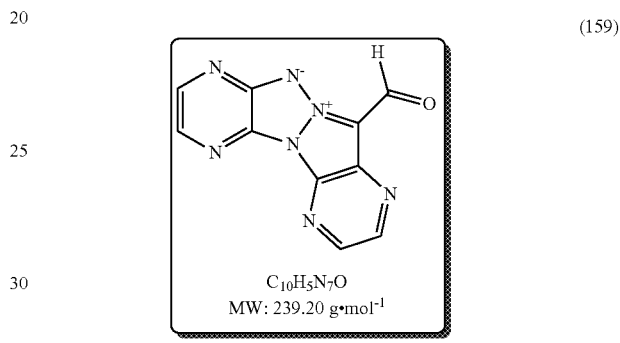

(159)

C$_{10}$H$_5$N$_7$O
MW: 239.20 g•mol$^{-1}$

In a flask containing the anhydrous DMF (0.2 mL), placed under argon atmosphere and at 0° C., the phosphorous oxychloride (54 µL, 0.56 mmol, 4 eq) is introduced dropwise. After 30 min. of agitation at this temperature, a solution of (52.1) (30 mg, 0.14 mmol, 1 eq) in the DMF (0.2 mL) is added. The obtained yellow solution is heated at 80° C. for 1 h. After returning to ambient temperature, the reaction medium is concentrated dry and is purified by silica gel column chromatography (dichloromethane/ethyl acetate: 95/5; solid deposition). The desired product (159: example 79) is obtained with a yield of 54% (34 mg) in the form of a yellow powder. NMR ($^1$H, 400 MHz, chloroform-d) δ 10.68 (s, 1H), 9.01 (d, J=2.5 Hz, 1H), 8.90 (d, J=2.5 Hz, 1H), 8.71 (d, J=2.5 Hz, 1H), 8.64 (d, J=2.5 Hz, 1H). SM (IC$^+$) m/z 240 (MH$^+$).

Example 80: Synthesis of Compound (160)

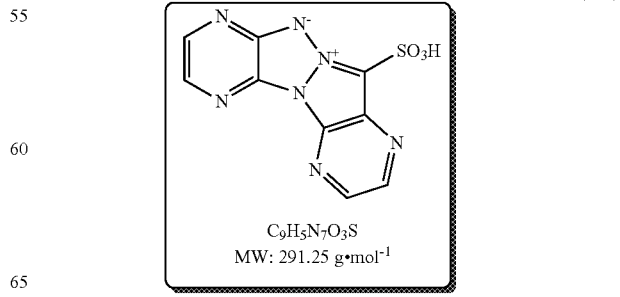

(160)

C$_9$H$_5$N$_7$O$_3$S
MW: 291.25 g•mol$^{-1}$

The chlorosulfonic acid (20 μL, 0.3 mmol, 2.5 eq) is added to a solution of (52.1) in CHCl₃ (2 mL). The obtained orange suspension is left under agitation at 80° C. for 2 h (an orange precipitate forms and accumulates on the walls). After returning to ambient temperature, the medium is concentrated and the residue is purified by reverse phase chromatography (H₂O/MeOH: 80/20; liquid deposition with H₂O). The desired product (160: example 80) is obtained with a yield of 15% (5 mg) in the form of a yellow powder. NMR (1H, 400 MHz, D2O) δ 8.99 (d, J=2.4 Hz, 1H), 8.79 (d, J=2.4 Hz, 1H), 8.70 (d, J=2.8 Hz, 1H), (d, J=2.8 Hz, 1H). NMR (13C, 101 MHz, D2O) δ 150.32 (Cq), 144.74, 142.31, 139.73, 135.51, 132.26 (Cq), 132.04 (Cq), 131.70 (Cq), 130.37 (Cq). SM (IC⁺) m/z 292 (MH⁺), 314 (MNa⁺).

Example 81: Synthesis of Compound (161)

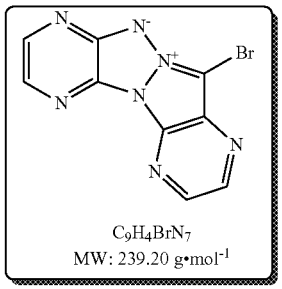

(161)

The NBS (46 mg, 0.26 mmol, 1.1 eq) is added in small portions to a solution of compound (52.1) (50 mg, 0.24 mmol, 1 eq) in the ACN (4 mL), placed at 0° C. and under argon atmosphere. The reaction mixture is left under agitation while allowing the temperature to return gently to ambient temperature. After 3 h of reaction, the reaction mixture is recovered by DCM. The organic phase is washed with a solution of Na₂S₂O₃, then water, is dried on MgSO₄ and concentrated dry. The raw residue is filtered on a silica bed (dichloromethane/ethyl acetate: 10/0 and 95/5; solid deposition). The desired product (161: example 81) is obtained with a yield of 83% (55 mg) in the form of an orange powder. NMR (¹H, 400 MHz, chloroform-d) δ 8.92 (d, J=2.4 Hz, 1H), 8.68 (d, J=2.4 Hz, 1H), 8.64 (d, J=2.8 Hz, 1H), 8.30 (d, J=2.7 Hz, 1H). NMR (¹³C, 101 MHz, chloroform-d, 10K scans) δ 144.47, 143.01, 139.53, 134.36, the quaternary carbons are not visible. SM (IC+) m/z 240 (MH⁺).

Example 82: Synthesis of Compound (162)

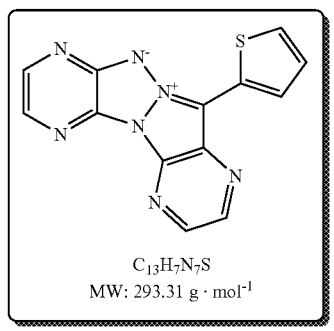

(162)

This compound was prepared according to General procedure C: using the 2-thienylboronic acid (12 mg, 0.09 mmol, 1.5 eq) in the 1,4-dioxane/H₂O (1.2 mL/0.4 mL). The reaction medium is left under agitation at 50° C. for 1 h and at 70° C. for 3 h. After returning to ambient temperature, the reaction medium is concentrated dry and the raw residue is purified by silica gel column chromatography (dichloromethane/ethyl acetate: 10/0 and 90/10; solid deposition). The desired product (162: example 82) is obtained with a yield of 86% (15 mg) in the form of an orange powder. NMR (¹H, 400 MHz, chloroform-d) δ 8.98 (d, J=2.4 Hz, 1H), 8.71 (d, J=2.4 Hz, 1H), 8.66 (dd, J=3.8, 1.1 Hz, 1H), 8.57 (d, J=2.8 Hz, 1H), 8.24 (d, J=2.8 Hz, 1H), 7.65 (dd, J=5.0, 1.0 Hz, 1H), 7.36 (dd, J=5.0, 3.8 Hz, 1H). NMR (¹³C, 101 MHz, chloroform-d, 10K scans) δ 143.62, 142.27, 139.45, 133.87, 128.03, 128.00, 128.00, the quaternary carbons are not visible. SM (IC+) m/z 294 (MH⁺).

Example 83: Synthesis of Compound (163)

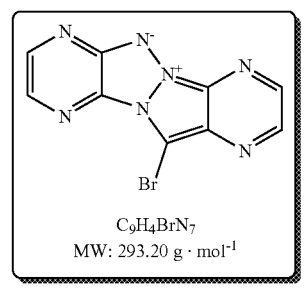

(163)

The NBS (27.5 mg, 1.1 eq) is added in small portions to a solution of compound (52.2) (30 mg, 1 eq) in the ACN (2.5 mL), placed at 0° C. and under argon atmosphere. The reaction mixture is left under agitation while allowing the temperature to return gently to ambient temperature. After 3 h of reaction, the reaction mixture is recovered by DCM. The organic phase is washed with a solution of $Na_2S_2O_3$, then water, is dried on $MgSO_4$ and concentrated dry. The raw residue is filtered on a silica bed (dichloromethane/ethyl acetate: 10/0 and 95/5; solid deposition). The desired product (163: example 83) is obtained with a yield of 26% in the form of a purple powder. NMR ($^1$H, 400 MHz, chloroform-d) δ 8.97 (d, J=1.9 Hz, 1H), 8.84 (d, J=2.3 Hz, 1H), 8.69 (d, J=1.9 Hz, 1H), 8.39 (d, J=2.3 Hz, 1H). NMR (13C, 101 MHz, chloroform-d, 10K scans) δ 147.03, 146.71, 141.59, 134.70, the quaternary carbons are not visible. SM (IC+) m/z 240 (MH$^+$).

Example 84: triazapentalene 7-bromo-3-sodium sulfonate (164)

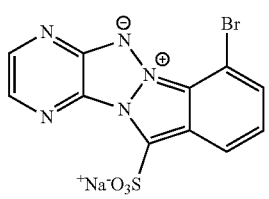

(164)

In a flask, under argon, 0.231 mL of chlorosulfonic acid (3.47 mmol, 10 eq.) is poured. The flask is submerged in an ice bath and 0.100 g of (129) (0.35 mmol, 1 eq.) dissolved in 5 mL of anhydrous dichloromethane is added. The reaction is left under agitation for one night and the temperature is allowed to rise to ambient temperature. The following day, the reaction is stopped by adding ice and several mL of NaOH 1M. The reaction is extraction with water and washed with ethyl acetate. The aqueous phase is collected and concentrated under reduced pressure. The residue is next purified by reverse phase chromatography with a water/MeOH gradient to provide 24 mg of (164) (0.062 mmol, 18%) after lyophilization.

$^1$H NMR (250 MHz, Deuterium Oxide) δ 8.68 (d, J=2.5 Hz, 1H), 8.39 (d, J=2.5 Hz, 1H), 8.06 (d, J=8.7 Hz, 1H), 7.41 (d, J=7.3 Hz, 1H), 7.27-7.17 (m, 1H). $^{13}$C NMR (63 MHz, $D_2O$) δ 149.08, 145.12, 134.44, 129.63, 128.14, 127.10, 122.67, 119.88, 118.77, 116.19, 103.09. HRMS (ESI): [M+H]$^+$ calculated for $C_{11}H_7BrN_5O_3S$ 367.944749, measured 367.944495 (0.7 ppm).

IV—Photophysical Characterization of the Inventive Compounds a. Determination of a Quantum Efficiency The quantum efficiency is an intrinsic property of fluorophores and is essential for characterizing new molecules having interesting photophysical properties. According to the definition, the quantum efficiency ($\phi_F$) is the ratio of the quantity of photons emitted to the number of photons absorbed per unit of time. Here, we will use the simplest case of this definition, namely the strong dilution of the samples to be analyzed.

To calculate the quantum efficiency, we used the comparative method. The principle consists of comparing the emission spectrums of the molecule of interest with a reference whose quantum efficiency is known. The quantum efficiency of fluorescence is calculated using the following equation:

$$\Phi(x) = \Phi(ref) \frac{K(x)}{K(ref)} \frac{n(x)^2}{n(ref)^2}$$

The φ(x) corresponds to the quantum efficiency of the compound to be analyzed and the φ(ref) is the quantum efficiency of the reference. The values of K(x) and K(ref) represent the values of the slopes of the lines obtained by tracing the fluorescence surfaces as a function of the absorption intensity. The n(x) and n(ref) represent the refraction indices of the solvents in which the analysis has been done.

As reference fluorophore, a molecule is chosen for which the absorption and emission maxima are close to those of the product to be analyzed. The reference that has a profile most closely approaching our compounds is COUMARINE 153 (which has a fluorescence efficiency of 0.38 calculated in ethanol). The concentrations of the two chromophores are next adjusted so as to have maximal absorptions comprised between 0.1 and 0.01 making it possible to avoid the internal filter effects.

b. Evolution of the Photophysical Properties of the Fluorescent Chromophores as a Function of the Solvent

| Reference | Structure | Solvent | $\lambda_{Abs}$(nm) | $\lambda_{exc}$(nm) | $\lambda_{Em}$(nm) | Relative fluorescence intensity |
|---|---|---|---|---|---|---|
| Example 7 | | DMSO | 414 | 414 | 501 | 3403 |
| | | MeOH | 407 | 407 | 510 | 734 |
| | | CHCl$_3$ | 409 | 409 | 468 | 7389 |
| | | ACN | 409 | 409 | 488 | 5665 |
| | | DCM | 410 | 410 | 468 | 8117 |
| | | Acetone | 410 | 410 | 480 | 5009 |
| | | H2O | 404 | 404 | 513 | 334 | c. Photophysical Analyses in the DMSO

| Ref. | Structure | $\lambda_{Abs}$ (nm) | $\lambda_{exc}$ (nm) | $\lambda_{Em}$ (nm) | $\varepsilon$ (L · mol$^{-1}$ · cm$^{-1}$) | $\Phi_F$ (%) | $\varepsilon \Phi_F$ |
|---|---|---|---|---|---|---|---|
| DS102 | 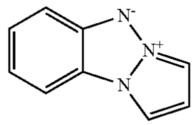 [SMILES: c1ccc2c(c1)[n-][n+]1cccn21] | 370 | 370 | No fluorescent | 12700 | Ø | Ø |
| FST-L-14H04 | 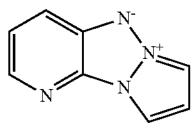 [SMILES: c1cnc2c(c1)[n-][n+]1cccn21] | 387 | 387 | 446 | 18700 | 1.8 | 340 |
| DS234 | 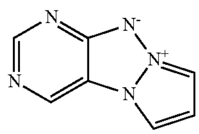 [SMILES: c1cn2c3cncnc3[n-][n+]2c1] | 362 | 399 | 447 | 7107 (at 362 nm)<br>1174 (at 399 nm) | 15.4 | 181 |
| DS136 | 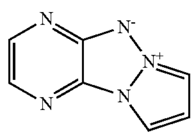 [SMILES: c1cn2c3nccnc3[n-][n+]2c1] | 418 | 418 | 516 | 15500 | 15 | 2330 |
| FST-L-14H06 | 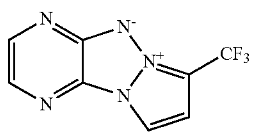 [SMILES: FC(F)(F)c1ccn2c3nccnc3[n-][n+]12] | 373 | 373 | Not fluorescent | 12600 | Ø | Ø |
| DS54 | 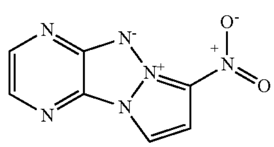 | 461 | 411 | 508 | 2400 ($\lambda$ = 461) | <0.1 | <2 |
| DS28<br>DS104 | 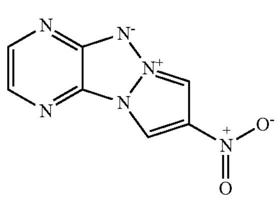 | 384 | 420 | 516 | 4300 ($\lambda$ = 420) | <0.1 | <4 |
| DS75 | 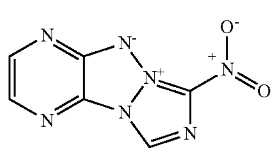 | 445 | 360 | 494 | 30000 ($\lambda$ = 445) | <0.1 | <30 |
| DS55 | 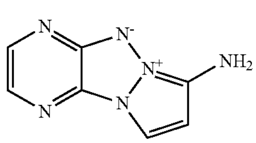 [SMILES: Nc1ccn2c3nccnc3[n-][n+]12] | 458 | 458 | 550 | 9300 | 0.6 | 60 |
| FST-L-14H05 | 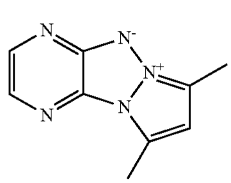 | 397 | 397 | 465 | 9770 | 3.3 | 322 |

-continued

| Ref. | Structure | $\lambda_{Abs}$ (nm) | $\lambda_{exc}$ (nm) | $\lambda_{Em}$ (nm) | $\varepsilon$ (L·mol$^{-1}$·cm$^{-1}$) | $\Phi_F$ (%) | $\varepsilon\,\Phi_F$ |
|---|---|---|---|---|---|---|---|
| DS100 | 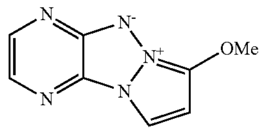 [SMILES: COc1ccn2c3nccnc3[n-][n+]12] | 437 | 437 | 526 | 13200 | 3.6 | 475 |
| DS142 | 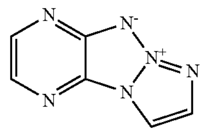 [SMILES: c1cnc2c(n1)[n-][n+]1nccn21] | 394 | 394 | 444 | 12000 | 7.2 | 860 |
| DS143 | 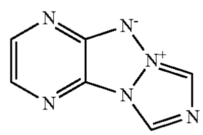 [SMILES: c1cnc2c(n1)[n-][n+]1cncn21] | 414 | 414 | 499 | 5700 | 44.9 | 2559 |
| DS323 | 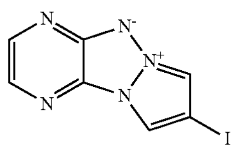 [SMILES: Ic1cn2c3nccnc3[n-][n+]2c1] | 419 | 419 | 509 | 7521 | 12.5 | 940 |
| DS303 | 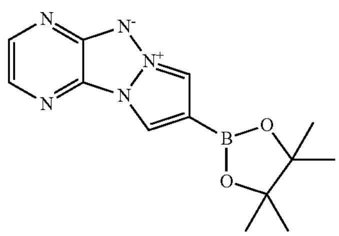 [SMILES: CC1(C)OB(c2cn3c4nccnc4[n-][n+]3c2)OC1(C)C] | 422 | 422 | 508 | 15900 | 18.8 | 2980 |
| DS293 | 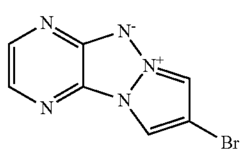 [SMILES: Brc1cn2c3nccnc3[n-][n+]2c1] | 416 | 416 | 503 | 15500 | 24.8 | 3830 |
| DS285 | 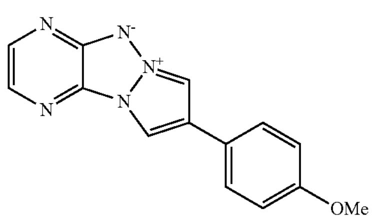 [SMILES: COc1ccc(-c2cn3c4nccnc4[n-][n+]3c2)cc1] | 421 | 421 | 517 | 13200 | 8.7 | 1150 |
| DS289 | 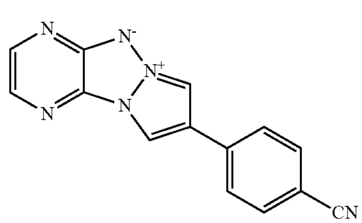 [SMILES: N#Cc1ccc(-c2cn3c4nccnc4[n-][n+]3c2)cc1] | 425 | 425 | 506 | 4285 | 25.8 | 1180 |

-continued

| Ref. | Structure | $\lambda_{Abs}$ (nm) | $\lambda_{exc}$ (nm) | $\lambda_{Em}$ (nm) | $\varepsilon$ (L · mol$^{-1}$ · cm$^{-1}$) | $\Phi_F$ (%) | $\varepsilon\,\Phi_F$ |
|---|---|---|---|---|---|---|---|
| DS333 | 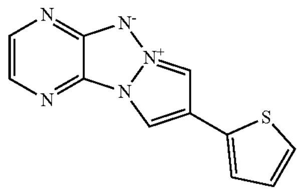 [SMILES: c1csc(-c2cn3c4nccnc4[n-][n+]3c2)c1] | 420 | 420 | 515 | 10800 | 12.3 | 1330 |
| DS261 | 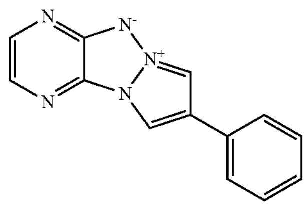 [SMILES: c1ccc(-c2cn3c4nccnc4[n-][n+]3c2)cc1] | 422 | 422 | 514 | 14300 | 14.2 | 2030 |
| DS319 | 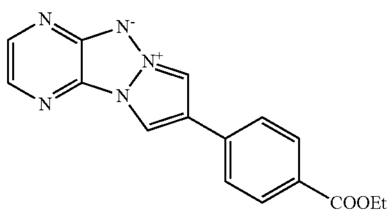 [SMILES: CCOC(=O)c1ccc(-c2cn3c4nccnc4[n-][n+]3c2)cc1] | 424 | 424 | 509 | 14662 | 22.3 | 3270 |
| DS314 | 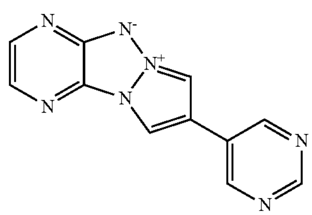 [SMILES: c1ncc(-c2cn3c4nccnc4[n-][n+]3c2)cn1] | 424 | 424 | 504 | 14200 | 28.6 | 4050 |
| DS126 | 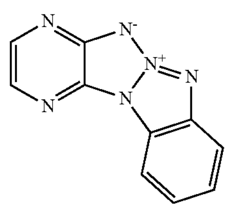 [SMILES: c1ccc2c(c1)n[n+]1[n-]c3nccnc3n21] | 393 | 460 | 512 | 215 ($\lambda$ = 460) 22200 ($\lambda$ = 393) | 55 | 118 |
| DS59 | 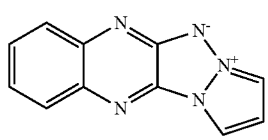 [SMILES: c1ccc2nc3c(nc2c1)[n-][n+]1cccn31] | 468 | 468 | 535 | 12700 | 3.7 | 470 |
| DS129, 213 | 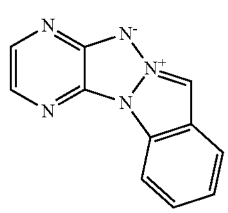 [SMILES: c1ccc2c(c1)c[n+]1[n-]c3nccnc3n21] | 425 | 425 | 495 | 20574 | 8.2 | 1687 |

-continued

| Ref. | Structure | $\lambda_{Abs}$ (nm) | $\lambda_{exc}$ (nm) | $\lambda_{Em}$ (nm) | $\varepsilon$ (L·mol$^{-1}$·cm$^{-1}$) | $\Phi_F$ (%) | $\varepsilon\,\Phi_F$ |
|---|---|---|---|---|---|---|---|
| DS367 | *structure* | 420 | 420 | 506 | 13500 | 19.8 | 2670 |
| DS366 | *structure* | 421 | 421 | 503 | 10790 | 29.6 | 3190 |
| DS368 | *structure* | 420 | 420 | 504 | 15400 | 21.1 | 3240 |
| DS335 | *structure* | 419 | 419 | 504 | 14400 | 22.7 | 3273 |
| DS365 | *structure* | 419 | 419 | 506 | 14350 | 25.5 | 3660 |

| structure | $\lambda$exc | $\lambda$em | $\varepsilon$ | $\phi$ | $\varepsilon*\phi$ |
|---|---|---|---|---|---|
| *structure* | 432 | 526 | 5729 | 5.4 | 309 |

-continued

| structure | λexc | λem | ε | φ | ε*φ |
|---|---|---|---|---|---|
| 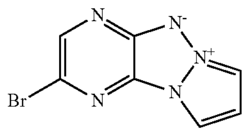 [SMILES: Brc1cnc2[n-][n+]3cccn3c2n1] | 437 | 527 | 11180 | 2 | 223 |
| 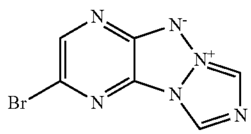 [SMILES: Brc1cnc2[n-][n+]3cncn3c2n1] | 433 | 523 | 17400 | 24.8 | 4315 |
| 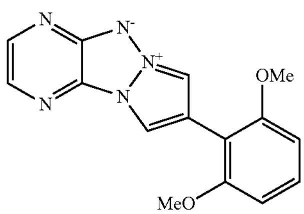 [SMILES: COc1cccc(OC)c1-c1cn2c3nccnc3[n-][n+]2c1] | 421 | 516 | 8899 | 6.2 | 551 |
| 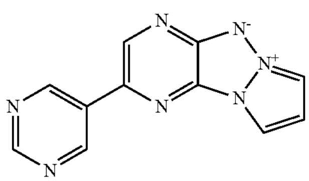 [SMILES: c1cn2c3nc(-c4cncnc4)cnc3[n-][n+]2c1] | 444 | 518 | 17500 | 17.8 | 3115 |
| 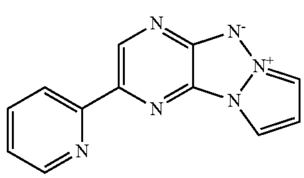 [SMILES: c1ccc(-c2cnc3[n-][n+]4cccn4c3n2)nc1] | 442 | 514 | 17560 | 30.4 | 5338 |
| 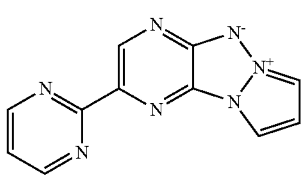 [SMILES: c1cnc(-c2cnc3[n-][n+]4cccn4c3n2)nc1] | 439 | 523 | 10221 | 30.2 | 3086 |
| 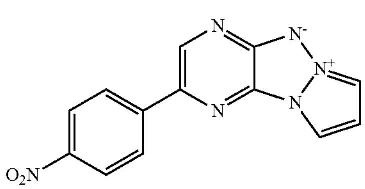 [SMILES: O=[N+]([O-])c1ccc(-c2cnc3[n-][n+]4cccn4c3n2)cc1] | 468 | 510 | 26164 | 0.1 | 26 |
| 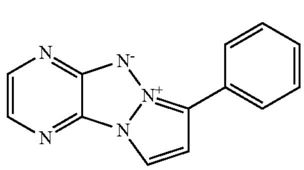 [SMILES: c1ccc(-c2ccn3c4nccnc4[n-][n+]23)cc1] | 438 | 515 | 17014 | 19.5 | 3317 |

-continued

| structure | λexc | λem | ε | φ | ε*φ |
|---|---|---|---|---|---|
| (structure) | 422 | 503 | 10731 | 31.9 | 3423 |
| (structure) | 426 | 482 | 8779 | 6.3 | 553 |
| DR-116 | 426 | 496 | 14926 | 13.60 | 2029 |
| DR-143 | 492 | 585 | 2612.27 | 0.30 | 7 |
| DR-031 | 427 | 567 | 10011 | <0.1 | <10 |
| DR-082 | 398/420/522/556 | 580 | 8700 | 8.70 | 756 |
| DR-007 | 424 | 525 | 11456.74 | 5.7 | 653 |

-continued

| structure | λexc | λem | ε | φ | ε*φ |
|---|---|---|---|---|---|
| DR-SATT-148 | 433 | 504 | 5993.4 | 25.12 | 1505 |
| DR-034 | 430 | 527 | 10377.36 | 5.1 | 529 |
| DR-EN-48 | 502 | 568 | 9658.2 | 5.8 | 560 |
| DR-SATT-186 | 496 | 565 | 12884 | 19.5 | 2512 |
| DR-EN-17 | 427 | 481 | 15579.877 | 10.2 | 1589 |
| DR-EN-35 | 446 | 486 | 9461.7 | 1.2 | 113 |

-continued
| structure | λexc | λem | ε | φ | ε*φ |
|---|---|---|---|---|---|
| 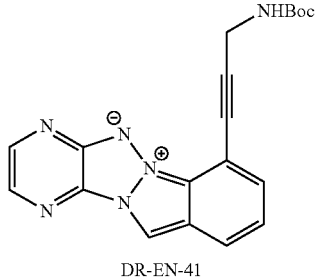 DR-EN-41 | 503 | 575 | 8653.4 | 2.7 | 233 |
| 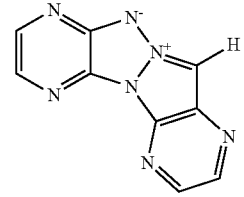 [SMILES: c1cnc2c(c[n+]3[n-]c4nccnc4n23)n1] | 446 | 525 | 19153 | 1.1 | 210 |
| 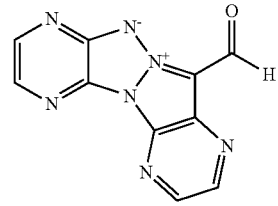 [SMILES: O=Cc1c2nccnc2n2c3nccnc3[n-][n+]12] | 449 | 493 | 27197 | | |
| 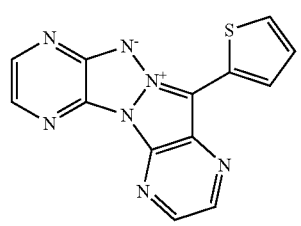 [SMILES: c1csc(-c2c3nccnc3n3c4nccnc4[n-][n+]23)c1] | 484 | 580 | 22396 | | |
| 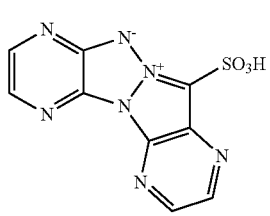 [SMILES: O=S(=O)(O)c1c2nccnc2n2c3nccnc3[n-][n+]12] | 452 | 521 | 16413 | 0.4 | 65 |
| 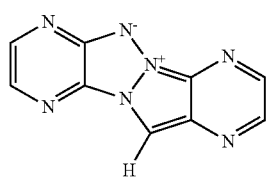 [SMILES: c1cnc2c(cn3c4nccnc4[n-][n+]23)n1] | 532 | 603 | 12147 | 10.3 | 1251 | d. Photophysical Analysis in Dichloromethane
| Ref. | Structure | $\lambda_{Abs}$ (nm) | $\lambda_{exc}$ (nm) | $\lambda_{Em}$ (nm) | $\varepsilon$ (L·mol$^{-1}$·cm$^{-1}$) | $\Phi_F$ (%) | $\varepsilon \Phi_F$ |
|---|---|---|---|---|---|---|---|
| DS129 | 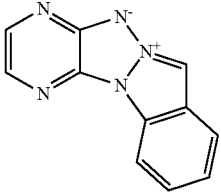 [SMILES: c1ccc2c(c1)c[n+]1[n-]c3nccnc3n21] | 421 | 421 | 477 | 34300 | 3.1 | 1060 |
| DS323 | 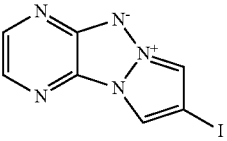 [SMILES: Ic1cn2c3nccnc3[n-][n+]2c1] | 414 | 414 | 482 | 16400 | 27.3 | 4490 |
| DS303 | 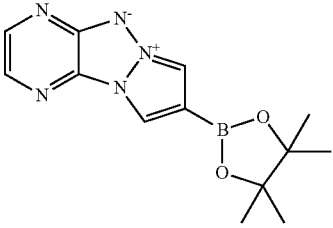 | 420 | 420 | 495 | 9300 | 50.5 | 4700 |
| DS293 | 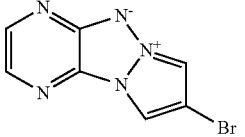 [SMILES: Brc1cn2c3nccnc3[n-][n+]2c1] | 412 | 412 | 487 | 19300 | 27.4 | 5280 |
| DS136 | 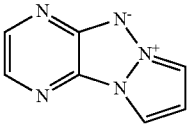 [SMILES: c1cn2c3nccnc3[n-][n+]2c1] | 415 | 415 | 494 | 13000 | 42.4 | 5500 |
| DS261 | 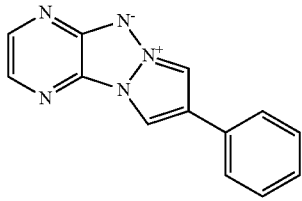 [SMILES: c1ccc(-c2cn3c4nccnc4[n-][n+]3c2)cc1] | 418 | 418 | 500 | 13800 | 44.6 | 6200 |
| DS314 | 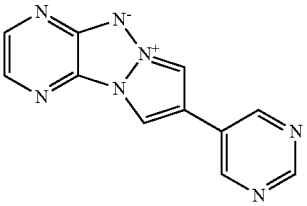 | 418 | 418 | 477 | 11500 | 50.7 | 5800 |
| DS319 | 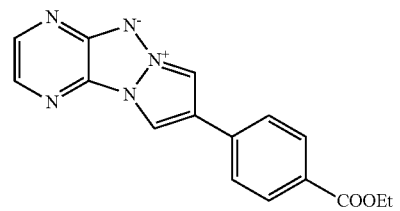 [SMILES: CCOC(=O)c1ccc(-c2cn3c4nccnc4[n-][n+]3c2)cc1] | 419 | 419 | 485 | 14200 | 47.7 | 6760 |

| structure | $\lambda_{exc}$ | $\lambda_{em}$ | ε | φ | ε*φ |
|---|---|---|---|---|---|
| 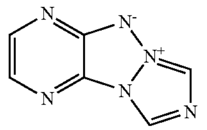 [SMILES: c1cnc2c(n1)[n-][n+]1cncn21] | 410 | 470 | 12133 | 36.6 | 4440 |
| 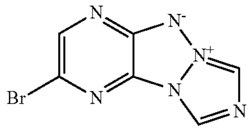 | 428 | 493 | 10500 | 63.5 | 6667 |
| 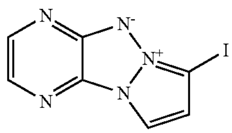 [SMILES: Ic1ccn2c3nccnc3[n-][n+]12] | 420 | 495 | 17394 | 5.4 | 939 |
| 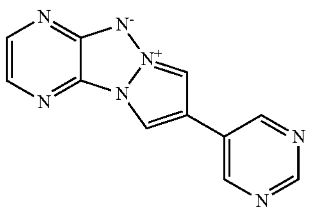 [SMILES: c1ncc(-c2cn3c4nccnc4[n-][n+]3c2)cn1] | 418 | 477 | 11500 | 50.7 | 5830 |
| | 417 | 497 | 16515 | 21.5 | 3550 |
| | 438 | 493 | 17560 | 45.3 | 7954 |
| 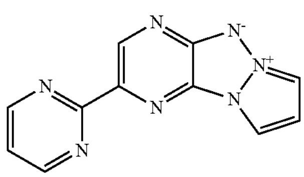 [SMILES: c1cnc(-c2cnc3[n-][n+]4cccn4c3n2)nc1] | 437 | 498 | 9590 | 37.8 | 3625 |
| | 438 | 498 | 13973 | 48.2 | 6734 |
| | 417 | 479 | 14897 | 43.5 | 6480 |

-continued

| structure | $\lambda_{exc}$ | $\lambda_{em}$ | ε | φ | ε*φ |
|---|---|---|---|---|---|
| (structure with F₃C-phenyl-alkyne-pyrazine-pyrazole) | 446 | 503 | 21957 | 48.8 | 10715 |
| (structure with alkyne-CH₂-NH-Boc) | 426 | 500 | 22366 | 14 | 3131 |
| DR-122 (Br-substituted) | 491 | 557 | 7000 | 10.80 | 756 |
| DR-126 (propargyl amide) | 470 | 547 | | 12.00 | 0 |
| (bis-pyrazine pyrazole, H) | 522 | 576 | 8600 | 67.2 | 5779 |
| (bis-pyrazine pyrazole, Br) | 530 | 604 | 3267 | 25.3 | 826 |

What is claimed is:

1. A method of detecting a biological molecule by fluorescence, comprising:
   conjugating the biological molecule with a fluorescent chromophore, and
   detecting a fluorescent signal from said fluorescent chromophore,
   wherein said fluorescent chromophore is a compound of formula (I):

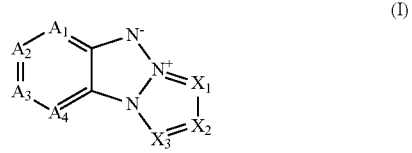

wherein:
   $A_1$ is —N— or —C($Y_1$)—;
   $A_2$ is —N— or —C($Y_2$)—;
   $A_3$ is —N— or —C($Y_3$)—;
   $A_4$ is —N— or —C($Y_4$)—;
   at least one of $A_1$, $A_2$, $A_3$ and $A_4$ representing —N—;
   $Y_1$, $Y_2$, $Y_3$ and $Y_4$ are selected independently of one another from the group consisting of: H, electron-donor groups and electron-attracting groups,
   where $Y_1$ and $Y_2$ together form, with the carbon atoms that carry them, a (hetero)cycloalkyl group or a (hetero)aryl group comprising from 5 to 30 atoms,
   and/or $Y_2$ and $Y_3$ together form, with the carbon atoms that carry them, a (hetero)cycloalkyl group or a (hetero)aryl group comprising from 5 to 30 atoms,
   and/or $Y_3$ and $Y_4$ together form, with the carbon atoms that carry them, a (hetero)cycloalkyl group or a (hetero)aryl group comprising from 5 to 30 atoms,
   $X_1$ is —N— or —C($Y_5$)—;
   $X_2$ is —N— or —C($Y_6$)—;
   $X_3$ is —N— or —C($Y_7$)—;
   $Y_5$, $Y_6$ and $Y_7$ are selected independently of one another from the group consisting of H, electron-donor groups and electron-attracting groups,
   where $Y_5$ and $Y_6$ together form, with the carbon atoms that carry them, a (hetero)cycloalkyl group or a (hetero)aryl group comprising from 5 to 10 atoms,
   and/or $Y_6$ and $Y_7$ together form, with the carbon atoms that carry them, a (hetero)cycloalkyl group or a (hetero)aryl group comprising from 5 to 10 atoms,
said compound with formula (I) being able to be in salt or pure stereoisomer form or in the form of a mixture of enantiomers and/or diastereoisomers, including racemic mixtures, or in the form of tautomers,
with the exception of the compound with formula:

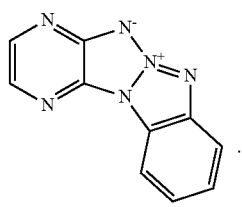 [SMILES: c1ccc2c(c1)n[n+]1[n-]c3nccnc3n21]

2. The method according to claim 1, wherein, in formula (I), $Y_1$, $Y_2$, $Y_3$ and $Y_4$ are selected independently of one another from the group consisting of: H, halogen, ($C_1$-$C_6$)alkyl, ($C_6$-$C_{10}$)aryl, heteroaryl comprising from 5 to 10 atoms, ($C_2$-$C_6$)alkenyl, ($C_2$-$C_6$)alkynyl, CN, hydroxy, ($C_1$-$C_6$)alcoxy, thiol, ($C_1$-$C_6$)alkylthio, $(CH_2)_nSO_2$—$OR_a$ where n=1-6, $CH_2SO_2$—$NR_aR_b$, $NO_2$, $SO_3R_a$, $NR_aR_b$, $C(O)OR_a$, $C(O)R_a$, and $C(O)NR_aR_b$, $R_a$ and $R_b$ representing H or a ($C_1$-$C_6$)alkyl group.

3. The method according to claim 1, wherein, in formula (I), $Y_5$, $Y_6$, and $Y_7$ represent, independently of one another, a hydrogen atom or a halogen atom, or are selected from the group consisting of:
   a ($C_1$-$C_6$)alkyl, ($C_3$-$C_6$)cycloalkyl or ($C_6$-$C_{10}$)aryl group,
   said ($C_6$-$C_{10}$)aryl group optionally being substituted by at least one substituent chosen from among: halogen, CN, ($C_1$-$C_6$)alkyl, OH, ($C_1$-$C_6$)alkoxy, $C(O)OR_a$ and $NR_aR_b$, $R_a$ and $R_b$ representing H or a ($C_1$-$C_6$)alkyl group,
   a heteroaryl group comprising from 5 to 10 chain links and containing from 1 to 4 heteroatoms chosen from among O, S or N, said heteroaryl group optionally being substituted by at least one substituent chosen from among: halogen, CN, ($C_1$-$C_6$)alkyl, OH, ($C_1$-$C_6$)alkoxy, $C(O)OR_a$ and $NR_aR_b$, $R_a$ and $R_b$ representing H or a ($C_1$-$C_6$)alkyl group,
   a heterocycloalkyl group comprising from 4 to 10 chain links and containing from one to three heteroatoms chosen from among O, S or N,
   $NO_2$,
   CHO,
   a $C(O)OR_a$ group, $R_a$ being as defined above,
   a —HC=CH—Ar group, Ar representing a ($C_6$-$C_{10}$)aryl group,
   $SO_3H$,
   a $NR_cR_d$ group, $R_c$ and $R_d$ representing H or a ($C_1$-$C_6$)alkyl group, or being able to form a hetero($C_2$-$C_5$)cycloalkyl group with the nitrogen atom that carries them;
   an $OR_e$ group, $R_e$ representing H, a ($C_1$-$C_6$)alkyl group or a ($C_6$-$C_{10}$)aryl group; and
   a group with the following formula (A):

4. The method according to claim 1, wherein $A_1$ and $A_4$ are —N—, $A_2$ is —C($Y_2$)— and $A_3$ is —C($Y_3$)—.

5. A conjugate comprising a biological molecule and a compound with formula (I) according to claim 1, in which said compound with formula (I) is linked to the biological molecule via a linker, said biological molecule being selected from the group consisting of antibodies, proteins, peptides, carbohydrates, lipids, polysaccharides, fatty acids, amino acids, deoxyribonucleic acids, ribonucleic acids, oligonucleotides, medicinal drugs and ligands.

6. The conjugate according to claim 5, with the following formula (I"):

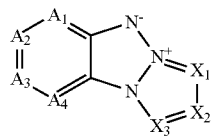

(I")

wherein:
$A_1$ is —N— or —C($Y_1$)—;
$A_2$ is —N— or —C($Y_2$)—;
$A_3$ is —N— or —C($Y_3$)—;
$A_4$ is —N— or —C($Y_4$)—;
at least one of $A_1$, $A_2$, $A_3$ and $A_4$ representing —N—;
$Y_1$, $Y_2$, $Y_3$ and $Y_4$ are selected independently of one another from the group consisting of: H, electro-donor groups and electro-attracting groups, or can represent a group with formula -L'-Z', L' representing a linker and Z' representing a biological molecule chosen from the group made up of antibodies, proteins, peptides, carbohydrates, lipids, polysaccharides, fatty acids, amino acids, deoxyribonucleic acids, ribonucleic acids, oligonucleotides, medicinal drugs and ligands,
where $Y_1$ and $Y_2$ together form, with the carbon atoms that carry them, a (hetero)cycloalkyl group or a (hetero)aryl group comprising from 5 to 30 atoms,
and/or $Y_2$ and $Y_3$ together form, with the carbon atoms that carry them, a (hetero)cycloalkyl group or a (hetero)aryl group comprising from 5 to 30 atoms,
and/or $Y_3$ and $Y_4$ together form, with the carbon atoms that carry them, a (hetero)cycloalkyl group or a (hetero)aryl group comprising from 5 to 30 atoms,
$X_1$ is —N— or —C($Y_5$)—;
$X_2$ is —N— or —C($Y_6$)—;
$X_3$ is —N— or —C($Y_7$)—;
$Y_5$, $Y_6$ and $Y_7$ are selected independently of one another from the group consisting of H, electron-donor groups and electron-attracting groups, or represent a group with formula -L'-Z', L' and Z' being as defined above,
where $Y_5$ and $Y_6$ together form, with the carbon atoms that carry them, a (hetero)cycloalkyl group or a (hetero)aryl group comprising from 5 to 10 atoms,
and/or $Y_6$ and $Y_7$ together form, with the carbon atoms that carry them, a (hetero)cycloalkyl group or a (hetero)aryl group comprising from 5 to 10 atoms,
said compound with formula (I") being able to be in salt or pure stereoisomer form or in the form of a mixture of enantiomers and/or diastereoisomers, including racemic mixtures, or in the form of tautomers,
wherein at least one of $Y_1$, $Y_2$, $Y_3$, $Y_4$, $Y_5$, $Y_6$ and $Y_7$ is a group with formula -L'-Z'.

7. A method for detecting at least one biological molecule in a biological medium, comprising:
introducing the conjugate of claim 6 into said biological medium, said conjugate comprising a fluorescent marker and a biological molecule,
exciting said medium, and
detecting at least one fluorescence signal of said fluorescent marker.

8. A method for detecting a biological molecule by fluorescence, the method comprising contacting a conjugate according to claim 5 with at least one biological molecule.

9. A method for detecting at least one biological molecule in a biological medium, comprising:
introducing the conjugate of claim 5 into said biological medium, said conjugate comprising a fluorescent marker and a biological molecule,
exciting said medium, and
detecting at least one fluorescence signal of said fluorescent marker.

10. A compound with the following formula (I'):

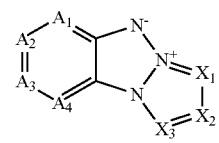

(I)

wherein:
$A_1$ is —N— or —C($Y_1$)—;
$A_2$ is —N— or —C($Y_2$)—;
$A_3$ is —N— or —C($Y_3$)—;
$A_4$ is —N— or —C($Y_4$)—;
at least one of $A_1$, $A_2$, $A_3$ and $A_4$ representing —N—;
$Y_1$, $Y_2$, $Y_3$ and $Y_4$ are selected independently of one another from the group consisting of: H, electron-donor groups and electron-attracting groups,
where $Y_1$ and $Y_2$ together form, with the carbon atoms that carry them, a (hetero)cycloalkyl group or a (hetero)aryl group comprising from 5 to 30 atoms,
and/or $Y_2$ and $Y_3$ together form, with the carbon atoms that carry them, a (hetero)cycloalkyl group or a (hetero)aryl group comprising from 5 to 30 atoms,
and/or $Y_3$ and $Y_4$ together form, with the carbon atoms that carry them, a (hetero)cycloalkyl group or a (hetero)aryl group comprising from 5 to 30 atoms,
$X_1$ is —N— or —C($Y_5$)—;
$X_2$ is —N— or —C($Y_6$)—;
$X_3$ is —N— or —C($Y_7$)—;
$Y_5$, $Y_6$ and $Y_7$ are selected independently of one another from the group consisting of H, electron-donor groups and electron-attracting groups,
said compound with formula (I) being able to be in salt or pure stereoisomer form or in the form of a mixture of enantiomers and/or diastereoisomers, including racemic mixtures, or in the form of tautomers,
with the exception of the following compounds:

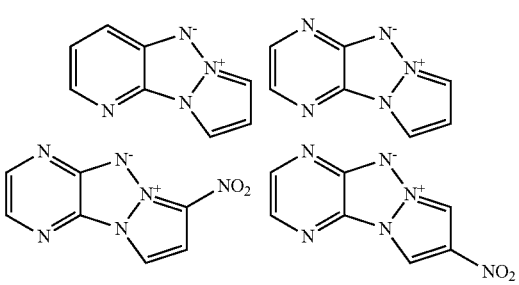

-continued

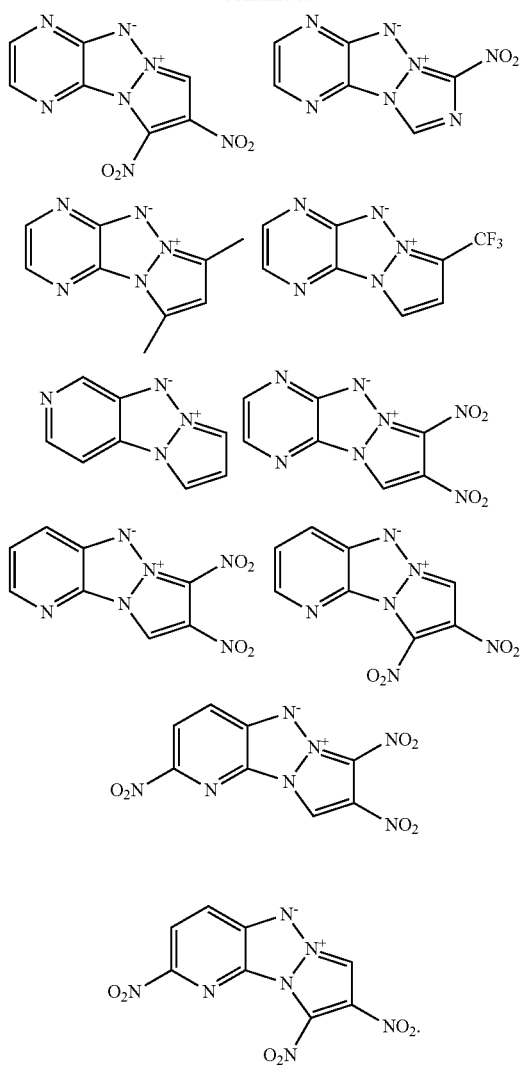

11. A compound with the following formula (III):

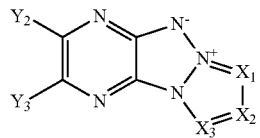

$Y_2$, $Y_3$, $X_1$, $X_2$ and $X_3$ being as defined in claim 10.

12. A compound with the following formula (III-1):

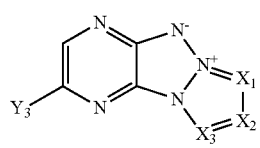

$Y_3$, $X_1$, $X_2$ and $X_3$ being as defined in claim 10.

13. A compound with the following formula (V-1):

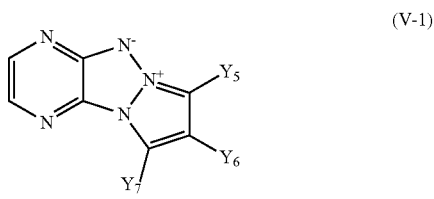

$Y_5$, $Y_6$ and $Y_7$ being as defined in claim 10.

14. A compound with the following formula (VI):

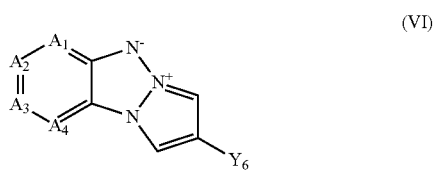

$A_1$, $A_2$, $A_3$, $A_4$ and $Y_6$ being as defined in claim 10.

15. A compound with the following formula (VII):

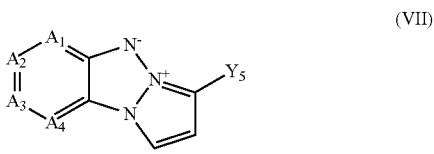

$A_1$, $A_2$, $A_3$, $A_4$ and $Y_5$ being as defined in claim 10.

16. An aqueous composition comprising at least one compound with formula (I) according to claim 10.

17. A compound with the following formula (I'):

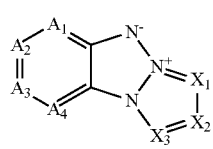

wherein:
  $A_1$ is —N— or —C($Y_1$)—;
  $A_2$ is —N— or —C($Y_2$)—;
  $A_3$ is —N— or —C($Y_3$)—;
  $A_4$ is —N— or —C($Y_4$)—;
at least one of $A_1$, $A_2$, $A_3$ and $A_4$ representing —N—;
  $Y_1$, $Y_2$, $Y_3$ and $Y_4$ are selected independently of one another from the group consisting of: H, electron-donor groups and electron-attracting groups, or can represent a group with formula -L-Z, L representing a spacer arm comprising from 1 to 10 carbon atoms and Z representing a reactive group able to bond to a biological molecule,
where $Y_1$ and $Y_2$ together form, with the carbon atoms that carry them, a (hetero)cycloalkyl group or a (hetero)aryl group comprising from 5 to 30 atoms,
and/or $Y_2$ and $Y_3$ together form, with the carbon atoms that carry them, a (hetero)cycloalkyl group or a (hetero)aryl group comprising from 5 to 30 atoms, and/or $Y_3$ and $Y_4$ together form, with the carbon atoms that carry them, a (hetero)cycloalkyl group or a (hetero)aryl group comprising from 5 to 30 atoms, $X_1$ is —N— or —C($Y_5$)—;
$X_2$ is —N— or —C($Y_6$)—;
$X_3$ is —N— or —C($Y_7$)—;

$Y_5$, $Y_6$ and $Y_7$ are selected independently of one another from the group consisting of H, electron-donor groups and electron-attracting groups, or represent a group with formula -L-Z, L and Z being as defined above, where $Y_5$ and $Y_6$ together form, with the carbon atoms that carry them, a (hetero)cycloalkyl group or a (hetero)aryl group comprising from 5 to 10 atoms, and/or $Y_6$ and $Y_7$ together form, with the carbon atoms that carry them, a (hetero)cycloalkyl group or a (hetero)aryl group comprising from 5 to 10 atoms, said compound with formula (I') being able to be in salt or pure stereoisomer form or in the form of a mixture of enantiomers and/or diastereoisomers, including racemic mixtures, or in the form of tautomers, wherein at least one of $Y_1$, $Y_2$, $Y_3$, $Y_4$, $Y_5$, $Y_6$ and $Y_7$ is a group with formula -L-Z.

18. The compound with formula (I') according to claim 17, wherein Z is selected from the group consisting of halogens, carboxylic acids, succinimide esters, tetrafluorophenyl esters, acyl azides, anhydrides, acid halogenides, acrylamides, alcohols, amines, alkynes, aminooxyacetamides, azides, imidoesters, sulfonate esters, halogeno-acetamides, alkyl halogenides, sulfonyl halogenides, hydrazines, hydrazides, isocyanates, isothiocyanates, tetrazines and maleimides.

* * * * *